(12) United States Patent
Fournier-Wirth et al.

(10) Patent No.: US 11,390,643 B2
(45) Date of Patent: *Jul. 19, 2022

(54) MODIFIED OLIGONUCLEOTIDES COMPRISING THIOL FUNCTIONS AND USE THEREOF FOR DETECTING NUCLEIC ACIDS

(71) Applicants: ETABLISSEMENT FRANÇAIS DU SANG, La Plaine Saint Denis (FR); CENTRE NATIONAL DE LA RECHERCHE SCIENTIFIQUE (CNRS), Paris (FR); UNIVERSITE DE MONTPELLIER, Montpellier (FR); UNIVERSITE CLAUDE BERNARD LYON 1, Villeurbanne (FR)

(72) Inventors: Chantal Fournier-Wirth, La Plaine Saint Denis (FR); Myriam Lereau, La Plaine Saint Denis (FR); Jean-François Cantaloube, La Plaine Saint Denis (FR); Jean-Jacques Vasseur, Combaillaux (FR); François Morvan, Castelnau le Lez (FR); Albert Meyer, Perols (FR); Julie Mayen, Vedene (FR); Carole Chaix, Chaponnay (FR); Carole Farre, Lyons (FR)

(73) Assignees: ETABLISSEMENT FRANÇAIS DU SANG, La Plaine Saint Denis (FR); CENTRE NATIONAL DE LA RECHERCHE SCIENTIFIQUE (CNRS), Paris (FR); UNIVERSITE DE MONTPELLIER, Montpellier (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 350 days.

This patent is subject to a terminal disclaimer.

(21) Appl. No.: 16/271,581

(22) Filed: Feb. 8, 2019

(65) Prior Publication Data

US 2019/0376151 A1 Dec. 12, 2019

Related U.S. Application Data

(63) Continuation of application No. 14/390,748, filed as application No. PCT/EP2013/057150 on Apr. 4, 2013, now abandoned.

(30) Foreign Application Priority Data

Apr. 4, 2012 (FR) ..................... 1253122

(51) Int. Cl.
| | |
|---|---|
| *C07H 21/00* | (2006.01) |
| *C07H 21/04* | (2006.01) |
| *C12Q 1/6832* | (2018.01) |
| *C12Q 1/70* | (2006.01) |

(52) U.S. Cl.
CPC ............. *C07H 21/00* (2013.01); *C07H 21/04* (2013.01); *C12Q 1/6832* (2013.01); *C12Q 1/707* (2013.01); *C12Q 2600/158* (2013.01)

(58) Field of Classification Search
CPC ......... C07H 21/00; C07H 21/04; C12N 15/11
See application file for complete search history.

(56) References Cited

U.S. PATENT DOCUMENTS

| 7,601,848 B2 | 10/2009 | Hartwich et al. |
| 2007/0014160 A1 | 1/2007 | Kobernik et al. |
| 2018/0265538 A1 | 9/2018 | Morvan et al. |

FOREIGN PATENT DOCUMENTS

| EP | 0523978 A1 | 1/1993 |
| JP | H06041183 A | 2/1994 |
| WO | WO-2005065405 A1 | 7/2005 |
| WO | WO-2007076493 A2 | 7/2007 |

OTHER PUBLICATIONS

International Search Report and Written Opinion of the International Search Authority regarding International Patent Application No. PCT/EP2013/057150, dated May 16, 2013.
Chattopadhyaya, Jyoti B. and Reese, Colin B., "The 9-Phenylxanthen-9-yl Protecting Group." Journal of the Chemical Society, Chemical Communications, vol. 15, pp. 639-640 (1978).
Hegner, Martin et al. "Immobilizing DNA on gold via thiol modification for atomic force microscopy imaging in buffer solutions." FEBS Letters, vol. 336, No. 3, pp. 452-456 (1993).
Phares, Noelle et al., "Improving the Stability and Sensing of Electrochemical Biosensors by Employing Trithiol-Anchoring Groups in a Six-carbon Self-assembled Monolayer." Analytical Chemistry, vol. 81, No. 3, pp. 1095-1100 (2009).
Pourceau, Gwladys etaL, "Synthesis of Mannose and Galactose Oligonucleotide Conjugates by Bi-Click Chemistry." The Journal of Organic Chemistry, vol. 74, No. 3, pp. 1218-1222 (2009).

(Continued)

*Primary Examiner* — Jezia Riley
(74) *Attorney, Agent, or Firm* — Harness, Dickey & Pierce, P.L.C.

(57) ABSTRACT

The present invention relates to a modified oligonucleotide having two or more thiol functions, which can be immobilized on a gold surface or on a grafted surface, in particular a surface comprising at least one carbon-carbon double bond or carbon-carbon triple bond or haloacetamide functions, preferably maleimide or acrylamide functions. The invention also relates to a method for detecting a nucleic acid in a biological sample comprising a step of detecting hybridization between a modified oligonucleotide and a target nucleic acid amplified from the biological sample. The invention relates more particularly to a method for detecting, genotyping or sequencing a pathogenic organism, preferably a virus.

15 Claims, 24 Drawing Sheets

Specification includes a Sequence Listing.

(56) References Cited

OTHER PUBLICATIONS

Scaramozzino et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences." Journal of Clinical Microbiology, vol. 39, No. 5, pp. 1922-1927 (2001).

Tamalet, Catherine et al., "Genomic and phylogenetic analysis of hepatitis C virus isolates: A survey of 535 strains circulating in southern France." Journal of Medical Virology, vol. 71, No. 3, pp. 391-398 (2003).

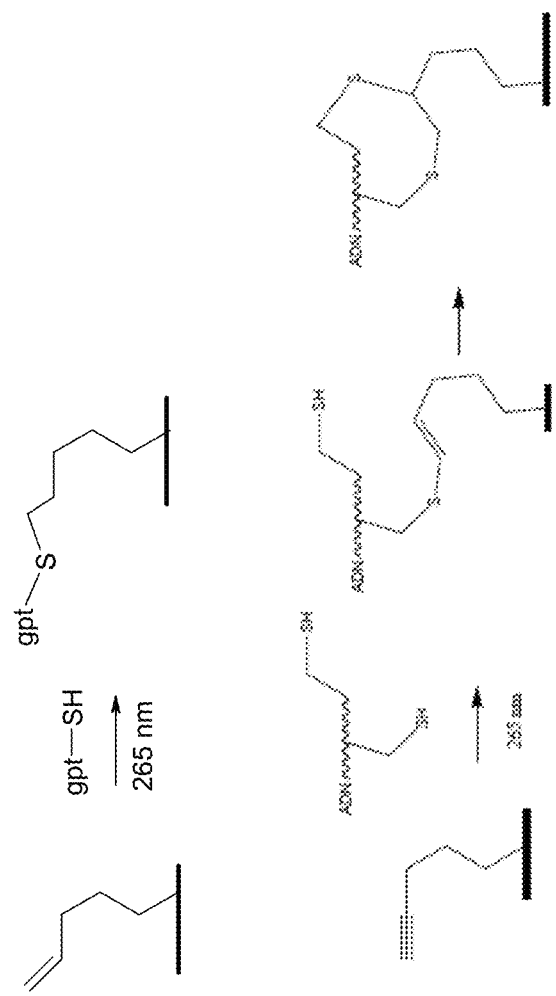

SEQUENCE LISTING

```
<160> NUMBER OF SEQ ID NOS: 44

<210> SEQ ID NO 1
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="HCV probe 1a/1b"
      /organism="artificial sequences"

<400> SEQUENCE: 1
gtgcagtccy ggagc                                                    15

<210> SEQ ID NO 2
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="HCV target 1a/1b 15-mer"
      /organism="artificial sequences"

<400> SEQUENCE: 2
gctccrggac tgcac                                                    15

<210> SEQ ID NO 3
<211> LENGTH: 105
<212> TYPE: DNA
<213> ORGANISM: artificial sequences
<220> FEATURE:
<221> NAME/KEY: source
<222> LOCATION: 1..105
<223> OTHER INFORMATION: /mol_type="DNA"
      /note="HCV target 1a/1b 105-mer"
      /organism="artificial sequences"
```

<400> SEQUENCE: 3
cctcacttgc tacatcaagg cccaggcagc ctgtcgagcc gcagggctcc gggactgcac        60
catgctcgtg tgtggcgacg acttagtcgt tatctgtgaa agtgc                      105

<210> SEQ ID NO 4
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="HCV probe 3a"
      /organism="artificial sequences"

<400> SEQUENCE: 4
ggcctccggt tcaag                                                        15

<210> SEQ ID NO 5
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="HCV target 3a 15-mer"
      /organism="artificial sequences"

<400> SEQUENCE: 5
cttgaaccgg aggcc                                                        15

<210> SEQ ID NO 6
<211> LENGTH: 105
<212> TYPE: DNA
<213> ORGANISM: artificial sequences
<220> FEATURE:
<221> NAME/KEY: source
<222> LOCATION: 1..105
<223> OTHER INFORMATION: /mol_type="DNA"
      /note="HCV target 3a 105-mer"
      /organism="artificial sequences"

<400> SEQUENCE: 6
gaacaggaca tcagggtgga agaggagata taccaatgct gtaaccttga accggaggcc        60
aggaaagtga tctcctccct cacggagcgg ctttactgcg ggggc                      105

<210> SEQ ID NO 7
<211> LENGTH: 13
<212> TYPE: DNA
<213> ORGANISM: artificial sequences
<220> FEATURE:
<221> NAME/KEY: source
<222> LOCATION: 1..13
<223> OTHER INFORMATION: /mol_type="DNA"
      /note="Nucleic acid graft test"
      /organism="artificial sequences"

<400> SEQUENCE: 7
ccaagcacga tgt                                                          13

<210> SEQ ID NO 8
<211> LENGTH: 31
<212> TYPE: DNA
<213> ORGANISM: artificial sequences
<220> FEATURE:

```
<221> NAME/KEY: source
<222> LOCATION: 1..31
<223> OTHER INFORMATION: /mol_type="DNA"
      /note="Biotinylated HCV sense primer"
      /organism="artificial sequences"

<400> SEQUENCE: 8
tggggatccc gtatgatacc cgctgctttg a                                       31

<210> SEQ ID NO 9
<211> LENGTH: 30
<212> TYPE: DNA
<213> ORGANISM: artificial sequences
<220> FEATURE:
<221> NAME/KEY: source
<222> LOCATION: 1..30
<223> OTHER INFORMATION: /mol_type="DNA"
      /note="HCV antisense primer"
      /organism="artificial sequences"

<400> SEQUENCE: 9
ggcggaattc ctggtcatag cctccgtgaa                                         30

<210> SEQ ID NO 10
<211> LENGTH: 25
<212> TYPE: DNA
<213> ORGANISM: artificial sequences
<220> FEATURE:
<221> NAME/KEY: source
<222> LOCATION: 1..25
<223> OTHER INFORMATION: /mol_type="DNA"
      /note="Biotinylated HCV sense primer 1a/1b"
      /organism="artificial sequences"

<400> SEQUENCE: 10
tgacracyag ctgyggtaay accct                                              25

<210> SEQ ID NO 11
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="HCV antisense primer 3a rev"
      /organism="artificial sequences"

<400> SEQUENCE: 11
gcagtaaagc cgytccgtga g                                                  21

<210> SEQ ID NO 12
<211> LENGTH: 401
<212> TYPE: DNA
<213> ORGANISM: Hepatitis C virus
<220> FEATURE:
<221> NAME/KEY: source
<222> LOCATION: 1..401
<223> OTHER INFORMATION: /mol_type="DNA"
      /note="Long HCV amplicon 401nt 1a/1b PTR6719"
      /organism="Hepatitis C virus"

<400> SEQUENCE: 12
tggggatccc gtatgatacc cgctgctttg actcaacggt cactgagaat gacatccgtg        60
ttgaggagtc aatttaccaa tgttgtgacc tagcccccga agccagacag gccataaggt       120
cgctcacaga gcggctttac atcggggtc ccctgactaa ttcaaaaggg cagaactgcg        180
gctatcgccg gtgccgcgcg agcggtgtgc tgacgaccag ctgcggtaat accctcacat       240
```

```
gttacttgaa ggcctctgcg gcctgtcgag ctgcaaagct ccaggactgc acaatgctcg    300
tgtgcggaga cgaccttgtc gttatctgtg aaagcgcggg aacccargag gatgcggcga    360
gcctacgagt cttcacggag gctatgacca ggaattccgc c                        401
```

```
<210> SEQ ID NO 13
<211> LENGTH: 191
<212> TYPE: DNA
<213> ORGANISM: Hepatitis C virus
<220> FEATURE:
<221> NAME/KEY: source
<222> LOCATION: 1..191
<223> OTHER INFORMATION: /mol_type="DNA"
      /note="Short HCV amplicon 191nt 1a/1b PTR6719"
      /organism="Hepatitis C virus"

<400> SEQUENCE: 13
tgacgaccag ctgcggtaat accctcacat gttacttgaa ggcctctgcg gcctgtcgag    60
ctgcaaagct ccaggactgc acaatgctcg tgtgcggaga cgaccttgtc gttatctgtg    120
aaagcgcggg aacccargag gatgcggcga gcctacgagt cttcacggag gctatgacca    180
ggaattccgc c                                                          191
```

```
<210> SEQ ID NO 14
<211> LENGTH: 401
<212> TYPE: DNA
<213> ORGANISM: Hepatitis C virus
<220> FEATURE:
<221> NAME/KEY: source
<222> LOCATION: 1..401
<223> OTHER INFORMATION: /mol_type="DNA"
      /note="Long HCV amplicon 401nt 3a PTR9058"
      /organism="Hepatitis C virus"

<400> SEQUENCE: 14
tggggatccc gtatgatacc cgctgctttg actcgactgt cactgaacag gatatcaggg    60
tggaagagga gatataccaa tgctgtaatc ttgaaccgga ggccaggaag gtgatctcct    120
ccctcacgga gcggctttac tgcggggtc ctatgttcaa cagcaaaggg gcccagtgtg    180
gttatcgccg ttgccgtgct agtggagttc tacctaccag cttcggcaat acaatcactt    240
gctacatcaa ggccacagcg gctgcaaggg ccgcaggcct ccggaacccg gactttcttg    300
tctgcggaga cgatctagtc gtggtggctg agagtgacgg cgtcgacgag gatgggggcgg   360 ccctgagagc cttcacggag gctatgacca ggaattccgc c                        401
```

```
<210> SEQ ID NO 15
<211> LENGTH: 143
<212> TYPE: DNA
<213> ORGANISM: Hepatitis C virus
<220> FEATURE:
<221> NAME/KEY: source
<222> LOCATION: 1..143
<223> OTHER INFORMATION: /mol_type="DNA"
      /note="Short HCV amplicon 143nt 3a PTR9058"
      /organism="Hepatitis C virus"

<400> SEQUENCE: 15
tggggatccc gtatgatacc cgctgctttg actcgactgt cactgaacag gatatcaggg    60
tggaagagga gatataccaa tgctgtaatc ttgaaccgga ggccaggaag gtgatctcct    120
ccctcacgga gcggctttac tgc                                            143
```

```
<210> SEQ ID NO 16
```

```
<211> LENGTH: 14
<212> TYPE: DNA
<213> ORGANISM: artificial sequences
<220> FEATURE:
<221> NAME/KEY: source
<222> LOCATION: 1..14
<223> OTHER INFORMATION: /mol_type="DNA"
      /note="Flavivirus generic probe 1"
      /organism="artificial sequences"

<400> SEQUENCE: 16
gctcccarcc acat                                                        14

<210> SEQ ID NO 17
<211> LENGTH: 14
<212> TYPE: DNA
<213> ORGANISM: artificial sequences
<220> FEATURE:
<221> NAME/KEY: source
<222> LOCATION: 1..14
<223> OTHER INFORMATION: /mol_type="DNA"
      /note="Flavivirus generic probe 2"
      /organism="artificial sequences"

<400> SEQUENCE: 17
aaccatctrt cttc                                                        14

<210> SEQ ID NO 18
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="Dengue specific probe 3"
      /organism="artificial sequences"

<400> SEQUENCE: 18
cttcyccttc yactc                                                       15

<210> SEQ ID NO 19
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="West Nile specific probe 4"
      /organism="artificial sequences"

<400> SEQUENCE: 19
ckcctcctga rttct                                                       15

<210> SEQ ID NO 20
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
      /note="MAMD sense flavivirus primer"
      /organism="artificial sequences"

<400> SEQUENCE: 20
aacatgatgg graaragrga raa                                              23
```

```
<210> SEQ ID NO 21
<211> LENGTH: 26
<212> TYPE: DNA
<213> ORGANISM: artificial sequences
<220> FEATURE:
<221> NAME/KEY: source
<222> LOCATION: 1..26
<223> OTHER INFORMATION: /mol_type="DNA"
      /note="cFD2 antisense flavivirus primer"
      /organism="artificial sequences"

<400> SEQUENCE: 21
gtgtcccagc cggcggtgtc atcagc                                          26

<210> SEQ ID NO 22
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="FS778 sense flavivirus primer"
      /organism="artificial sequences"

<400> SEQUENCE: 22
aargghagym cdgchathtg gt                                              22

<210> SEQ ID NO 23
<211> LENGTH: 263
<212> TYPE: DNA
<213> ORGANISM: Dengue virus 1
<220> FEATURE:
<221> NAME/KEY: source
<222> LOCATION: 1..263
<223> OTHER INFORMATION: /mol_type="DNA"
      /note="Dengue 1 amplicon 263nt FJ882517"
      /organism="Dengue virus 1"

<400> SEQUENCE: 23
aacatgatgg ggaagagaga gaaaaaacta ggagagttcg gaaaggcaaa aggaagtcgt      60
gcaatatggt acatgtggct gggagcacgc tttctagagt tcgaagctct tggtttcatg     120
aacgaagatc actggttcag cagagagaat tcactcagcg gagtggaagg agaaggactc     180
cacaaacttg gatatatact cagagacata tcaaagattc caggggggaaa catgtatgca    240 gatgacacag ccggatggga cac                                             263

<210> SEQ ID NO 24
<211> LENGTH: 215
<212> TYPE: DNA
<213> ORGANISM: Dengue virus 1
<220> FEATURE:
<221> NAME/KEY: source
<222> LOCATION: 1..215
<223> OTHER INFORMATION: /mol_type="DNA"
      /note="Dengue 1 amplicon 215nt FJ882517"
      /organism="Dengue virus 1"

<400> SEQUENCE: 24
aaaggaagtc gtgcaatatg gtacatgtgg ctgggagcac gctttctaga gttcgaagct      60
cttggtttca tgaacgaaga tcactggttc agcagagaga attcactcag cggagtggaa     120
ggagaaggac tccacaaact tggatatata ctcagagaca tatcaaagat tccagggggga    180 aacatgtatg cagatgacac agccggatgg gacac                                215

<210> SEQ ID NO 25
```

```
<211> LENGTH: 263
<212> TYPE: DNA
<213> ORGANISM: West Nile virus
<220> FEATURE:
<221> NAME/KEY: source
<222> LOCATION: 1..263
<223> OTHER INFORMATION: /mol_type="DNA"
      /note="WNV amplicon 263nt EF429200H442"
      /organism="West Nile virus"

<400> SEQUENCE:

```
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="Biotinylated HCV2 sense primer"
      /organism="artificial sequences"

<400> SEQUENCE: 29
atgytggtrt gcggcgacga c                                              21

<210> SEQ ID NO 30
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
      /note="Antisense HCV 4 rev primer"
      /organism="artificial sequences"

<400> SEQUENCE: 30
aggtctcccy tgctgttgtr cat                                            23

<210> SEQ ID NO 31
<211> LENGTH: 401
<212> TYPE: DNA
<213> ORGANISM: Hepatitis C virus
<220> FEATURE:
<221> NAME/KEY: source
<222> LOCATION: 1..401
<223> OTHER INFORMATION: /mol_type="DNA"
      /note="Long HCV amplicon 2 401nt PTR7761"
      /organism="Hepatitis C virus"

<400> SEQUENCE: 31
tggggatccc gtatgatacc cgctgctttg actcaactgt cactgagaga gacatcagaa    60
ccgaggagtc catataccag gcctgctccc taaccgagga ggctcgcacc gccatacact   120
cgctgactga gaggctatac gtggagggc ccatgctcaa tagcaaaggc cagacctgcg    180
ggtacaggcg ttgccgcgcc agcggggtgc tcaccactag catgggaaac accattacgt   240
gctatgtgaa agctctagcg gcatgcaagg ccgcagggat agtagcgccc acgatgctgg   300
tatgcggcga cgacctggtc gtcatctcag aaagccaggg gactgaggag gacgagcgga   360
acctgagagt cttcacggag gctatgacca ggaattccgc c                       401

<210> SEQ ID NO 32
<211> LENGTH: 401
<212> TYPE: DNA
<213> ORGANISM: Hepatitis C virus
<220> FEATURE:
<221> NAME/KEY: source
<222> LOCATION: 1..401
<223> OTHER INFORMATION: /mol_type="DNA"
      /note="Long HCV amplicon 4a/4d 401nt PTR4162"
      /organism="Hepatitis C virus"

<400> SEQUENCE: 32
tggggatccc gtatgatacc cgctgctttg actccactgt aaccgaaaga gacatcaggg    60
tcgaggagga ggtctatcag tgttgtgacc tagagcccga agcccgcaag gtaatatccg   120
ccctcacaga gagactctac gtgggcggtc ccatgtacaa cagcagggga gacctttgcg   180
gaactcgacg gtgccgtgca agcggcgtat tcaccaccag ctttgggaac acactgacgt   240
```

```
gctatcttaa ggccagcgcg gccatcaggg ctgcaggcct aaaggactgc accatgctgg      300
tctgtggcga cgacttagtc gttatcgctg aaagcgatgg cgtggaggag gacaaccgtg      360
cgctcagagc cttcacggag gctatgacca ggaattccgc c                          401
```

<210> SEQ ID NO 33
<211> LENGTH: 108
<212> TYPE: DNA
<213> ORGANISM: Hepatitis C virus
<220> FEATURE:
<221> NAME/KEY: source
<222> LOCATION: 1..108
<223> OTHER INFORMATION: /mol_type="DNA"
      /note="Short HCV amplicon 108nt 2 PTR7761"
      /organism="Hepatitis C virus"

<400> SEQUENCE: 33

```
atgctggtat gcggcgacga cctggtcgtc atctcagaaa gccaggggac tgaggaggac       60
gagcggaacc tgagagtctt cacggaggct atgaccagga attccgcc                  108
```

<210> SEQ ID NO 34
<211> LENGTH: 175
<212> TYPE: DNA
<213> ORGANISM: Hepatitis C virus
<220> FEATURE:
<221> NAME/KEY: source
<222> LOCATION: 1..175
<223> OTHER INFORMATION: /mol_type="DNA"
      /note="Short HCV amplicon 4a/4d 175nt PTR4162"
      /organism="Hepatitis C virus"

<400> SEQUENCE: 34

```
tggggatccc gtatgatacc cgctgctttg actccactgt aaccgaaaga gacatcaggg       60
tcgaggagga ggtctatcag tgttgtgacc tagagcccga agcccgcaag gtaatatccg      120
ccctcacaga gagactctac gtgggcggtc ccatgtacaa cagcagggga gacct          175
```

<210> SEQ ID NO 35
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="HCV probe 2a/2c"
      /organism="artificial sequences"

<400> SEQUENCE: 35

```
ggactcctcr gttct                                                        15
```

<210> SEQ ID NO 36
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="HCV probe 2b"
      /organism="artificial sequences"

<400> SEQUENCE: 36

```
tatggattct tctgt                                                        15
```

<210> SEQ ID NO 37
<211> LENGTH: 15

```
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="Biotinylated HCV 2a/2c 15-mer target"
      /organism="artificial sequences"

<400> SEQUENCE: 37
agaacygagg agtcc                                                     15

<210> SEQ ID NO 38
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="Biotinylated HCV 2b 15-mer target"
      /organism="artificial sequences"

<400> SEQUENCE: 38
acagaagaat ccata                                                     15

<210> SEQ ID NO 39
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="Biotinylated HCV 4a/4d 15-mer target"
      /organism="artificial sequences"

<400> SEQUENCE: 39
ctaygtgggc ggycc                                                     15

<210> SEQ ID NO 40
<211> LENGTH: 14
<212> TYPE: DNA
<213> ORGANISM: artificial sequences
<220> FEATURE:
<221> NAME/KEY: source
<222> LOCATION: 1..14
<223> OTHER INFORMATION: /mol_type="DNA"
      /note="Generic flavivirus probe 3"
      /organism="artificial sequences"

<400> SEQUENCE: 40
agccacatgw acca                                                      14

<210> SEQ ID NO 41
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="Dengue 4 specific probe"
      /organism="artificial sequences"

<400> SEQUENCE: 41
cactccactc catga                                                     15

<210> SEQ ID NO 42
```

```
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="WNV 15-mer biotinylated target"
      /organism="artificial sequences"

<400> SEQUENCE: 42
agaaytcagg aggmg                                              15

<210> SEQ ID NO 43
<211> LENGTH: 13
<212> TYPE: DNA
<213> ORGANISM: artificial sequences
<220> FEATURE:
<221> NAME/KEY: source
<222> LOCATION: 1..13
<223> OTHER INFORMATION: /mol_type="DNA"
      /note="Biotinylated generic 3 flavivirus 15-mer target"
      /organism="artificial sequences"

<400> SEQUENCE: 43
tggwcatgtg gct                                                13

<210> SEQ ID NO 44
<211> LENGTH: 15
<212> TYPE: DNA
<213> ORGANISM: artificial sequences
<220> FEATURE:
<221> NAME/KEY: source
<222> LOCATION: 1..15
<223> OTHER INFORMATION: /mol_type="DNA"
      /note="Biotinylated Dengue 4 specific 15-mer target"
      /organism="artificial sequences"

<400> SEQUENCE: 44
tcatggagtg gagtg                                              15
```

MODIFIED OLIGONUCLEOTIDES COMPRISING THIOL FUNCTIONS AND USE THEREOF FOR DETECTING NUCLEIC ACIDS

RELATED APPLICATIONS

This application is a continuation of U.S. application Ser. No. 14/390,748, entitled "MODIFIED OLIGONUCLEOTIDES COMPRISING THIOL FUNCTIONS AND USE THEREOF FOR DETECTING NUCLEIC ACIDS," and filed on Oct. 3, 2014, which is a National Stage Application of PCT/EP2013/057150 entitled "MODIFIED OLIGONUCLEOTIDES COMPRISING THIOL FUNCTIONS AND USE THEREOF FOR DETECTING NUCLEIC ACIDS," and filed on Apr. 4, 2013, which claims the benefit of French Application No. 1253122, filed on Apr. 4, 2012, the entire contents of which are incorporated herein by reference as if set forth in full.

TECHNICAL FIELD

The present invention relates to a modified oligonucleotide having two or more thiol functions, which can be immobilized on a gold surface or on a grafted surface, in particular a surface comprising at least one carbon-carbon double bond or carbon-carbon triple bond or haloacetamide functions, preferably maleimide or acrylamide functions. The invention also relates to a method for detecting a nucleic acid in a biological sample comprising a step of detecting hybridization between a modified oligonucleotide and a target nucleic acid amplified from the biological sample. The invention relates more particularly to a method for detecting, genotyping or sequencing a pathogenic organism, preferably a virus.

STATE OF THE ART

Owing to their physicochemical stability and the specificity conferred by the successive arrangement of the different nucleotides of which they are composed, the nucleic acids are molecules that are extremely well suited for use in methods for the specific detection and identification of human, animal, vegetable, bacterial or viral organisms.

These properties have led to the development of reliable and sensitive biosensors, which are composed conventionally of a molecular recognition element and a transducer. The molecular recognition element, called "probe", is generally immobilized on the surface of the transducer and displays high specificity and sensitivity for a "target" nucleic acid molecule. The role of the transducer is to convert the molecular recognition event, i.e. hybridization between the nucleotide sequences of the probe and the target, into a signal that can easily be measured. Biosensors thus exploit the capacities for pairing of two complementary nucleotide sequences contained in the probe and in the target, and generate a signal when hybridization of the two sequences takes place.

Biosensors are characterized by the method of transduction used for revealing hybridization of the probe and target sequences.

Biosensors with direct transduction make it possible to detect hybridization of the sequences without employing special labelling. They comprise for example electrochemical systems, in which transduction takes place by electron transfer reactions, such as amperometry, based on the detection of changes in current at a constant potential, conductometry, based on the detection of changes in conductivity between two electrodes, or potentiometry, based on the detection of changes in potential, at a constant current. Biosensors with direct transduction also comprise gravimetric systems, based on piezoelectric technologies, and for example exploiting the properties of a quartz crystal, whose frequency varies in response to changes taking place on its surface. Biosensors with direct transduction are generally quick and specific, but have limited sensitivity ($10^{-9}$ to $10^{-12}$ M). Biosensors with direct transduction are very suitable for producing diagnostic systems that are inexpensive, disposable and portable.

For their part, biosensors with indirect transduction require labelling of the target nucleic acid sequences, and require washing steps to be carried out before detection. Biosensors with indirect transduction are generally in the form of optical systems, in which detection is carried out in a reader coupled to a confocal microscope, based on the emission of light by one or more fluorescent markers in response to laser-induced excitation. Biosensors with indirect transduction therefore generally require heavy instruments, complicated to operate and requiring qualified personnel, but they have high sensitivity of detection ($10^{-12}$ to $10^{-15}$ M). Biosensors with indirect transduction constitute the technology that is most used in the field of diagnostics based on nucleic acids.

Biosensors, with direct or indirect transduction, make it possible to detect thousands or tens of thousands of hybridizations of nucleic acid sequences simultaneously and are generally arranged in the form of an orderly arrangement of immobilized probes in the form of dots on a solid support. Each dot contains about $10^6$ identical probes having the same nucleotide sequence, and the nucleotide sequence of the probes differs from one dot to the next.

"Microarrays" are extremely complex biosensors, comprising 1000 to $10^6$ dots with a size of about 20 to 50 μm. They are very sophisticated and expensive and are mainly intended for DNA sequencing, for investigation of genetic diseases and for analyses of polymorphism. This type of biosensor is in particular being developed by the companies Affymetrix, Illumina and Agilent. For their part, "macroarrays" are biosensors of low complexity comprising 1000 to 10000 dots with a size greater than or equal to 200 μm.

The probes can be immobilized on biosensors by covalent coupling or non-covalently. Covalent coupling of the probe with the transducer may be obtained for example by photolithography or by reaction of an aminated oligonucleotide with a surface coated with functionalized silane. The probe may also be immobilized on a metallic surface, and in particular on a gold surface, for example by means of a bond between a gold atom and a sulphur atom. However, the Au—S bond is of moderate strength, and a single gold-sulphur bond is not sufficient to immobilize a probe on the surface of gold in a very stable manner. In fact, the detection methods comprise steps, in particular of washing, which generate strong mechanical stresses that may destabilize the Au—S bond.

The probe may also be coupled to the transducer non-covalently, for example by electrostatic adsorption. Non-covalent coupling may for example result from interaction between the negatively-charged phosphates of the DNA of the probe and the surface of the transducer coated with γ-aminopropylsilane or with a layer of poly-L-lysine. The non-covalent interactions between the probe and the transducer offer little resistance to the washing steps carried out during the detection procedures, especially when detection is carried out by indirect transduction since detection of hybridization requires, after the hybridization step itself, removing the labelled target nucleotide sequences that have not become bound to the nucleotide sequence of the probe. Furthermore, non-covalent coupling does not allow significant changes in the operating conditions to increase the stringency of the steps of hybridization or washing and thus make them more specific.

Document EP 0 523 978 discloses phosphoramidite or phosphonate compounds that can be used for producing thiol-modified oligonucleotides. However, these compounds can only be introduced once, and only on the 5' end of an oligonucleotide.

Document U.S. Pat. No. 7,601,848 discloses a polyfunctional compound comprising two sulphur atoms that is intended to be incorporated in oligomers in order to create at least two gold-sulphur bonds and thus stabilize the oligonucleotide on the gold surface. Some of these compounds comprise a phosphoramidite function. The compounds used in this document are, however, manufactured from very expensive compounds and coupling of the polyfunctional compound on the oligonucleotides does not have a satisfactory yield owing to the steric hindrance of this compound. In this document, a binding agent is necessary in order to bind the thiol compounds to one another and thus effect multiple introduction of thiol compounds into an oligonucleotide.

The purpose of the invention is consequently to develop a probe formed from an oligonucleotide having at least two thiol functions, capable of being grafted simply and efficiently on various supports comprising both surfaces coated with metal (for example gold) and grafted surfaces comprising at least one carbon-carbon double bond or carbon-carbon triple bond or haloacetamide functions, preferably maleimide or acrylamide functions. The probe of the invention overcomes the aforementioned drawbacks at least partially and makes it possible to increase the specificity and sensitivity of detection of target nucleotide sequences, regardless of the type of transduction (direct or indirect) employed during detection.

The invention also aims to provide a method for detecting, sequencing and/or genotyping nucleic acids of pathogenic or infectious organisms or of genes responsible for or involved in diseases, which is economical, rapid, sensitive, more flexible and easier to automate than the existing methods.

SUMMARY OF THE INVENTION

The invention firstly relates to a modified oligonucleotide corresponding to formula (XIIb):

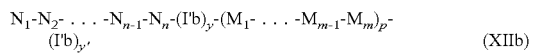
(XIIb)

or to formula (XIIIb):

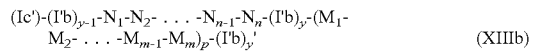
(XIIIb)

in which, $N_1, \ldots, N_n$ represent, independently of one another, a nucleotide, $M_1, \ldots, M_m$ represent, independently of one another, a nucleotide, (I'b) represents a compound of formula:

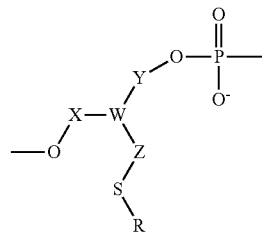

(Ic') represents a compound of formula:

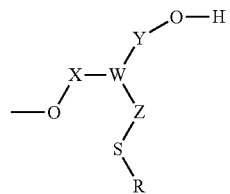

n is an integer ranging from 4 to 100, m is an integer ranging from 4 to 100, y is an integer ranging from 2 to 12, p represents 0 or 1, y' is an integer ranging from 0 to 12 if p has the value 1 and y' is equal to 0 if p has the value 0, y'' is an integer ranging from 0 to 12 if p has the value 1 and if p has the value 0 then y'' has the value 0, the sum of the integers (y+y') or (y+y'+y'') being comprised between 2 and 12, X is selected from the linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups, Y is selected from the linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups, Z is selected from the C1-C12 alkoxy groups, oxygen-containing or nitrogen-containing C3-C12 cycloheteroalkyl groups, C1-C12 NCO-alkyl groups, C1-C12 CON-alkyl groups, W is selected from the C1-C12 alkane triyl groups, the C6-C18 aryl triyl groups and the C6-C18 aralkane triyl groups, preferably a group selected from CH, CCH$_3$, CCH$_2$CH$_3$, a cyclohexane triyl and benzene triyl, R is H or is selected from the C1-C12 acyl, C1-C12 S-alkyl, C6-C12 S-aryl, S-2-pyridine, oxygen-containing or nitrogen-containing C1-C12 S-heteroalkyl, C3-C12 S-cycloalkyl, oxygen-containing or nitrogen-containing C3-C12 S-cycloheteroalkyl groups, and R1 is selected from the 2-cyanoethyl or R'$_1$R'$_2$R'$_3$SiCH$_2$CH$_2$ groups, in which R'$_1$, R'$_2$ and R'$_3$ may be identical or different and represent a group selected from the linear or branched alkyls comprising from 1 to 12 carbon atoms and the C6-C12 aryls.

According to an embodiment of the invention, the modified oligonucleotide of the invention corresponds to the formula:

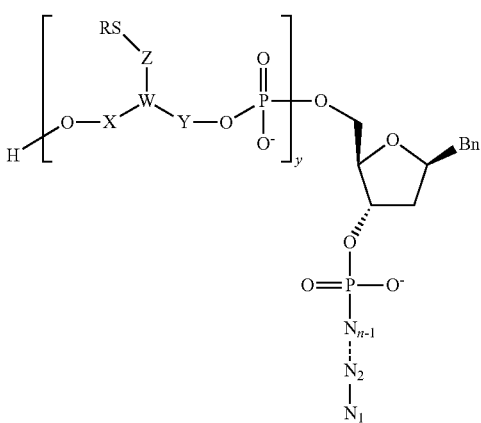

in which n, y, $N_1, \ldots, N_{n-1}$, X, Y, Z, W and R have the same definition as above, and $B_n$ represents the base of the n-th nucleotide.

According to another embodiment of the invention, the modified oligonucleotide corresponds to the formula:

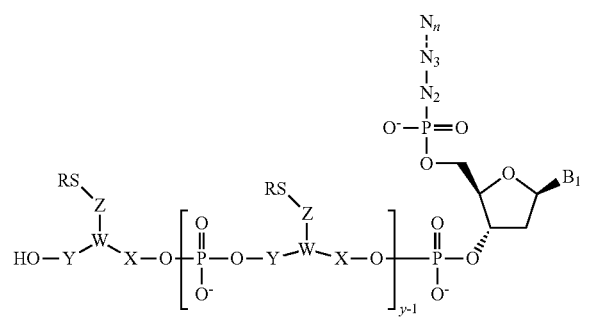

in which n, y, $N_2, \ldots, N_n$, X, Y, Z, W and R have the same definition as above, and Bi represents the base of the 1st nucleotide.

According to an embodiment of the invention, the modified oligonucleotide as described above comprises a nucleotide sequence $(N_1-N_2-\ldots-N_{n-1}-N_n)$ and, optionally, a nucleotide sequence $(M_1-M_2-\ldots-M_{m-1}-M_m)$, which are specific to a virus, a bacterium or a gene responsible for or involved in a disease.

According to an embodiment of the invention, the nucleotide sequence $(N_1-N_2-\ldots-N_{n-1}-N_n)$ and, optionally, the nucleotide sequence $(M_1-M_2-\ldots-M_{m-1}-M_m)$ are selected from:
- the sequences SEQ ID NO: 1, SEQ ID NO: 4, SEQ ID NO: 27, SEQ ID NO: 28, SEQ ID NO: 35 or SEQ ID NO: 36 specific to the hepatitis C virus (HCV),
- the sequences SEQ ID NO: 16, SEQ ID NO: 17 or SEQ ID NO: 40, specific to the flaviviruses,
- the sequence SEQ ID NO: 18 or SEQ ID NO: 41, specific to the dengue virus, or
- the sequence SEQ ID NO: 19, specific to the West Nile virus (WNV).

According to an embodiment of the invention, the nucleotide sequence $(N_1-N_2-\ldots-N_{n-1}-N_n)$ and, optionally, the nucleotide sequence $(M_1-M_2-\ldots-M_{m-1}-M_m)$ have a structure of the alpha anomer, beta anomer, linear, or stem-loop ("snail") type.

The invention further relates to a substrate grafted with at least one modified oligonucleotide as described above, said substrate comprising at least one receiving zone coated with a substance that tolerates the grafting of said modified oligonucleotide.

According to an embodiment of the invention, said receiving zone of said grafted substrate is coated with a gold or platinum film, and said substrate is of metal, preferably of copper, or said receiving zone comprises on its surface at least one carbon-carbon double bond (alkenyl function) or a carbon-carbon triple bond (alkynyl function) or haloacetamide functions, preferably maleimide or acrylamide functions, and said substrate is of plastic, preferably of polystyrene. According to an embodiment of the invention, the substrates used are non-conductive polymers. According to another embodiment of the invention, the substrates used for carrying out the invention are conductive.

According to an embodiment of the invention, the grafted substrate is flat (partly or wholly) or curved, and may advantageously be of spherical shape. According to an embodiment, the substrate is non-planar, for example in the form of microparticles or nanoparticles, and is preferably magnetic.

The invention further relates to a method for detecting at least one target nucleic acid in a biological sample, comprising a step of detecting said target nucleic acid with at least one detection probe formed by a modified oligonucleotide as described above.

According to an embodiment of the invention, the detection method of the invention comprises the steps of:
- obtaining at least one source nucleic acid from a biological sample,
- producing an amplicon by the amplification of said target nucleic acid from the source nucleic acid, and
- detecting the hybridization of said amplicon with at least one detection probe formed by a modified oligonucleotide as described above.

According to an embodiment of the invention, the detection method of the invention makes it possible to determine the genotype and/or subtype of a virus present in a biological sample, and comprises:
- generating an amplicon by the amplification of a target nucleotide sequence, corresponding to a genomic region of the virus bearing information relating to the viral genotype and/or subtype, and
- detecting the hybridization of said amplicon with at least one detection probe formed by a modified oligonucleotide as described above with a probe specific to a viral genotype and/or subtype.

According to an embodiment of the invention, the step of producing the amplicon of the detection method of the invention is carried out with a mixture of nucleotide primers, preferably selected from the primer pairs:
- SEQ ID NO: 8 and SEQ ID NO: 9, when the amplicon is generated from HCV, whatever viral genotype is involved. This primer pair is generic and allows amplification of a "long" amplicon of 401 nt starting from any genotype of HCV;
- SEQ ID NO: 10 and SEQ ID NO: 9, pair allowing the generation of "short" amplicons of 191 nt specific to genotype 1a/1b;
- SEQ ID NO: 29 and SEQ ID NO: 9, pair allowing the generation of "short" amplicons of 108 nt specific to genotype 2;
- SEQ ID NO: 8 and SEQ ID NO: 11, pair allowing the generation of "short" amplicons of 143 nt specific to genotype 3a;

SEQ ID NO: 8 and SEQ ID NO: 30, pair allowing the generation of "short" amplicons of 175 nt specific to genotype 4a/4d; and SEQ ID NO: 20 and SEQ ID NO: 21, and/or SEQ ID NO: 22 and SEQ ID NO: 21 when the amplicon is generated from a flavivirus.

The invention further relates to a kit for detecting at least one target nucleic acid in a biological sample, comprising:

at least one modified oligonucleotide as described above and at least one substrate comprising at least one receiving zone coated with a substance that tolerates the grafting of said modified oligonucleotide, said receiving zone preferably being coated with gold, with platinum or comprises at least one carbon-carbon double bond or carbon-carbon triple bond or haloacetamide functions, preferably maleimide or acrylamide functions at least one grafted substrate as described above.

The invention further relates to an oligonucleotide having a nucleotide sequence selected from the sequences SEQ ID NO: 1, SEQ ID NO: 4, SEQ ID NO: 27, SEQ ID NO: 28, SEQ ID NO: 16, SEQ ID NO: 17, SEQ ID NO: 18, SEQ ID NO: 19, SEQ ID NO: 35, SEQ ID NO: 36, SEQ ID NO: 40 and SEQ ID NO: 41.

The invention further relates to the use of an oligonucleotide or of a modified oligonucleotide as described above or of a grafted substrate as described above for detecting at least one target nucleic acid in a biological sample.

According to an embodiment of the invention, said use allows the diagnostics or genotyping of viral strains, preferably of HCV, dengue or West Nile viruses.

The advantages of the present invention are as follows:
the modified oligonucleotide of the invention bearing the thiol functions is inexpensive to produce,
the modified oligonucleotide of the invention can be immobilized stably on a gold surface, or on a surface comprising at least one carbon-carbon double bond or carbon-carbon triple bond or haloacetamide functions, preferably maleimide or acrylamide functions,
the use of the modified oligonucleotide of the invention in methods for detecting, sequencing and/or genotyping nucleic acids makes it possible to detect specifically target nucleotide sequences of several hundred nucleotides,
the nucleotide sequence of the modified oligonucleotide of the invention is advantageously shorter than those of the probes used in the known detection methods and/or of genotyping, while having better sensitivity and specificity of detection.

Other features and advantages of the invention will become apparent on reading the following description of a preferred embodiment of the invention, given as an example, and referring to the attached drawings.

BRIEF DESCRIPTION OF THE DRAWINGS

FIGS. 8 and 9 show schematic diagrams of the results of ELOSA tests with fluorescence detection, carried out with a tetrathiol probe of type 3a.

FIG. 16b shows the reactions between the modified oligonucleotide according to the invention and the surface grafted with alkenyl or alkynyl groups with activation by light ($\lambda$=265 nm).

FIG. 19 shows a schematic diagram of the results of ELOSA tests with fluorescence detection, carried out with a tetrathiol HCV probe of type 3a.

DISCLOSURE OF EMBODIMENTS OF THE INVENTION

Figure 1:
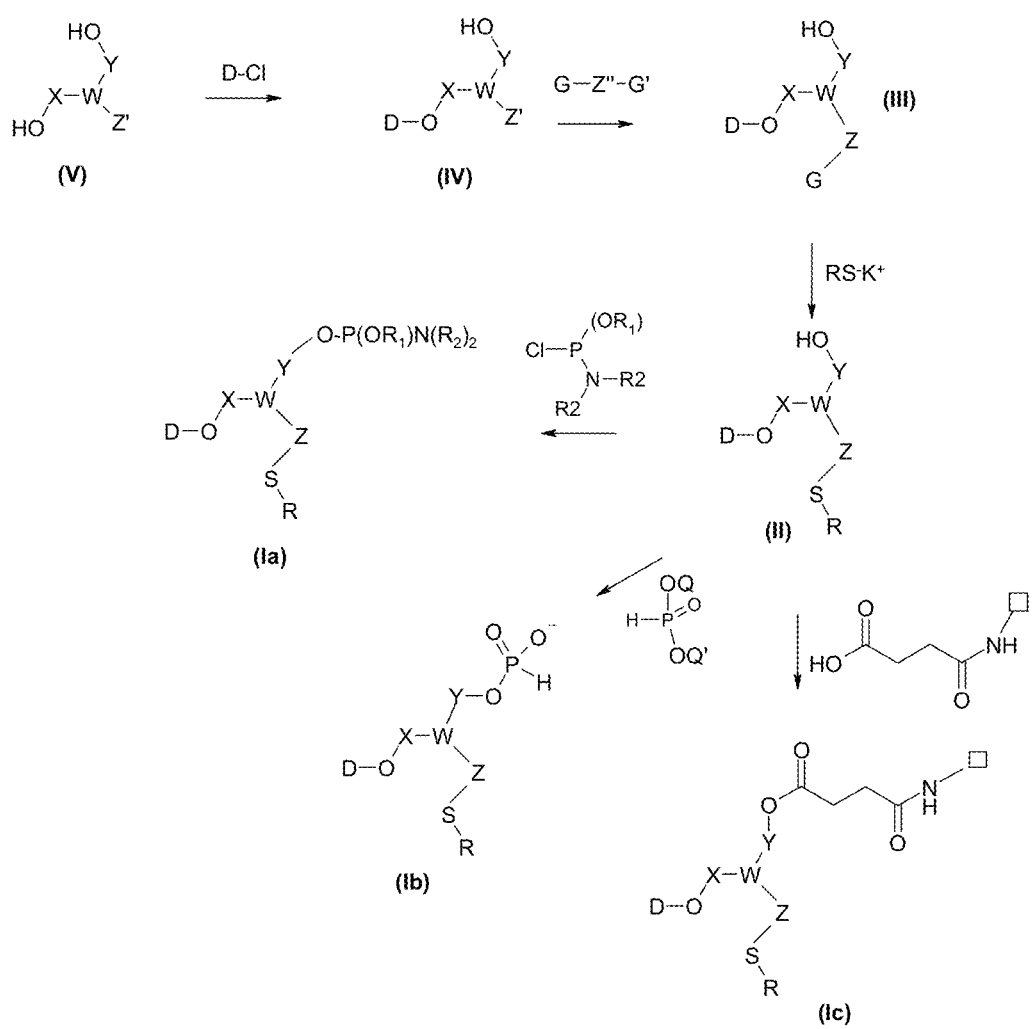
FIG. 1 shows a diagram describing a method of synthesis of compounds (I).

The present application describes the preparation of compounds of phosphoramidite, H-phosphonate structure or of compounds bound to a solid support having a protected thiol function. These thiol compounds are intended to be introduced into oligonucleotides in order to form the modified oligonucleotides according to the invention. The modified oligonucleotides thus obtained may have several thiol functions.

The present invention therefore relates to the modified oligonucleotides that can be obtained by the method described below and comprising from 2 to 12 thiol functions. The invention further relates to the use of these modified oligonucleotides for detecting at least one target nucleic acid in a biological sample.

Thiol Compound

The thiol compounds intended to be introduced into the modified oligonucleotides of the present invention correspond to the following formula (I):

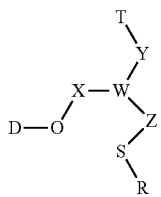

(I)

in which:
T is a group selected from —O—P(OR$_1$)N(R$_2$)$_2$, —O—PH(O)O$^-$, —OC(O)JC(O)NH—,
  R$_1$ is selected from the 2-cyanoethyl, R'$_1$R'$_2$R'$_3$SiCH$_2$CH$_2$, groups and R'$_1$, R'$_2$, R'$_3$, which may be identical or different, represent a group selected from the linear or branched alkyls comprising from 1 to 12 carbon atoms and the C6-C12 aryls,
  R$_2$ is selected from the linear or branched alkyl groups comprising from 1 to 12 carbon atoms, pyrrolidine,
  J is selected from a single bond, a —CH$_2$—, —CH$_2$CH$_2$—, —CH$_2$OCH$_2$—, —CH$_2$OPhOCH$_2$— group, where Ph is a benzyl,
□ represents a solid support,
D is a protective group of the alcohols,
W is selected from the C1-C12 alkane triyl groups, the C6-C18 aryl triyl groups and the C6-C18 aralkane triyl groups,
Z is selected from the C1-C12 alkoxy groups, oxygen-containing or nitrogen-containing C3-C12 cycloheteroalkyl groups, C1-C12 NCO-alkyl groups, C1-C12 CON-alkyl groups,
Y is selected from the linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups,
X is selected from the linear or branched C1-C12 alkyl groups, C1-C12 aminoalkyl groups, C1-C12 alkoxy groups, C3-C12 cycloalkyl groups, oxygen-containing or nitrogen-containing C3-C12 cycloheteroalkyl groups,
R is selected from the C1-C12 acyl, C1-C12 S-alkyl, C6-C12 S-aryl, S-2-pyridine, oxygen-containing or nitrogen-containing C1-C12 S-heteroalkyl, C3-C12 S-cycloalkyl, oxygen-containing or nitrogen-containing C3-C12 S-cycloheteroalkyl groups.

Within the meaning of the present invention, by "alkane triyl" is meant the linear, branched or cyclic alkane triyls, optionally substituted with one or more alkyl groups. Among the aryl triyl groups that may be present in the compound according to the invention, there may be mentioned benzene triyl and naphthalene triyl. Among the aralkane groups, there may be mentioned 1,3,5-trimethylbenzene triyl and trimethylnaphthalene triyl.

Compound (I) may be divided into three sub-compounds (Ia), (Ib) and (Ic) corresponding to the following formulae (Ia), (Ib) and (Ic), in which the parameters X, Y, Z, R, R$_1$, R$_2$ and D have the same definition as presented above for formula (I):

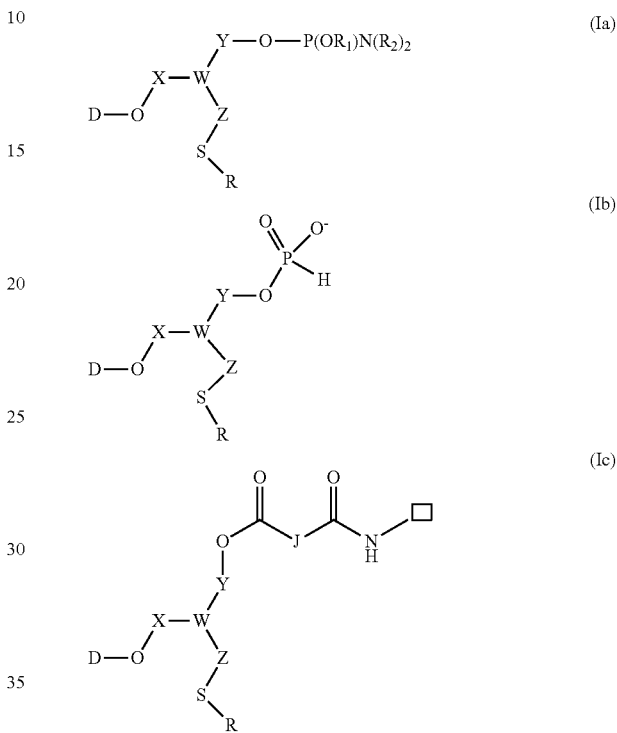

Preferably, R$_1$ is selected from the 2-cyanoethyl and R'$_1$R'$_2$R'$_3$SiCH$_2$CH$_2$ groups, and R'$_1$, R'2, R'3, which may be identical or different, represent a group selected from the linear or branched alkyl groups comprising from 1 to 6 carbon atoms, and phenyl; preferably R$_1$ is selected from the 2-cyanoethyl and R'$_1$R'$_2$R'$_3$SiCH$_2$CH$_2$ groups, and R'$_1$, R'$_2$, R'3, which may be identical or different, represent a group selected from the linear or branched alkyl groups comprising from 1 to 3 carbon atoms, and phenyl; even more preferably R$_1$ is selected from the 2-cyanoethyl, 2-(trimethylsilyl)ethyl, 2-(triphenylsilyl)ethyl, 2-(diphenylmethylsilyl)ethyl groups.

Preferably, R$_2$ is selected from the linear or branched alkyl groups comprising from 1 to 6 carbon atoms. Preferably, R$_2$ is an isopropyl group (iPr).

Preferably, the solid support □ is selected from the resins, in particular from the resins based on polystyrene, polyacrylamide, polyethylene glycol, cellulose, polyethylene, polyester, latex, polyamide, polydimethylacrylamide, synthetic or natural hydrophilic polymers, glass beads, silica gels.

Preferably, W is selected from the C1-C6 alkane triyl groups, a C6-C12 aryl triyl group, a C6-C12 aralkane triyl group, more particularly from the CH, CCH$_3$, CCH$_2$CH$_3$, the cyclohexane triyl and the benzene triyl groups.

Preferably, D is selected from the protective groups of the alcohols that allow orthogonal deprotection with respect to the other groups of compound (I). More particularly, D is selected from 4,4'-dimethoxytrityl (DMTr), 9-phenylxanthen-9-yl (pixyl) or fluorenylmethoxycarbonyl (Fmoc). The pixyl protective group is described in particular in the document Chattopadhyaya and Reese, Chem. Soc. Chem. Comm., 1978, 639-640. Another possible protective group of the alcohols is a tert-butyl-dimethylsilyl group, and in this case a polystyrene support will be particularly preferred.

Preferably, Z is selected from the C1-C6 aminoalkyl, C1-C6 alkoxy, oxygen-containing or nitrogen-containing C3-C6 cycloheteroalkyl, C1-C6 NCO-alkyl, C1-C6 CON-alkyl groups.

Preferably, Y is selected from the linear or branched C1-C6 alkyl groups, C1-C6 aminoalkyl, C1-C6 alkoxy, C3-C6 cycloalkyl, oxygen-containing or nitrogen-containing C3-C6 cycloheteroalkyl groups.

Preferably, X is selected from the linear or branched C1-C6 alkyl groups, C1-C6 aminoalkyl, C1-C6 alkoxy, C3-C6 cycloalkyl, oxygen-containing or nitrogen-containing C3-C6 cycloheteroalkyl groups.

Preferably, R is selected from the C1-C12 acyl, C1-C6 S-alkyl, C6 S-aryl, oxygen-containing or nitrogen-containing C6 S-heteroalkyl, C6 S-cycloalkyl, oxygen-containing or nitrogen-containing C6 S-cycloheteroalkyl groups.

According to an embodiment, the linear or branched alkyls are selected from the methyl, ethyl, propyl, butyl, pentyl, hexyl, heptyl, octyl, nonyl, decyl, undecyl, dodecyl, isopropyl, isobutyl, tert-butyl groups.

According to an embodiment, the aminoalkyls are selected from the aminomethyl, aminoethyl, aminopropyl, aminobutyl, aminopentyl, aminohexyl, aminoheptyl, aminooctyl, aminononyl, aminodecyl, aminoundecyl, aminododecyl, aminoisopropyl, aminoisobutyl, amino-tert-butyl groups comprising one or more nitrogen atoms. According to an embodiment, the alkoxys are selected from the methoxy, ethoxy, propyloxy, oxybutyloxy, pentyloxy, hexyloxy, heptyloxy, octyloxy, nonyloxy, decyloxy, undecyloxy, dodecyloxy, isopropyloxy, isobutyloxy, tert-butyloxy groups comprising one or more oxygen atoms.

According to an embodiment, the cycloalkyls are selected from the rings, optionally comprising one or more unsaturations, comprising between 3 and 12 carbon atoms, preferably 6 carbon atoms.

According to an embodiment, the cycloheteroalkyls are selected from the rings substituted with one or more nitrogen and/or oxygen atoms, optionally comprising one or more unsaturations and comprising between 3 and 12 carbon atoms, preferably 5 carbon atoms and one nitrogen or oxygen atom.

According to an embodiment, the NCO-alkyls and CON-alkyls are groups in which the alkyls may be linear or branched alkyls selected from methyl, ethyl, propyl, butyl, pentyl, hexyl, heptyl, octyl, nonyl, decyl, undecyl, dodecyl, isopropyl, isobutyl, tert-butyl groups.

According to an embodiment, $R_2$ is an isopropyl group (iPr) and/or $R_1$ is a cyanoethyl group.

According to a preferred embodiment, the thiol compound (Ia) is compound (VI) corresponding to the following formula:

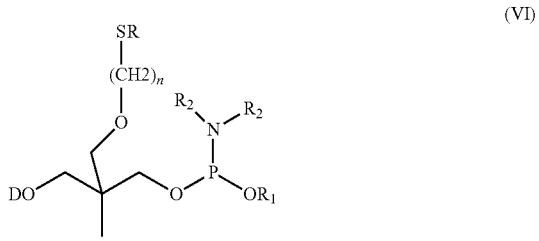

(VI)

in which, n is an integer between 1 and 12, preferably between 1 and 6,

R, $R_1$, $R_2$ and D have the same definition as above for (Ia).

Preferably, $R_2$ is an isopropyl group (iPr) and $R_1$ is a cyanoethyl group.

Preferably, R is an acetyl group.

Preferably, D is 4,4'-dimethoxytrityl.

According to another embodiment, the thiol compound (Ia) is compound (VII) corresponding to the following formula:

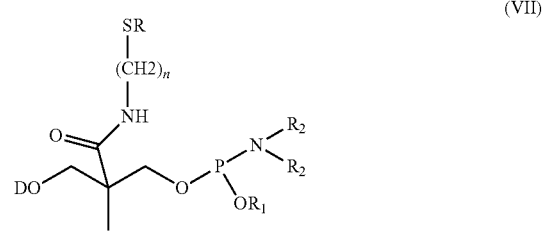

(VII)

in which, n is an integer between 1 and 12, preferably between 1 and 6,

R, $R_1$, $R_2$ and D have the same definition as above for (Ia).

Preferably, $R_2$ is an isopropyl group (iPr) and $R_1$ is a cyanoethyl group.

Preferably, R is an acetyl group.

Preferably, D is 4,4'-dimethoxytrityl.

According to an embodiment, the thiol compound (Ic) is compound (VIII) corresponding to the following formula:

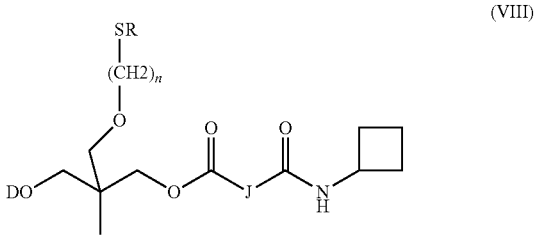

(VIII)

in which, n is an integer between 1 and 12, preferably between 1 and 6,

R and ☐ have the same definition as above for (Ic).

Preferably, R is an acetyl group. Preferably, J is an ethyl group. Preferably, D is 4,4'-dimethoxytrityl.

According to an embodiment, the thiol compound (Ia) is compound (IX) of formula:

(IX)

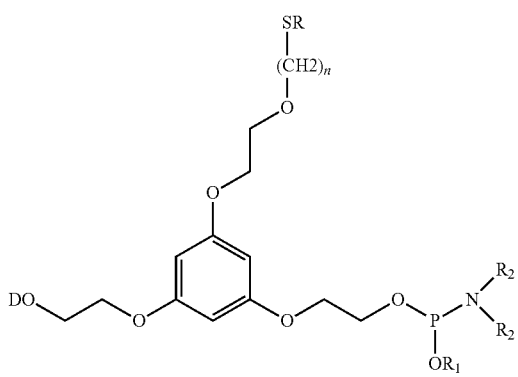

in which, n is an integer between 1 and 12, preferably between 1 and 6,

R, $R_1$, $R_2$ and D have the same definition as above for (Ia).

Preferably, $R_2$ is an isopropyl group (iPr) and $R_1$ is a cyanoethyl group.

Preferably, R is an acetyl group.

Preferably, D is 4,4'-dimethoxytrityl.

According to an embodiment, the thiol compound (Ia) is compound (X) of formula:

(X)

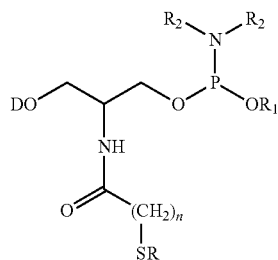

in which, n is an integer between 1 and 12, preferably between 1 and 6,

R, $R_1$, $R_2$ and D have the same definition as above for (Ia).

Preferably, $R_2$ is an isopropyl group (iPr) and $R_1$ is a cyanoethyl group.

Preferably, R is an acetyl group.

Preferably, D is 4,4'-dimethoxytrityl.

Preferably, $R_2$ is an isopropyl group (iPr) and $R_1$ is a cyanoethyl group.

According to an embodiment, the thiol compound (Ia) is compound (XI) of formula:

(XI)

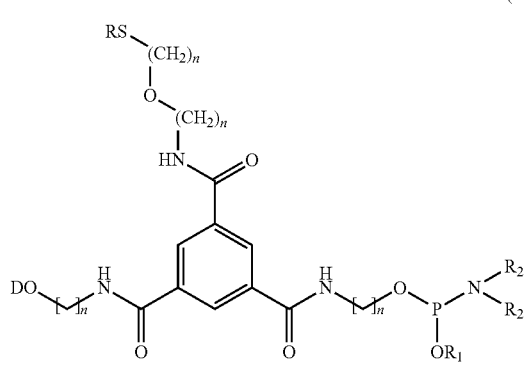

in which, n is an integer between 1 and 12, preferably between 1 and 6,

R, $R_1$, $R_2$ and D have the same definition as above for (Ia).

Preferably, $R_2$ is an isopropyl group (iPr) and $R_1$ is a cyanoethyl group.

Preferably, R is an acetyl group.

Preferably, D is 4,4'-dimethoxytrityl.

Manufacturing Process

The manufacturing process of compounds (Ia), (Ib) and (Ic) is represented in the diagram in FIG. 1.

Compounds (Ia), (Ib) and (Ic) are obtained from the same compound (II) having the following formula:

(II)

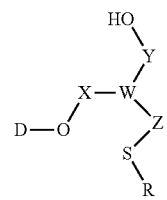

in which D, X, W, Y, Z and R have the same definition as in the thiol compound (I).

The compound of formula (Ia) may be obtained by the reaction represented in the following diagram:

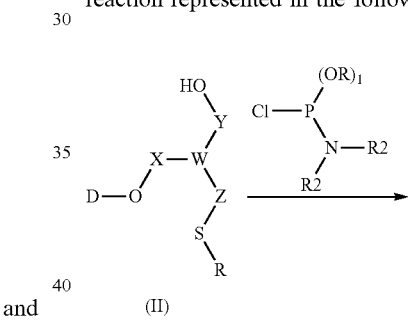

(II)

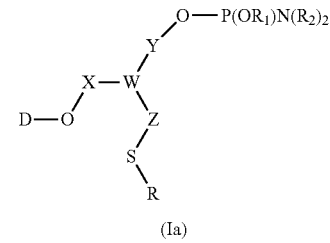

(Ia)

or by the reaction represented in the following diagram, preferably in the presence of the salt of diisopropylamine tetrazolide:

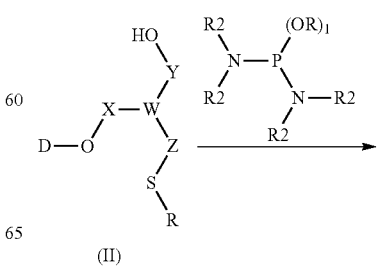

(II)

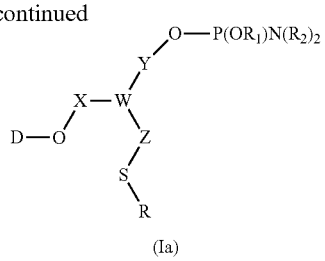

(Ia)

The compound of formula (Ib) may be obtained by the reaction represented in the following diagram:

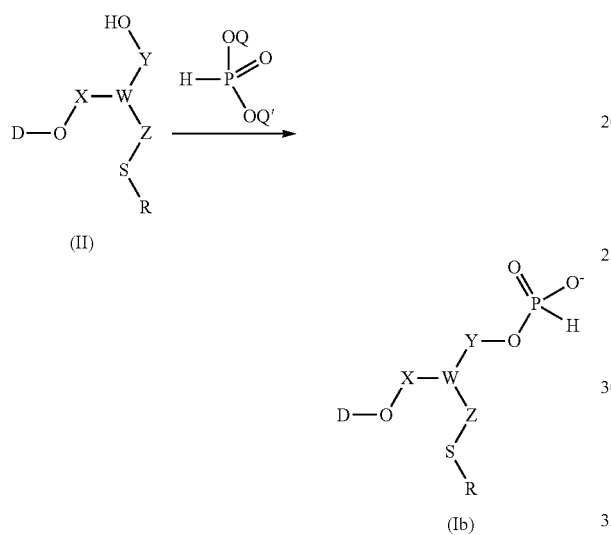

(Ib)

in which Q and Q' represent, independently of one another, a substituted or unsubstituted benzene group.

The foregoing reaction for obtaining compound (Ia) or (Ib) is carried out starting from compound (II), preferably in the presence of a base, for example diisopropylethylamine (DIEA), in an anhydrous solvent, such as anhydrous dichloromethane.

The compound of formula (Ic) is also obtained from compound (II) but preferably according to the reaction step represented in the following diagram:

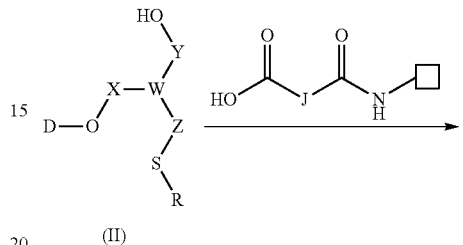

(II)

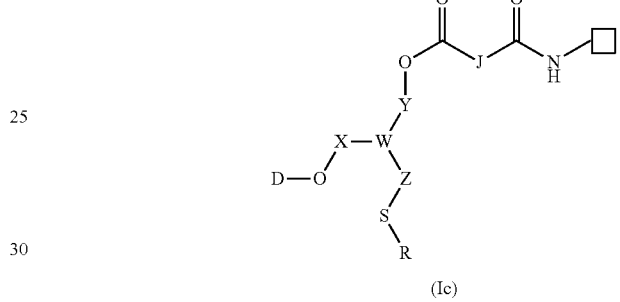

(Ic)

The preceding reaction for obtaining compound (Ic) is preferably carried out in an anhydrous solvent, such as pyridine, in the presence of a base, such as triethylamine.

It is also possible to obtain compound (Ic) according to the following reaction diagram:

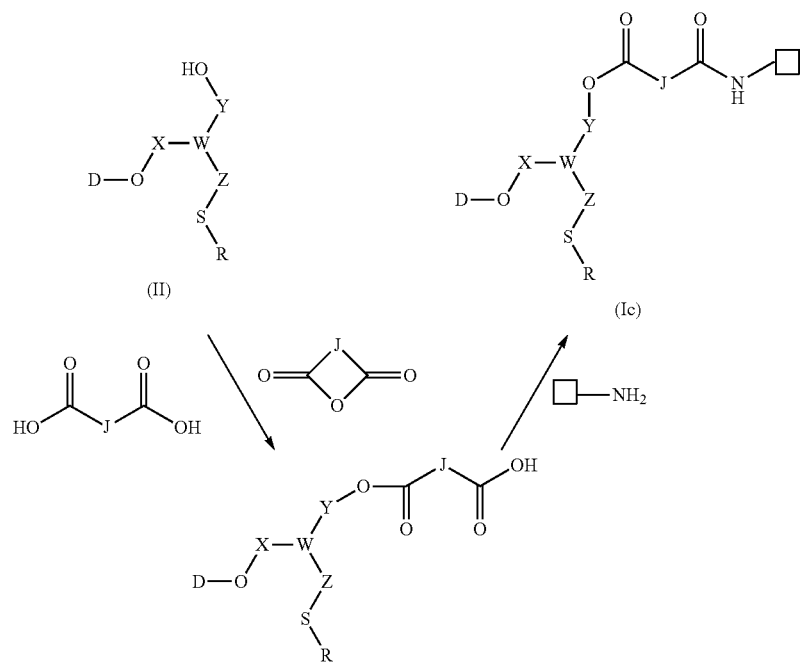

Compound (II) of the above formula, in which the X, W, Z, Y and R groups have the same definition as in compound (I), corresponds to one embodiment.

The compound of formula (II) may be obtained from compound (III) according to the reaction step described below:
[Insert Diagram]
in which G is a halogen, preferably bromine or iodine.

The reaction described above is preferably carried out in an anhydrous solvent, such as anhydrous toluene and in the presence of a crown ether.

Compound (III) may be obtained from compound (IV) according to the reaction step described below:

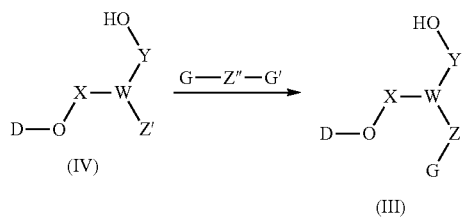

in which,

G and G' are halogen atoms, which may be identical or different, preferably G and G' are bromine or iodine atoms, Z' is a C1-C12 aminoalkyl, C1-C12 alkoxy, oxygen-containing or nitrogen-containing C3-C12 cycloheteroalkyl, C1-C12 NCO-alkyl, C1-C12 CON-alkyl group, Z" is a C1-C12 linear or branched alkyl, C1-C12 aminoalkyl, C1-C12 alkoxy, C3-C12 cycloalkyl, oxygen-containing or nitrogen-containing C3-C12 cycloheteroalkyl, C1-C12 NCO-alkyl, C1-C12 CON-alkyl group, the dihalogenated compound G-Z"-G' being intended to react with the Z' group of compound (IV) to lead to the formation of the Z-G group of compound (III).

The step of obtaining compound (III) is preferably carried out in the presence of an alkali hydride, such as NaH.

Compound (IV) may be obtained from the commercial compound (V) by protection of the alcohol function, according to the following reaction step:

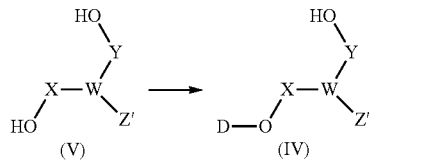

This step of protection of the alcohol function is carried out under conditions well known to a person skilled in the art, depending on the choice of D.

According to an embodiment, compound (IV) is obtained from compound (V) by reaction with 4,4'-dimethoxytrityl chloride (DMTr-Cl) preferably in a solvent, such as pyridine in order to protect the alcohol function.

According to another embodiment, compound (IV) is obtained from compound (V) starting from 9-phenylxanthen-9-yl chloride (pixyl-Cl) under the conditions described in the document Chattopadhyaya and Reese, Chem. Soc. Chem. Comm., 1978, 639-640.

According to another embodiment, compound (IV) is obtained from compound (V) by reaction with fluorenyl-methoxycarbonyl chloride (Fmoc-Cl) under conditions well known to a person skilled in the art.

In the above formulae (II) to (V), X, Y, W, Z, D, R, $R_1$, $R_2$ have the same definitions as in the definition of compound (I) given above.

Preferably, the starting compound (V) is 1,1,1-tris(hydroxymethyl)ethane or 2,2-bis(hydroxymethyl)propionic acid or 1,3,5-tris(hydroxyethoxy)benzene or 1,3,5-tris(hydroxymethyl)cyclohexane or 2-amino-1,3-propanediol.

Oligomer of the Thiol Compound

Figure 2A:
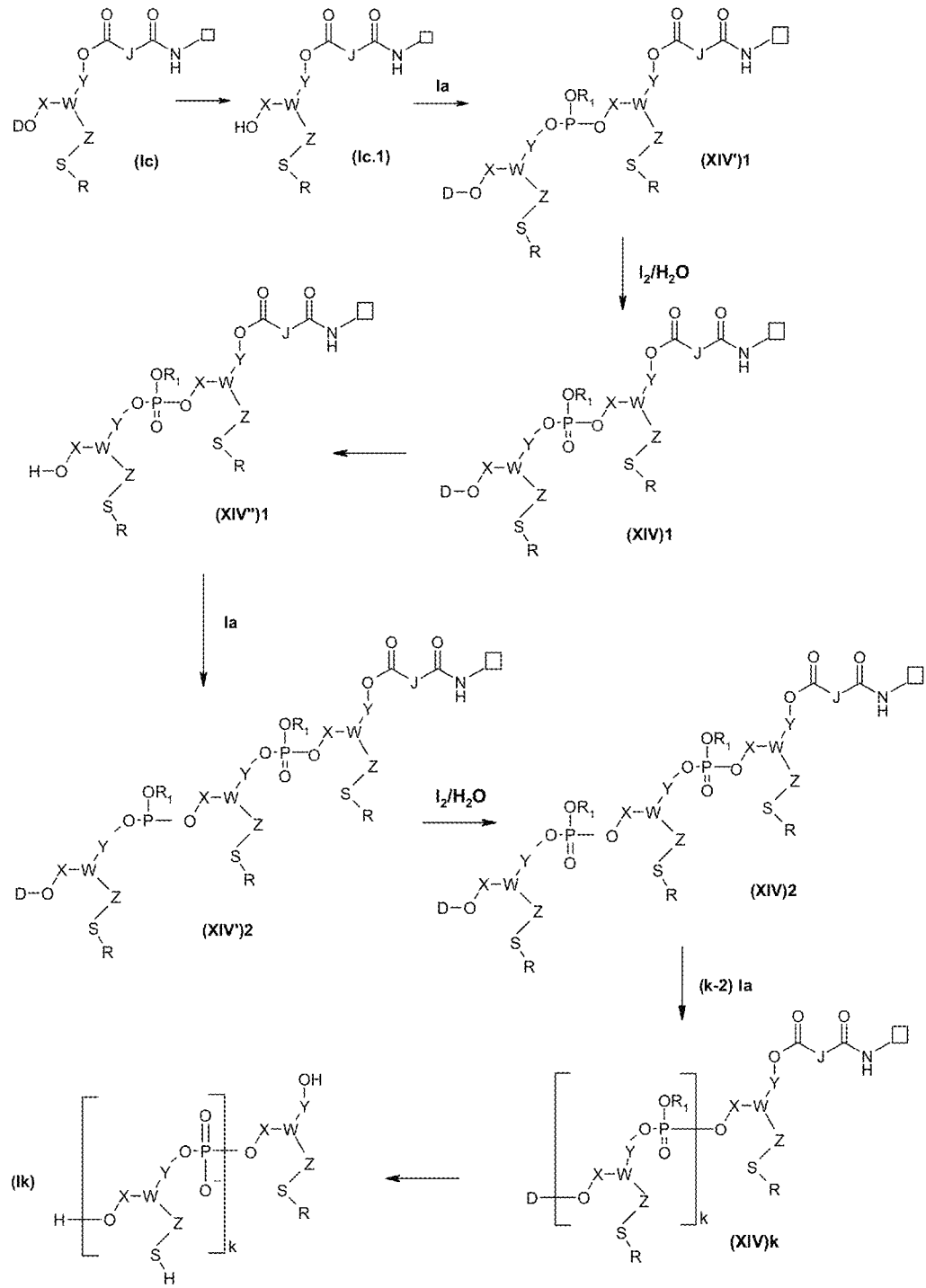
FIGS. 2A and 2B show, respectively, a diagram describing a method of synthesis of an oligomer of the compounds of the invention starting from compounds (Ia) and starting from compounds (Ib).
Figure 2B:
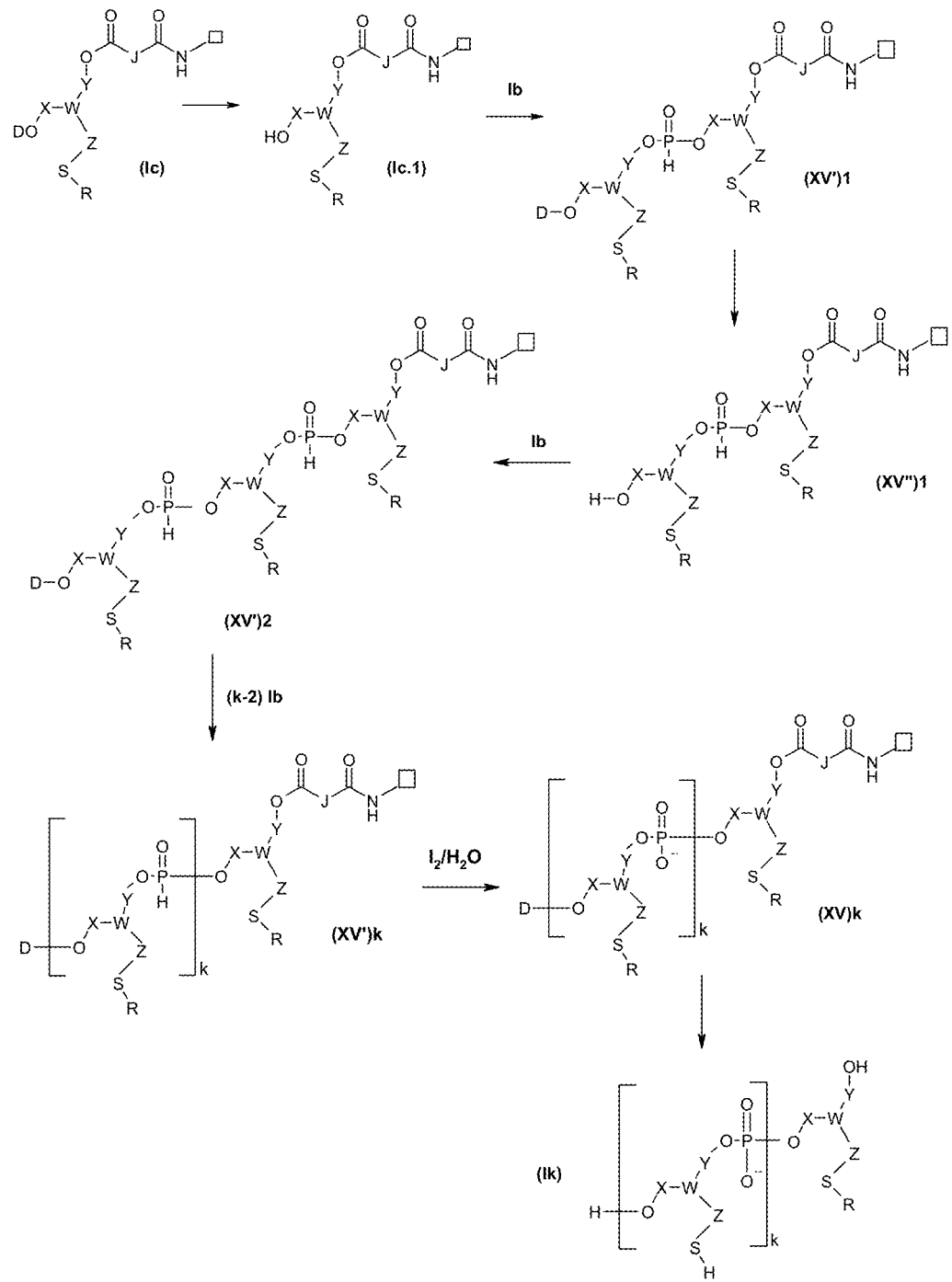

An oligomer may be formed from thiol compounds of formula (I) described above. The method of synthesis of these oligomers is described in the diagram in FIG. 2A for the oligomerization of compounds of formula (Ia) and in the diagram in FIG. 2B for the oligomerization of compounds of formula (Ib).

In a first step, the alcohol function of compound (Ic) is deprotected in order to lead to compound (Ic.1). This deprotection step is carried out by means that are well known to a person skilled in the art, preferably in the presence of di- or trichloroacetic acid for the groups DMTr and Pixyl and of piperidine for the Fmoc group.

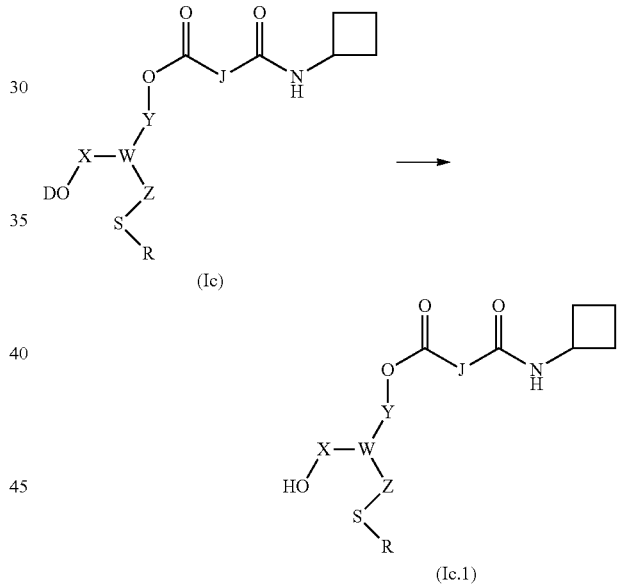

Then, compound (Ic.1) reacts with compound (Ia) or (Ib), leading respectively to the compound phosphite triester (XIV')1 or H-phosphonate diester (XV')1.

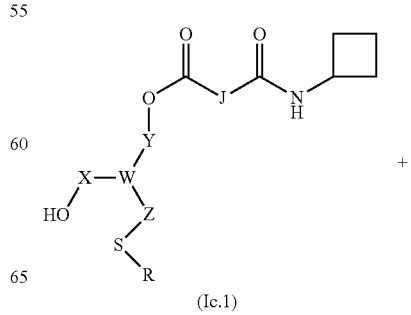

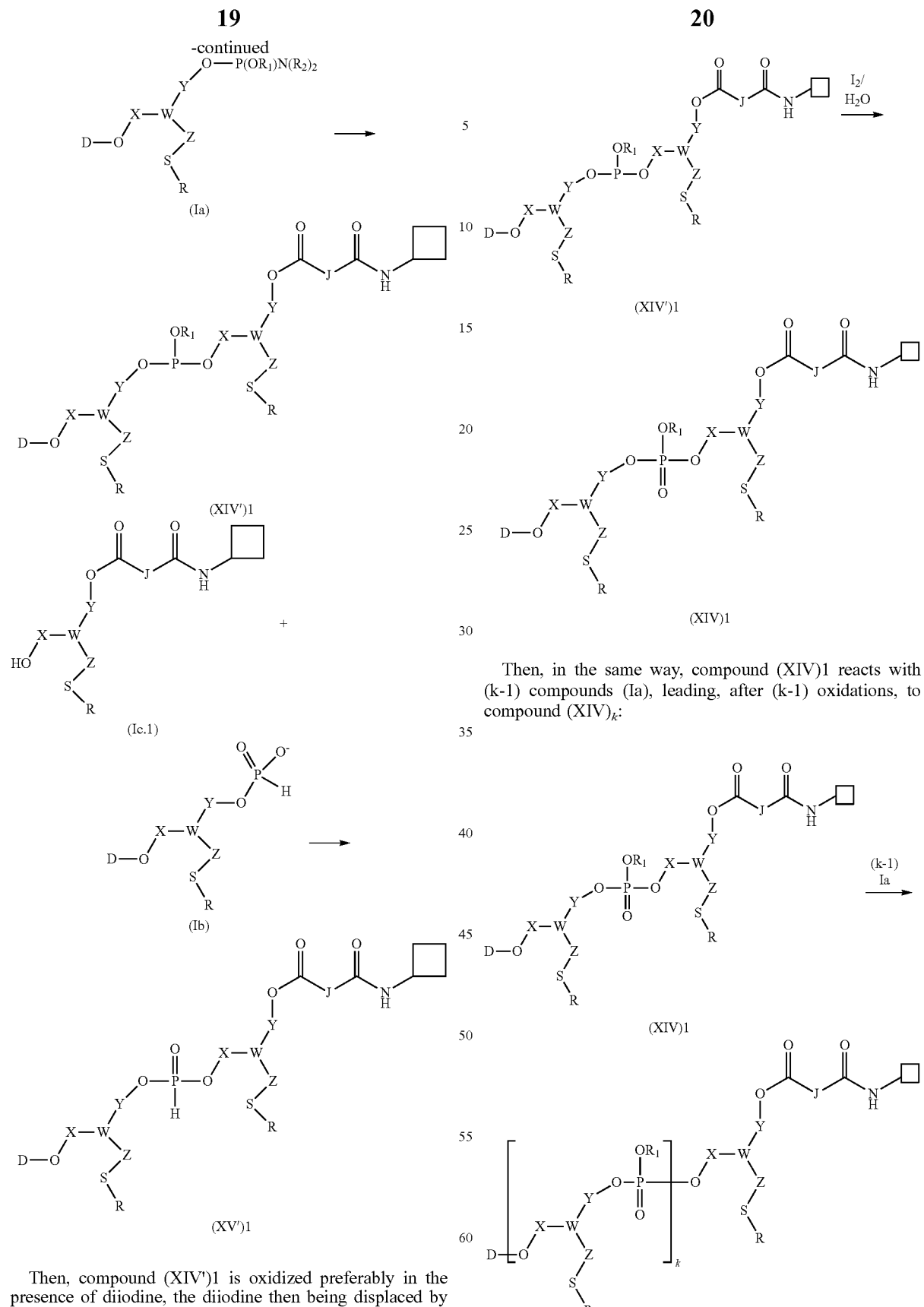

Then, compound (XIV')1 is oxidized preferably in the presence of diiodine, the diiodine then being displaced by water supplying the oxygen atom of the phosphate triester bond, leading to the phosphotriester compound (XIV)1. This oxidation step is carried out after each coupling step between a compound (XIV)i and a compound (Ia).

Then, in the same way, compound (XIV)1 reacts with (k-1) compounds (Ia), leading, after (k-1) oxidations, to compound $(XIV)_k$:

and compound (XV')1 is deprotected on its alcohol function to give (XV")1, which reacts with (k-1) compounds (Ib), leading to compound (XV')$_k$:

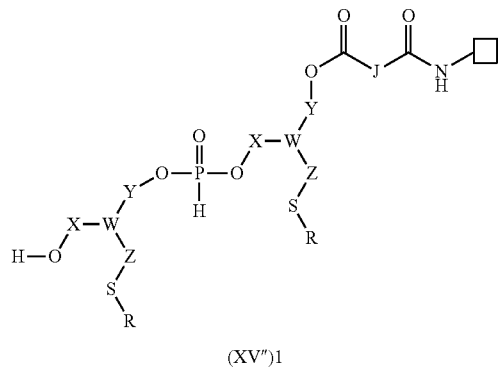

(XV")1

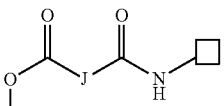

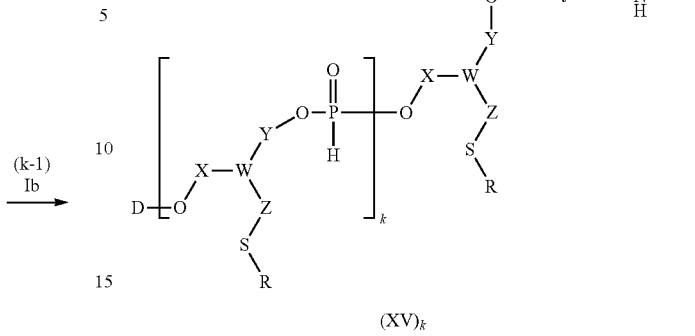

(XV)$_k$

Finally, an optional last step consists of deprotecting compounds (XIV)$_k$ or (XV)$_k$, leading to the same compound (I)$_k$.

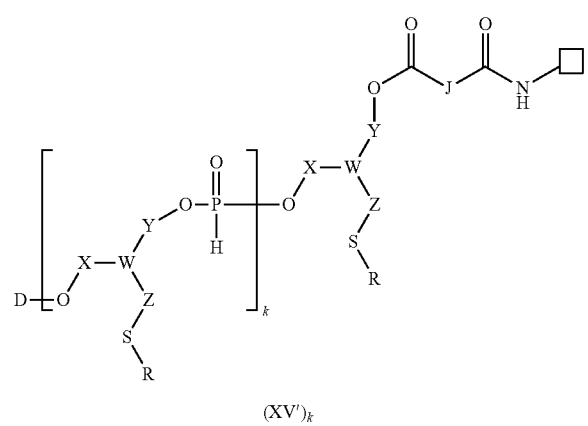

(XV')$_k$

Then, compound (XV')$_k$ is oxidized, preferably in the presence of diiodine and water, leading to the phosphodiester compound (XV)$_k$.

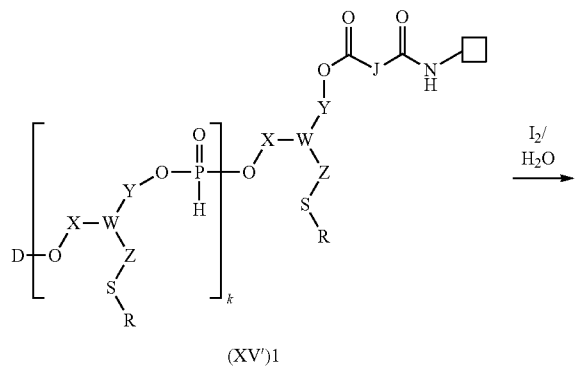

(XV')1

Preferably, the oligomer results from the oligomerization of 2 to 12 compounds (I), in particular between 2 and 8 compounds (I), i.e. the oligomer may comprise 2, 3, 4, 5, 6, 7 or 8 compounds (I). Preferably, the thiol oligomer intended to be grafted on a gold surface comprises between 3 and 8, advantageously between 4 and 8 compounds (I) and the thiol oligomer intended for conjugation with a surface comprising at least one carbon-carbon double bond or carbon-carbon triple bond or haloacetamide functions, preferably maleimide or acrylamide functions, advantageously comprises between 2 and 6 compounds (I).

According to an embodiment, the oligomer is produced solely from compounds of formula (Ia) or from compounds of formula (Ib). The oligomerization is carried out by reaction between the deprotected alcohol function of a first compound (I) and the phosphoramidite or H-phosphonate function of a second compound (I).

It is also possible to envisage production of an oligomer starting from a mixture of compounds (Ia) and of compounds (Ib), this embodiment being of less interest.

Preferably, the oligomer is produced utilizing phosphoramidite chemistry, i.e. by oligomerization of compounds of type (Ia).

The oligomerization may be carried out on a solid support or in solution. Preferably, oligomerization is carried out on a solid support. In fact, oligomerization in solution involves steps of purification by chromatography, steps that are not economically viable, especially for the small quantities required in diagnostic applications.

The solid support grafted with an oligomer of a compound (Ia) or of a compound (Ib) corresponds to the following formula $(XVI)_k$:

(Ic)-(I')$_k$  $(XVI)_k$ in which:

k represents an integer between 1 and 11, (Ic) has the same meaning as above, (I') represents (I'a) or (I'b), with:

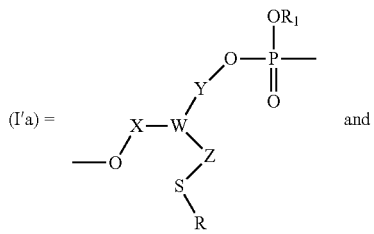

and

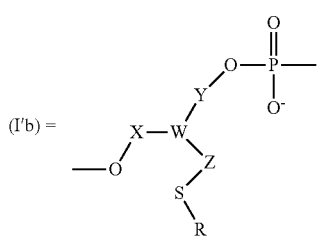

The oligomer on a solid support formed from a compound (Ic) and from compounds of formula (Ia) corresponds to the following formula $(XIV)_k$:

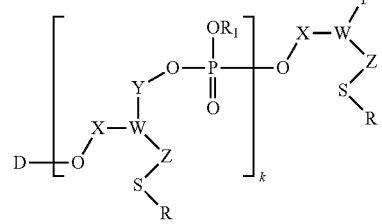

in which D, X, Y, W, Z, J, R and $R_1$ have the same definition as above and R may in addition represent H; k is an integer between 1 and 11.

The oligomer on a solid support formed from a compound (Ic) and from compounds of formula (Ib) corresponds to the following formula $(XV)_k$:

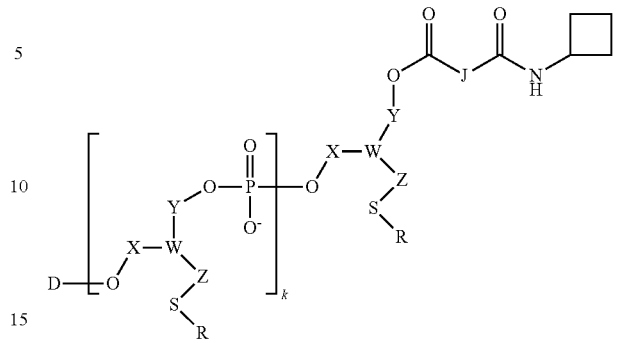

in which D, X, Y, W, Z, J and R have the same definition as above and R may in addition represent H; k is an integer between 1 and 11.

In the case when the oligomer is formed on a solid support starting from a compound (Ic) and from compounds (Ib), the compound obtained $(XV)_k$ corresponds to the same formula as compound $(XIV)_k$ but in which $R_1$ is a hydrogen atom after oxidation of the H-phosphonate diester bonds.

At the end of the oligomerization reaction, deprotection of the thiol functions by conventional methods may be envisaged and then R represents H.

Modified Oligonucleotides

A subject of the present invention relates to a modified oligonucleotide, comprising at least ten nucleotides and at least two thiol compounds (I) as described above.

In the present application, the term oligonucleotide denotes a chain comprising from 4 to 100 nucleotides.

The thiol compound according to the invention is grafted in position 3', in the chain, or in position 5' of an oligonucleotide.

The preparation process for said modified oligonucleotide comprises at least:

a step of grafting a compound (I) on an oligonucleotide to give a 5'-thiol oligonucleotide, or a step of grafting a nucleotide on an oligomer of a compound (I) to give a 3'-thiol oligonucleotide.

According to an embodiment, the grafted oligonucleotide corresponds to the following formula (XIIa):

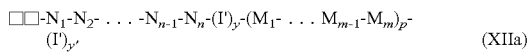

in which, $N_1, \ldots N_n$ represent, independently of one another, a nucleotide, $M_1, \ldots M_m$ represent, independently of one another, a nucleotide, (I') represents a compound of formula (I'a) or (I'b), n is an integer ranging from 4 to 100, m is an integer ranging from 4 to 100, y is an integer ranging from 2 to 12, p represents 0 or 1, y' is an integer ranging from 0 to 12 if p has the value 1, and y' is equal to 0 if p has the value 0, the sum of the integers (y+y') not being greater than 12, ☐ represents a solid support.

The modified oligonucleotide (XIIa) has two or more thiol compounds in position 5' of an oligonucleotide N or in the nucleotide chain. It is obtained by grafting a compound (I) followed by elongation of the oligomer obtained from (I) in position 5' of an oligonucleotide. Then, in the case when p=1, elongation of the nucleotide chain continues. Then, in the same way, grafting of one or more additional compounds (I) in position 5' of the oligonucleotide M may be envisaged.

Figure 3:
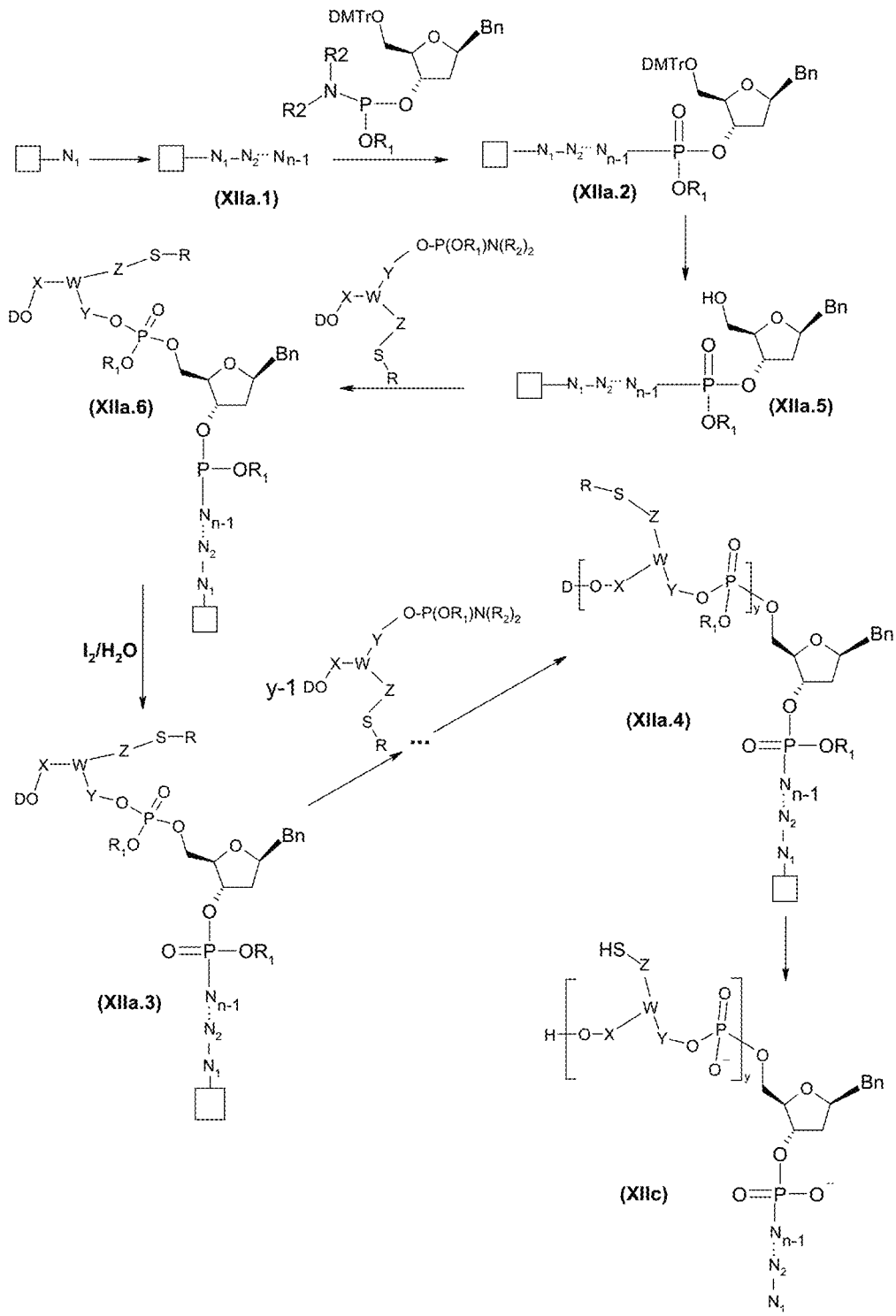
FIG. 3 shows a diagram describing a method of synthesis of an oligonucleotide compound (XIIc) grafted with an oligomer of (I) at its 5' end.

A diagram for obtaining compound (XIIa) is described in FIG. 3, in which the thiol compounds are of type (Ia) and p is equal to 0. The first three steps in the preparation of compound (XIIa) allow synthesis of an oligonucleotide. The oligonucleotide is synthesized on a solid support by a conventional method well known to a person skilled in the art. In the first step, a first nucleotide is grafted on a solid support, then the other nucleotides are grafted by synthesis methods well known to a person skilled in the art. The following compound is obtained:

 (XIIa.1)

Then another nucleotide is grafted by an identical method, leading to the compound of formula (XIIa.2).

In the next step, a thiol compound as described above, of type (Ia), is grafted in position 5' of the oligonucleotide (XIIa.2), leading to compound (XIIa.3):

 (XIIa.3)

In this step, grafting is carried out conventionally by reaction of the phosphoramidite function of compound (Ia) with the alcohol function in position 5' of the terminal nucleotide of compound (XIIa.2).

In the diagram in FIG. 3, a synthesis example is described with the oligomerization of the thiol compound of type (Ia); a similar synthesis method is used for the synthesis of oligonucleotides modified with thiol compounds of type (Ib).

Then, the oligomerization as described previously, in particular in FIGS. 2A and 2B, takes place starting from compound (XIIa.3) above, by reaction with one or more compounds (Ia) or (Ib), leading to compound (XIIa.4) of formula:

□□-$N_1$-$N_2$- . . . -$N_{n-1}$-$N_n$(I'a)$_y$ or as a structural formula (in the case when p=0):

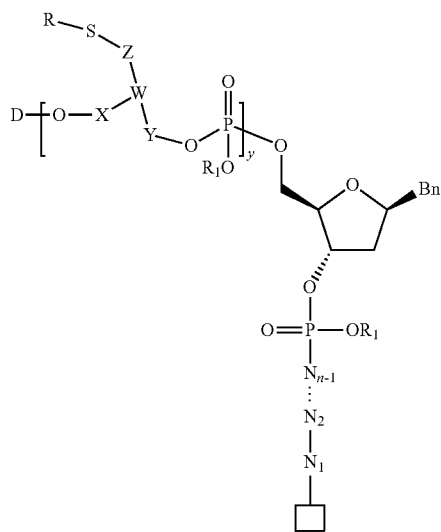 (XIIa.4)

in which,

D, R, X, Y, W, Z, $R_1$ have the same definition as for compound (I) and $R_1$ may in addition represent H, n, y and $N_1$, $N_2$, . . . $N_{n-1}$ have the same definition as for compound (XIIa), Bn represents a base used conventionally in a nucleotide chain.

In the case when elongation of the oligomer is carried out with compounds of type (Ib), the modified oligonucleotide has a structure similar to that of the modified oligonucleotide (XIIa.4) but in which $R_1$ represents H.

Subsequent grafting of nucleotide compounds $M_1$, $M_2$, . . . $M_m$ is then possible, leading to the product (XIIa) with p=1. In these cases, elongation also takes place on a solid support.

This grafting step is carried out conventionally by methods known to a person skilled in the art.

According to another embodiment, the grafted oligonucleotide corresponds to the following formula (XIIIa):

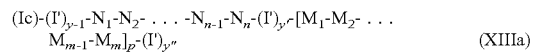 (XIIIa)

in which, $N_1$, . . . $N_n$ represent, independently of one another, a nucleotide, $M_1$, $M_m$ represent, independently of one another, a nucleotide, (I') represents a compound of formula (I'a) or (I'b), n is an integer ranging from 4 to 100, m is an integer ranging from 4 to 100, y is an integer ranging from 2 to 12, y' is an integer ranging from 2 to 12, p has the value 0 or 1 if y' is different from 0, and if y' has the value 0 then p has the value 0, y" is an integer ranging from 0 to 12 if p has the value 1, and if p has the value 0 then y" has the value 0, the sum of the integers (y+y'+y") not being greater than 12.

Figure 4:
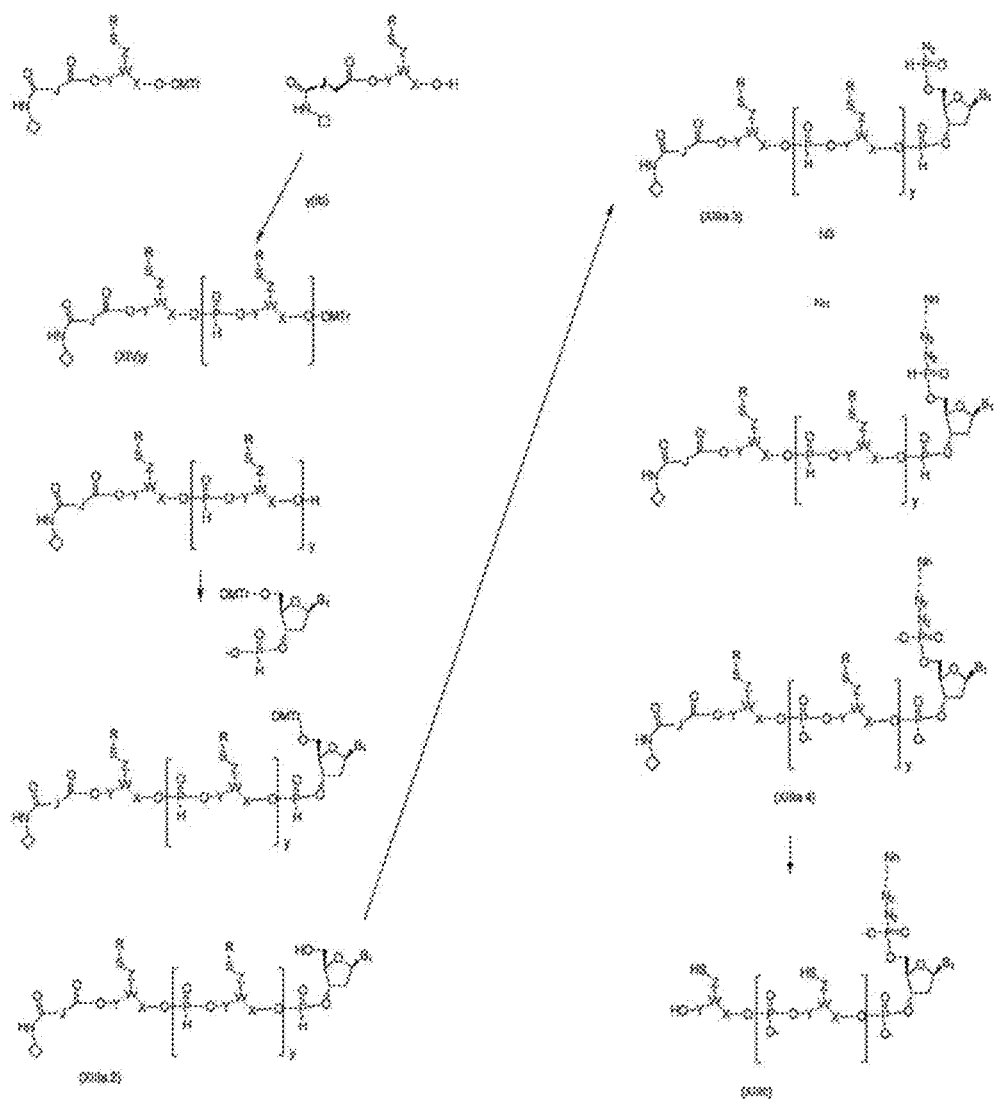
FIG. 4 shows a diagram presenting a method of synthesis of an oligonucleotide compound (XIIIc) grafted with an oligomer of (I) at its 3' end.

A diagram representing a synthesis method of compound (XIIIc) is described in FIG. 4 using an oligomer formed from a compound of type (Ic) where J is an ethyl group, and compounds of type (Ib).

Synthesis of the compound of formula (XIIIc) comprises a first step consisting of the oligomerization of the thiol compound according to the invention of formula (I), the method for which is described above, leading to the compound of formula (XIIIa.1):

 (XIIIa.1)

in which, (Ic) has the same definition as before, (I') represents a group of type (I'a) or (I"b), where

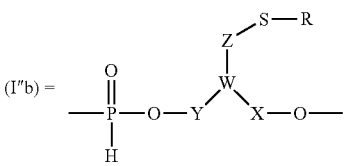

or as a structural formula in the case when (I') represents (I"b):

(XV')$_y$

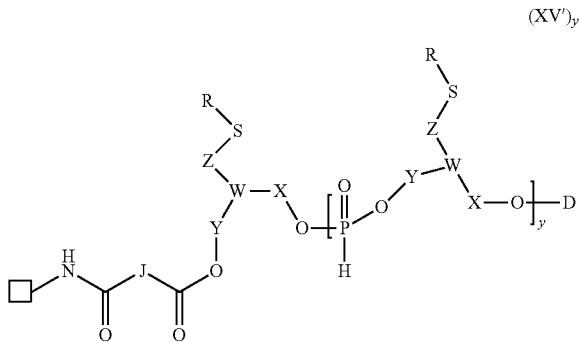

In a second step, a first nucleotide $N_1$ is grafted on the oligomer of formula (XIIIa.1), leading to the compound of the following formula (XIIIa.2):

$$(Ic)\text{-}(I')_{y-1}\text{-}N_1 \tag{XIIIa.2}$$

This grafting step is carried out by reaction between the deprotected alcohol function at the end of the oligomer chain of compound (XIIIa.1) and the phosphoramidite or H-phosphonate function of the first nucleotide $N_1$.

The modified oligonucleotide is then synthesized by any method known to a person skilled in the art, in particular a conventional method well known to a person skilled in the art by reaction between the alcohol function at 5' of the first nucleotide present on the oligomer of the thiol compound and the phosphoramidite or H-phosphonate function in position 3' of a second nucleotide. The synthesis continues by similar successive steps of elongation of the nucleotide chain well known to a person skilled in the art, leading to the compound of formula (XIIIa).

A subject of the present invention thus relates to the compounds obtained from the compounds of formula (XIIa) and (XIIIa) above after cleavage of the bond that attaches the modified oligonucleotide to the solid support. Bond cleavage takes place at the level of the ester function.

Thus, According to an embodiment of the invention, the unsupported modified oligonucleotide of the invention has the following structure (XIIb):

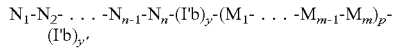

(XIIb)

in which, $N_1, \ldots N_n$ represent, independently of one another, a nucleotide, $M_1, \ldots M_m$ represent, independently of one another, a nucleotide, (I'b) represents a compound of formula as defined above, n is an integer ranging from 4 to 100, m is a number ranging from 4 to 100, y is an integer ranging from 2 to 12, p represents 0 or 1, y' is an integer ranging from 0 to 12 if p has the value 1, and y' is equal to 0 if p has the value 0, the sum of the integers (y+y') not being greater than 12.

Withdrawal of the support is carried out in two steps, firstly with a non-nucleophilic strong base (piperidine or DBU) in order to eliminate the cyanoethyl groups if present (in the case of phosphoramidites) and secondly by a conventional method known to a person skilled in the art, preferably by treatment of compound (XIIa) with ammonium hydroxide (NH$_4$OH). It is necessary to remove the cyanoethyl groups before deprotection of the thiol groups as they form acrylonitrile during their removal, which reacts strongly with the thiol functions.

According to another embodiment of the invention, the unsupported modified oligonucleotide of the invention has the following structure (XIIIb):

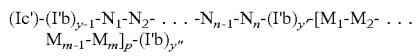

(XIIIb)

in which, $N_1, \ldots N_n$ represent, independently of one another, a nucleotide, $M_1, \ldots M_m$ represent, independently of one another, a nucleotide, (Ic') represents the compound obtained from (Ic) by cleavage of the ester bond with the solid support, and preferably has the structure

(Ic')

(I'b) represents a compound of formula as defined above, n is an integer ranging from 4 to 100, m is an integer ranging from 4 to 100, y is an integer ranging from 2 to 12, y' is an integer ranging from 0 to 12, p has the value 0 or 1 if y' is different from 0, and if y' has the value 0 then p has the value 0, y" is an integer ranging from 0 to 12 if p has the value 1, and if p has the value 0 then y" has the value 0, the sum of the integers (y+y'+y") is not greater than 12.

Withdrawal of the support is carried out by a conventional method known to a person skilled in the art, preferably by treatment of compound (XIIIa) with ammonium hydroxide (NH$_4$OH).

According to an embodiment of the present invention, in the case when p=0, the modified oligonucleotide corresponds to the structural formula (XIIb):

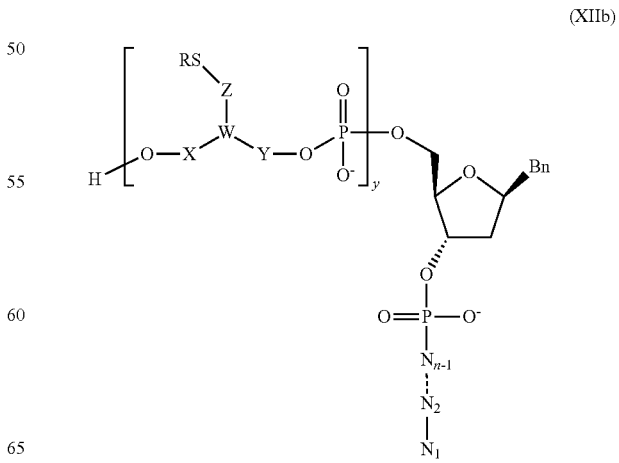

(XIIb)

in which n, y, $N_1, \ldots, N_{n-1}$, X, Y, Z, W and R have the same definition as above, and $B_n$ represents the base of the n-th nucleotide.

According to another embodiment of the present invention, in the case when p=0, the modified oligonucleotide corresponds to the structural formula (XIIIb):

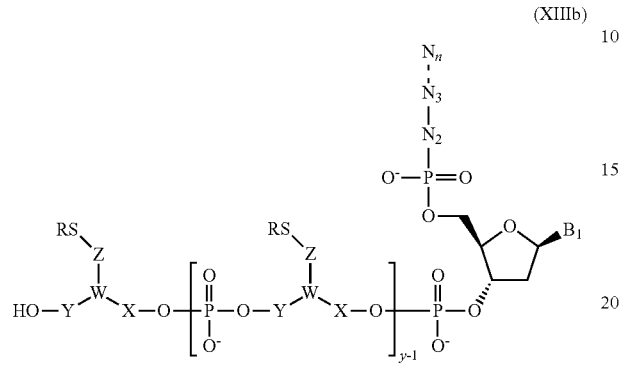

(XIIIb)

in which n, y, $N_2, \ldots, N_n$, X, Y, Z, W and R have the same definition as above, and Bi represents the base of the 1st nucleotide.

The present invention further relates to the modified oligonucleotides (XIIc) and (XIIIc) obtained respectively starting from compounds (XIIa) and (XIIIa) by deprotection of the thiol function and cleavage of the bond attaching the compound to the solid support (FIGS. 3 and 4 respectively).

In the case when the oligonucleotide is modified with one or more thiol compounds of type (Ia), after deprotection of the thiol function and of the phosphoramidite function of compound (XIIa) by a treatment known to a person skilled in the art, the compound of formula (XIIc) is obtained:

$$N_1\text{-}N_2\text{-} \ldots \text{-}N_{n-1}\text{-}N_n(I'')_{y'}\text{-}(M_1\text{-} \ldots M_{m-1}\text{-}M_m)_p\text{-}(I'')_{y'} \quad \text{(XIIc)}$$

in which, $N_1, \ldots N_n$ represent, independently of one another, a nucleotide, $M_1, \ldots M_m$ represent, independently of one another, a nucleotide,

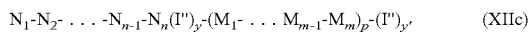

n is an integer ranging from 4 to 100,
m is an integer ranging from 4 to 100,
y is an integer ranging from 2 to 12,
p represents 0 or 1,
y' is an integer ranging from 0 to 12 if p has the value 1, and y' is equal to 0 if p has the value 0,
the sum of the integers (y+y') not being greater than 12;

or as a structural formula in the case when p=0:

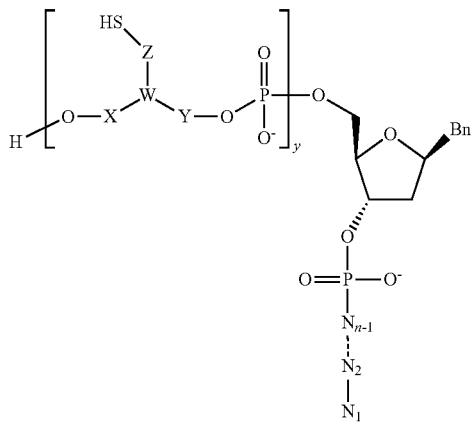

(XIIc)

in which,

X, Y, W, Z, $R_1$ have the same definition as for compound (I), $N_1, \ldots N_n$, y have the same definition as for compound (XIIa), Bn represents a base used conventionally in a nucleotide chain.

In the case when the oligonucleotide is modified with one or more thiol compounds of type (Ib), after deprotection of the thiol function of compound (XIIIa) by a treatment known to a person skilled in the art, the compound of formula (XIIIc) is obtained:

$$(\text{Ic}')\text{-}(I')_{y-1}\text{-}N_1\text{-}N_2\text{-} \ldots \text{-}N_{n-1}\text{-}N_n\text{-}(I'')_{y'}\text{-}[M_1\text{-}M_2\text{-} \ldots \text{-}M_{m-1}\text{-}M_m]_p\text{-}(I'')_{y''} \quad \text{(XIIIc)}$$

in which, $N_1, \ldots N_n$ represent, independently of one another, a nucleotide, $M_1, \ldots M_m$ represent, independently of one another, a nucleotide, (Ic') represents the compound obtained from (Ic) by cleavage of the ester bond with the solid support,

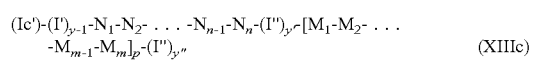

n is an integer ranging from 4 to 100,
m is an integer ranging from 4 to 100,
y is an integer ranging from 2 to 12,
y' is an integer ranging from 2 to 12,
p has the value 0 or 1 if y' is different from 0, and if y' has the value 0 then p has the value 0,
y" is an integer ranging from 0 to 12 if p has the value 1, and if p has the value 0 then y" has the value 0, the sum of the integers (y+y'+y") not being greater than 12;
or as a structural formula in the case when y'=p=0:

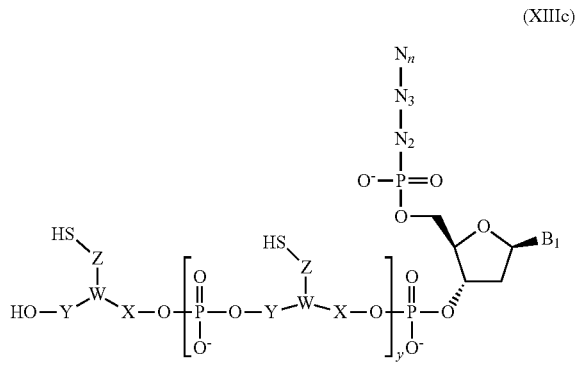

(XIIIc)

in which,
X, Y, W, Z have the same definition as for compound (I),
$N_2, \ldots N_n$, n and y have the same definition as for compound (XIIa),
Bn corresponds to a base used conventionally in a nucleotide chain.

During synthesis of the oligonucleotide, the thiol function is preferably protected. In fact, the thiol function may react with the incoming phosphoramidite function.

The step of deprotection of the thiol functions and removal of the solid support may be carried out in a single step of treatment of the modified oligonucleotide (XIIa) or (XIIIa).

Removal of the solid support may also be carried out in a first step, and deprotection of the thiol functions is then carried out in a second step.

The final oligonucleotide (XIIc) (respectively the final oligonucleotide (XIIIc)) is obtained independently of the starting thiol compound, whether starting from compound (Ia) or from compound (Ib). In fact, regardless of whether monomer (Ia) or (Ib) is used, the thiol monomer unit resulting from the oligomerization reaction corresponds to compound (I") described above.

The grafted supports of formulae $(XVI)_k$ described above allow initiation of oligonucleotide synthesis. Industrial or semi-industrial preparation of the solid supports grafted with sequences of oligomers that will be used as polythiol sequence in position 3' of an oligonucleotide may in particular be envisaged.

According to an embodiment of the invention, the nucleotide sequence $(N_1\text{-}N_2\text{-}\ldots\text{-}N_{n-1}\text{-}N_n)$ and, optionally, the nucleotide sequence $(M_1\text{-}M_2\text{-}\ldots\text{-}M_{m-1}\text{-}M_m)$ of the modified oligonucleotide of the invention, as described above, are specific to a virus, a bacterium or a gene responsible for or involved in a disease.

Within the meaning of the present application, by "specific" is meant that the sequence $(N_1\text{-}N_2\text{-}\ldots\text{-}N_{n-1}\text{-}N_n)$ and optionally the sequence $(M_1\text{-}M_2\text{-}\ldots\text{-}M_{m-1}\text{-}M_m)$ are complementary to the whole or part of at least one target nucleic acid sequence comprised in a gene or in the genome of a virus or of a bacterium, and characteristic of the latter. It is thus understood that hybridization of the sequence $(N_1\text{-}N_2\text{-}\ldots\text{-}N_{n-1}\text{-}N_n)$ and optionally of the sequence $(M_1\text{-}M_2\text{-}\ldots\text{-}M_{m-1}\text{-}M_m)$ with part or all of the target sequence corresponding to it leads to the formation of a duplex of nucleic acids having at most 2 mispairings. In one embodiment of the invention, the term "specific" signifies that the duplex formed only comprises just one or two mispairings. Advantageously, the duplex formed does not contain any mispairing. By "sequence characteristic of a gene or of the genome of a virus or of a bacterium" is meant a genomic, chromosomal or plasmid region of an organism, of a virus or of a bacterium, having an arrangement of nucleotides that is not found in the other organisms, owing to unique genetic variations.

Within the context of the invention, the terms "modified oligonucleotide" and "probe" are used synonymously and denote an oligonucleotide with 4 to 100 nucleotides and having at least 2 thiol functions, as described above. Advantageously, when it is used for genotyping, the modified oligonucleotide of the invention comprises 13 to 20 nucleotides, advantageously 14 or 15 nucleotides. The probe therefore has the capacity to graft onto a suitable surface, such as a surface coated with gold or with maleimide groups, and also has the capacity to hybridize, via its nucleotide part, to a target nucleotide sequence.

Preferably, the modified oligonucleotide of the invention comprises from 2 to 12 thiol functions, in particular between 2 and 8 functions, i.e. the modified oligonucleotide may comprise 2, 3, 4, 5, 6, 7 or 8 functions. Preferably, the modified oligonucleotide intended to be grafted on a gold surface comprises between 3 and 8, advantageously between 4 and 8 thiol functions. The modified oligonucleotide intended for conjugation with a surface comprising at least one carbon-carbon double bond or carbon-carbon triple bond or haloacetamide functions, preferably maleimide or acrylamide functions, advantageously comprises between 2 and 8 thiol functions, and preferably 4 thiol functions.

The term "target sequence", as used within the context of the invention, denotes a sequence that is complementary or partially complementary to the probe of the invention, and which is amplified from a gene or from the genome of a virus or of a bacterium, and preferably from a characteristic region of the latter.

The term "virus" denotes a biological entity that requires a host cell in order to replicate, and as a minimum comprises a nucleic acid and proteins, moreover the nucleic acid may be single-stranded or double-stranded DNA and/or RNA. The viruses comprise those capable of parasitizing the prokaryotes (for example the Myoviridae, Siphoviridae, Podoviridae, Microviridae and Inoviridae), those capable of parasitizing plants (phytoviruses such as tobamovirus), insects (for example the baculoviruses), fungi, and humans. Within the context of the invention, the viruses also comprise the arboviruses. The arboviruses group together morphologically heterogeneous viruses belonging to several different genera comprising more particularly the genera Flavivirus (Flaviviridae family), Alphavirus (Togaviridae family), Coltivirus (Reoviridae family), Phlebovirus (Bunyaviridae family). More broadly, the Flaviviridae family in particular comprises the genera Flavivirus (yellow fever virus, West Nile virus, tick-borne encephalitis virus (TBE), Japanese encephalitis virus, Saint Louis encephalitis virus, usutu virus and dengue virus), Hepacivirus (hepatitis C virus) and Pestivirus (bovine viral diarrhoea virus (BVD), swine fever virus). The Togaviridae family in particular comprises the genera Alphavirus (Sindbis virus, Ross River virus, O'nyong'nyong virus, Chikungunya virus) and Rubivirus (Rubella virus). The Reoviridae family in particular comprises the viruses affecting the digestive system (such as Rotavirus), or the respiratory system. The Bunyaviridae family in particular comprises the genera Hantavirus (Hantavirus pulmonary syndrome, Korean haemorrhagic fever), Nairovirus (Dugbe virus), Orthobunyavirus (Bunyamwera virus), Phlebovirus (Rift Valley fever) and Tospovirus.

Within the context of the invention, the viruses capable of infecting humans comprise the Vesiculoviruses (stomatitis vesicular virus, etc.), the Lyssaviruses (Rabies virus, Australian bat virus); the Picornaviruses (Rhinovirus, Poliovirus, hepatitis A virus, etc.), the Herpesviruses (chickenpox, shingles, cytomegalovirus CMV, Epstein Barr virus EBV, etc.), the Orthomyxoviruses (influenza virus, etc.), the Paramyxoviruses (measles virus, mumps virus, etc.), the Poxviruses (smallpox virus, etc.), Coronaviruses (SARS, etc.), Filoviruses (Ebola, etc.), the Hepadnaviruses (HBV) and the Retroviruses (HIV, HTLV, etc.).

The term "bacterium" denotes any prokaryotic living organism characterized by absence of a nucleus and organelles, and provided with a cell wall. This term in particular comprises the bacteria that may be pathogenic and may cause diseases and/or infections in humans, such as *Corynebacterium diphtherias* (diphtheria), *Treponema pallidum* (syphilis), *Mycobacterium tuberculosis* (tuberculosis), *Mycobacterium leprae* (leprosy), *Neisseria gonorrhoeae* (gonorrhoea), the *Rickettsia* (typhus), *Clostridium tetani* (tetanus), *Vibrio cholerae* (cholera), *Pseudomonas aeruginosa* and the Staphylococci (opportunistic pathogens). This term also comprises the bacteria implicated in transfusion risks and in nosocomial infections such as, for example, the Gram-negative bacteria *Escherichia coli, Klebsiella oxytoca, Klebsiella pneumoniae, Serratia marcescens, Yersinia enterocolitica, Enterobacter aerogenes, Acinetobacter baumannii*, and *Pseudomonas aeruginosa*, or the Gram-positive bacteria *Staphylococcus epidermidis, Staphylococcus aureus, Bacillus cereus, Streptococcus pyogenes, Propionibacterium acnes* and *Clostridium perfringens*.

According to an embodiment of the invention, the nucleotide sequence ($N_1$-$N_2$- . . . -$N_{n-1}$-$N_n$) and, optionally, the nucleotide sequence ($M_1$-$M_2$- . . . -$M_{m-1}$-$M_m$) are selected from:
the sequences SEQ ID NO: 1, SEQ ID NO: 4, SEQ ID NO: 27, SEQ ID NO: 28, SEQ ID NO: 35 or SEQ ID NO: 36, specific to the hepatitis C virus (HCV),
the sequences SEQ ID NO: 16, SEQ ID NO: 17 or SEQ ID NO: 40, specific to the flaviviruses,
the sequence SEQ ID NO: 18 or SEQ ID NO: 41, specific to the dengue virus, or
the sequence SEQ ID NO: 19, specific to the West Nile virus (WNV).

According to an embodiment of the invention, the nucleotide sequence ($N_1$-$N_2$- . . . -$N_{n-1}$-$N_n$) and, optionally, the nucleotide sequence ($M_1$-$M_2$- . . . -$M_{m-1}$-$M_m$) have a structure of the alpha anomer, beta anomer, linear, or "snail" type. When the nucleotide sequence has a structure of the beta anomer type, the modified oligomer of the invention (whose thiols are located at 5') hybridizes in an antiparallel manner with the target sequence. When the nucleotide sequence has a structure of the alpha anomer type, the modified oligomer of the invention (whose thiols are located at 3') hybridizes in a parallel manner with the target sequence.

Surface Functionalization

The modified oligonucleotides according to the invention may be deposited on a substrate in order to functionalize the surface of this substrate. The substrate may be metallic or made of polymer, conductive or non-conductive. It may be flat (partly or wholly) or curved, and may advantageously be of spherical shape.

According to an embodiment, the substrate is non-planar, for example in the form of microparticles or nanoparticles. The modified oligonucleotides according to the invention may then be grafted on these microparticles or nanoparticles. Preferably, these particles are magnetic. In fact, these magnetic particles may then easily be brought to the surface of an electrode or to the bottom of the wells of a microplate, for the purpose of a test for detecting, genotyping or sequencing, by application of a magnet. The use of a non-planar support of the microparticle or nanoparticle type in the context of the detection method of the invention advantageously makes it possible to increase the area of the surface on which the modified oligonucleotides of the invention may be grafted, and thus makes it possible to increase the proportion of hybridizations between the probes and the target sequences.

According to an embodiment, the substrate is metallic, for example of copper or titanium, and its surface is coated partially or completely with a gold or platinum film, preferably gold.

According to an embodiment, the substrate is of polymer, preferably a conductive polymer.

According to an embodiment, the substrate may comprise receiving zones covered with a gold or platinum film or covered with alkenyl, alkynyl or haloacetamide functions, such as maleimide or acrylamide functions, on which the modified oligonucleotide is deposited.

According to an embodiment of the invention, the groups comprising at least one carbon-carbon double bond or carbon-carbon triple bond are selected from the alkenes activated by a carbonyl function in the alpha position, and the alkenes are preferably selected from the maleimide and acrylamide groups.

According to an embodiment of the invention, the haloacetamide groups are selected from the bromoacetamido and iodoacetamido groups.

According to an embodiment of the invention, the groups comprising at least one carbon-carbon triple bond are selected from the alkynes activated by a carbonyl function in the alpha position, and the alkynes are preferably selected from the 2-propynamide groups.

Figure 16A:
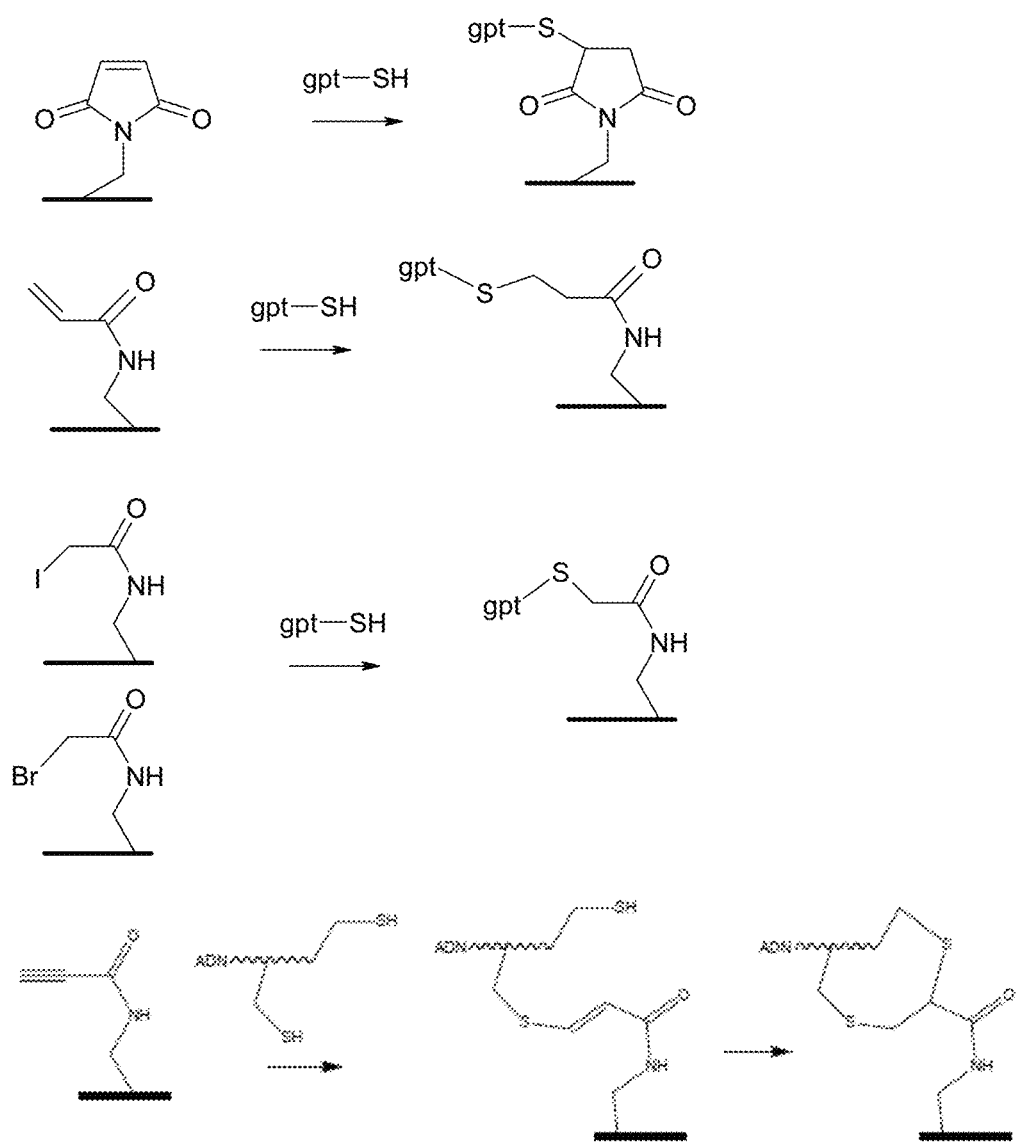
FIG. 16a shows the reactions between the modified oligonucleotide according to the invention and the surface grafted with activated alkenyl or alkynyl groups.

As illustrated in FIG. 16a, in which the compound gpt-SH represents the modified oligonucleotide according to the invention, the thiol function reacts with the carbon-carbon double bond or carbon-carbon triple bond activated by a carbonyl function in the alpha position. From top to bottom in FIG. 13a, the first functionalization reaction corresponds to a maleimide grafted surface, the second reaction corresponds to an acrylamide grafted surface, the third reaction corresponds to an iodoacetamido or bromoacetamido grafted surface and the fourth reaction corresponds to a 2-propynamide grafted surface prepared in the case of a modified oligonucleotide according to the invention comprising two thiol compounds.

In the case of FIG. 16b, the surface is grafted with unactivated alkenyl groups (1st reaction) and alkynyl groups (2nd reaction). Reaction between the thiol function of the modified oligonucleotide and the surface groups is carried out using activation by light (X, =265 nm). The first functionalization reaction is carried out using a monothiol modified oligonucleotide represented schematically by gpt-SH and the second reaction is carried out using a dithiol modified oligonucleotide.

In the case when the support is grafted with alkynyl functions, surface functionalization with a polythiol modified oligonucleotide is very interesting as it leads to a cyclic structure owing to two successive reactions between a first thiol function and the -yne function in a first step and then between a second thiol function and the resultant -ene function in a second step (FIGS. 16a and 16b).

According to a preferred embodiment, the substrate is grafted with maleimide or acrylamide groups.

Thus, the invention makes it possible for example to functionalize a gold surface by creating gold-sulphur bond(s) between the surface of the substrate and the modified oligonucleotide or to functionalize a surface grafted with maleimide or acrylamide functions by creating thioether bond(s).

Fixation of the modified oligonucleotides on the surface of the substrate is carried out by immersing the surface to be treated in a solution comprising the modified oligonucleotide according to the invention as described above. One or more further steps of washing and drying are generally provided. In general, the solution of modified oligonucleotides is at a concentration comprised between 0.10 µM and 500 preferably between 0.5 µM and 100 µM when the substrate surface is of gold and between 50 nM and 200 nM, preferably between 75 nM and 150 nM when the substrate surface is formed from maleimide. Immersion is followed by washing to remove anything which has not reacted.

The presence of several sulphur atoms on the oligonucleotide makes it possible to create several gold-sulphur bonds, or several thioether bonds, which allows the oligonucleotide to be stabilized on the surface.

A subject of the invention therefore comprises a substrate grafted with at least one modified oligonucleotide as described above, said substrate comprising at least one receiving zone coated with a substance that tolerates the grafting of said modified oligonucleotide. According to an embodiment of the invention, the substrate is in the form of an electrode. According to another embodiment of the invention, the substrate is in the form of a microplate with 96 wells or more.

According to an embodiment of the invention, the grafted substrate according to the invention is of metal, preferably of copper or titanium, and comprises at least one receiving zone coated with a gold or platinum film. According to another embodiment of the invention, the grafted substrate is of plastic, preferably of polystyrene and the receiving zone is coated with maleimide groups and/or comprises on its surface at least one carbon-carbon double bond or carbon-carbon triple bond or haloacetamide functions, preferably maleimide or acrylamide functions.

According to an embodiment of the invention, the density of grafting of the modified oligonucleotide according to the invention obtained on the receiving zone results from the use of grafting solutions from 10 nM per well to 500 nM per well, when a 96-well plate is used as the substrate. Advantageously, the density of grafting of the modified oligonucleotide according to the invention on the receiving zone of the substrate is obtained using a grafting solution of 100 nM per well when a 96-well plate is used as the substrate.

Fixation to Markers or Ligands

The modified oligomers of the present invention may also be bound by one or more points of attachment to markers or ligands, which may be, for example, enzymatic, chromogenic, fluorogenic, radioactive, or chemiluminescent markers, metals, metal ions, hormones, proteins, peptides, saccharides, oligosaccharides, nucleolytic or proteolytic agents, binding agents, such as a biotin, an antigen, a hapten, an antibody or a receptor. Advantageously, this marker or ligand makes it possible to detect the hybridization event between the modified oligonucleotide of the invention and a representative target sequence of a gene, of a virus or of a bacterium. According to another embodiment of the invention, the marker or ligand binds to the representative target nucleotide sequence of a gene, of a virus or of a bacterium, and makes it possible to detect the hybridization event between the modified oligonucleotide of the invention and the target sequence.

Detection Method

The present invention further relates to a method for detecting at least one target nucleic acid in a biological sample, comprising a step of detecting said target nucleic acid with at least one detection probe formed by a modified oligonucleotide as described above.

According to an embodiment of the invention, the detection method comprises the steps of:
- obtaining at least one "source" nucleic acid from a biological sample,
- producing an amplicon by the amplification of a target nucleic acid from the source nucleic acid, and
- detecting hybridization between the amplicon and at least one detection probe formed by a modified oligonucleotide as described above.

By "biological sample" is meant any substance containing or suspected of containing a nucleic acid, such as DNA or RNA, and obtained from a human, an animal, a vegetable or from any liquid or solid composition. The biological sample includes for example the samples of tissues or fluids isolated from an individual or from individuals, comprising but not limited to skin, blood, plasma, serum, spinal fluid, lymphatic fluid, synovial fluid, urine, tears, blood cells, bone marrow, organs, tumours, as well as the samples of constituents of in vitro cell cultures. The biological sample may advantageously be treated to destroy the structure of the tissues or cells, in order to bring their intracellular constituents into solution.

By "amplicon" is meant a nucleic acid molecule generated during a procedure for amplification of a characteristic target nucleic acid sequence of the gene, virus or bacterium contained in the biological sample. According to an embodiment of the invention, the amplicon is generated by the polymerase chain reaction (PCR) technique. The amplicon used in the detection method of the invention advantageously has a size ranging from 75 bp to about 500 bp. In particular it appears that one of the advantages of the method of the invention is the possibility of using amplicons having a length of one or more hundreds of nucleotides, which proves impossible in the detection methods known in the prior art. The detection method of the invention thus makes it possible to select and amplify larger target sequences in genes, viruses or bacteria.

According to an embodiment of the invention, the detection method makes it possible to determine the genotype and/or subtype of a virus present in a biological sample. The amplicon is more specifically generated by the amplification of a target nucleotide sequence, corresponding to a genomic region of the virus bearing information relating to the viral genotype and/or subtype, and detection is carried out with a probe specific to a particular viral genotype and/or subtype. The method of the invention thus makes it possible to effect detection based on target sequences containing more information on the viral or bacterial type, or subtype. This advantage results directly from the modified oligonucleotide according to the invention, its method and capacity for fixation to the fixation zone of the substrate. Advantageously, it is therefore no longer essential to define primers for amplifying a target sequence that is as short as possible from the viral or bacterial genome. The method of the present invention makes it possible instead to select primers localized in conserved regions in the families of viruses or of bacteria in question, and amplify longer target sequences. This results in significant savings and increased ease of use, in that the same primers may be used for amplifying a genomic zone encountered in several viral or bacterial types and/or subtypes, without fear of seeing the hybridization results falsified by the size of the amplicon used.

According to an embodiment of the invention, the step of producing the amplicon of the detection method of the invention is carried out with a mixture of nucleotide primers, preferably selected from the primer pairs:

SEQ ID NO: 8 and SEQ ID NO: 9, when the amplicon is generated from HCV, whatever viral genotype is involved. This primer pair is generic and allows amplification of a "long" amplicon of 401 nt starting from any genotype of HCV;

SEQ ID NO: 10 and SEQ ID NO: 9, a pair allowing generation of "short" amplicons of 191 nt specific to genotype 1a/1b;

SEQ ID NO: 29 and SEQ ID NO: 9, a pair allowing generation of "short" amplicons of 108 nt specific to genotype 2;

SEQ ID NO: 8 and SEQ ID NO: 11, a pair allowing generation of "short" amplicons of 143 nt specific to genotype 3a;

SEQ ID NO: 8 and SEQ ID NO: 30, a pair allowing generation of "short" amplicons of 175 nt specific to genotype 4a/4d; and SEQ ID NO: 20 and SEQ ID NO: 21, and/or SEQ ID NO: 22 and SEQ ID NO: 21 when the amplicon is generated from a flavivirus.

According to an embodiment, the modified oligonucleotide according to the invention is used in the detection method at a density resulting from contacting a grafting solution ranging from 10 nM to 500 nM with a well, when a 96-well plate is used as the substrate. Advantageously, the grafting solution of the modified oligonucleotide according to the invention is of 100 nM, when a 96-well plate is used as the substrate. When the modified oligonucleotide according to the invention comprises 2 thiol functions, the grafting solution used has a concentration of modified oligonucleotide of at least 10 nM (when a 96-well plate is used as substrate) and the concentration of the amplicon used in the detection method is of at least 100 pM. When the modified oligonucleotide according to the invention comprises 4 thiol functions, the grafting solution used has a concentration of modified oligonucleotide of at least 10 nM per well and the concentration of the amplicon used in the detection method is of at least 10 pM per well, when a 96-well plate is used as the substrate.

The detection method according to the invention offers a particular advantage for the genotyping of HCV, in that it in particular allows the various known genotypes and subtypes of HCV to be distinguished, using a simple molecular detection test.

Infections associated with the hepatitis C virus in fact represent an extremely important health problem, in that the infected individuals risk developing liver diseases, cirrhoses, and primary hepatic carcinomas, and in that they also constitute a reservoir of infection. Epidemiological studies forecast a trebling of the annual number of deaths resulting from HCV over the course of the 10 next years if new diagnostic and therapeutic systems are not developed.

Characterized by considerable genetic variability, HCV is classified in 6 major genotypes, comprising more than 80 subtypes. Precise determination of the infectious genotype and/or subtype is crucial for the therapeutic strategies, and makes it possible to predict the efficacy of the antiviral response and define the duration of therapy, as well as the treatment type and dosage. Identification of the precise classification of the HCVs found in the infected individuals is also important for epidemiological monitoring, with the aim of monitoring the distribution of the viral strains and of identifying the transmission factors.

Many of the commercially available tests for detecting and/or quantifying RNA of HCV are based on the sequences found in the 5' noncoding region (5'NCR), which constitutes one of the most conserved and best characterized regions of HCV. The 5'NCR region is thus selected as the target in the various known methods of genotyping that are distributed commercially, such as the INNO LiPA HCV II test, from Bayer, the Trugene HCV 5'NCR kit from Bayer/Siemens Healthcare (WO2007/076493), based on sequence analysis and the duplex mobility test, or a system for detecting hybridization comprising a plurality of typing of HCVs designed in the 5'NCR region or in the NS5 region developed by Roche Molecular Systems (US 2007/014160).

However, the presence of mutations in the 5'NCR region leads to poor classification of the HCV genotypes in 5 to 8% of cases, leading to serious consequences for the results of the treatment. The 5'NCR region no longer seems to present a sufficient degree of reliability for identifying genotypes 2 and 4 of the virus.

The reference method for carrying out genotyping of HCV resides moreover in the sequencing of specific regions of the HCV, and in particular of the NS5b region of the virus, coding for the RNA-dependent RNA polymerase. However, sequencing proves expensive and time-consuming, and requires specialized equipment and trained operators. Therefore it is not suitable for conductive large-scale clinical studies.

There is therefore a need for improved methods for detecting and/or genotyping HCV for distinguishing the various known genotypes and subtypes of HCV, using a simple molecular test, such as that of the invention.

The present invention further relates to an oligonucleotide having a nucleotide sequence selected from the sequences SEQ ID NO: 1, SEQ ID NO: 4, SEQ ID NO: 27, SEQ ID NO: 28, SEQ ID NO: 16, SEQ ID NO: 17, SEQ ID NO: 18, SEQ ID NO: 19, SEQ ID NO: 35, SEQ ID NO: 36, SEQ ID NO: 40 and SEQ ID NO: 41. Advantageously, the oligonucleotide of sequence SEQ ID NO: 1 corresponds to a nucleotide sequence found specifically in HCV of type 1a/1b and makes it possible to detect the latter specifically in the context of a detection method as described above. Advantageously, the oligonucleotide of sequence SEQ ID NO: 27 corresponds to a nucleotide sequence found specifically in the HCV of type 2 and makes it possible to detect the latter specifically in the context of a detection method as described above. Advantageously, the oligonucleotide of sequence SEQ ID NO: 35 corresponds to a nucleotide sequence found specifically in the HCV of type 2a/2c and makes it possible to detect the latter specifically in the context of a detection method as described above. Advantageously, the oligonucleotide of sequence SEQ ID NO: 36 corresponds to a nucleotide sequence found specifically in the HCV of type 2b and makes it possible to detect the latter specifically in the context of a detection method as described above. Advantageously, the oligonucleotide of sequence SEQ ID NO: 4 corresponds to a nucleotide sequence found specifically in the HCV of type 3a and makes it possible to detect the latter specifically in the context of a detection method as described above. Advantageously, the oligonucleotide of sequence SEQ ID NO: 28 corresponds to a nucleotide sequence found specifically in the HCV of type 4a/4d and makes it possible to detect the latter specifically in the context of a detection method as described above. Advantageously, the oligonucleotide of sequence SEQ ID NO: 16, SEQ ID NO: 17 or SEQ ID NO: 40 corresponds to a nucleotide sequence found specifically in the flaviviruses and makes it possible to detect the latter specifically in the context of a detection method as described above. Advantageously, the oligonucleotide of sequence SEQ ID NO: 18 corresponds to a nucleotide sequence found specifically in the dengue viruses and makes it possible to detect the latter specifically in the context of a detection method as described above. Advantageously, the oligonucleotide of sequence SEQ ID NO: 41 corresponds to a nucleotide sequence found specifically in the dengue viruses of serotype 4, and makes it possible to detect the latter specifically in the context of a detection method as described above. Advantageously, the oligonucleotide of sequence SEQ ID NO: 19 corresponds to a nucleotide sequence found specifically in the West Nile viruses and makes it possible to detect the latter specifically in the context of a detection method as described above.

Detection Kits

Another subject of the invention consists of a detection and/or diagnostic kit comprising at least one support comprising at least one receiving zone, on which at least one modified oligonucleotide according to the invention is placed.

Thus, the detection kit may be used for screening biologically active molecules or for diagnostic or sequencing tests. It may be envisaged that the diagnostic kit comprises several separate receiving zones, on which a solid support grafted with identical or different oligonucleotides is deposited. For example, solid supports grafted with identical or different modified oligonucleotides may be placed on separate receiving zones of a substrate covered with a gold film or of a substrate grafted with functions comprising at least one carbon-carbon double bond or carbon-carbon triple bond or haloacetamide functions, preferably maleimide or acrylamide functions, so as to form a test and/or diagnostic support.

The support may in particular be a gold electrode. The test kit may advantageously comprise an electrochemical cell comprising a working electrode, a counter-electrode and a reference electrode. The working electrode may be of gold, the counter-electrode of platinum and the reference electrode of silver. Investigation of the interaction of a modified oligonucleotide with a molecule to be tested may comprise a step of cyclic voltammetry.

Grafting with a surface comprising at least one carbon-carbon double bond (alkenyl function) or a carbon-carbon triple bond (alkynyl function) or haloacetamide functions, preferably maleimide or acrylamide functions, may for example be used for applications in the field of diagnostics in the microplate format and/or for carrying out tests of the ELOSA type (Enzyme-Linked OligoSorbent Assay). In the course of this type of test, the surface of the wells is grafted with alkenyl, alkynyl or haloacetamide functions, preferably maleimide or acrylamide functions 1. Then the surface is brought into contact with modified oligonucleotides according to the invention. Thus, one or more thioether bonds form owing to the presence of one or more thiol functions on the oligonucleotides according to the invention. Then the test consists of contacting a test sample comprising a target nucleotide sequence with the wells thus functionalized, in particular for measuring the hybridization of the oligonucleotides. Measurement may for example be based on fluorescence by labelling the oligonucleotide chains.

The invention also relates to the use of a modified oligonucleotide as described above and comprising at least two thiol functions for surface grafting comprising at least one carbon-carbon double bond or carbon-carbon triple bond or haloacetamide functions, preferably maleimide or acrylamide functions. According to an embodiment, the compound may comprise three or four thiol functions. The modified oligonucleotide immobilized on the surface comprising at least one carbon-carbon double bond or carbon-carbon triple bond or haloacetamide functions, preferably maleimide or acrylamide functions, via at least two thiol functions, displays very good stability for use in a diagnostic test, such as a test of the ELOSA type, as well as better availability with respect to the targets. When the number of thiol functions in the compound increases, the number of hybridizations on the whole of the support grafted during the detection test increases. Thus, a modified oligonucleotide having four thiol functions makes it possible to obtain more effective hybridization of the target.

EXAMPLES

In the examples, by "probe" is meant an oligonucleotide chain comprising at least one thiol compound according to the invention intended to be immobilized on a surface.

By "target" is meant an oligonucleotide chain intended to hybridize with the probe, for example during a diagnostic test.

Example 1: Synthesis of an Oligomer

Synthesis of the compound 1-O-(4,4'-dimethoxytrityl)-2-(6-5-acetylthiohexyloxymethyl)-2-methylpropane-1,3-diol 4

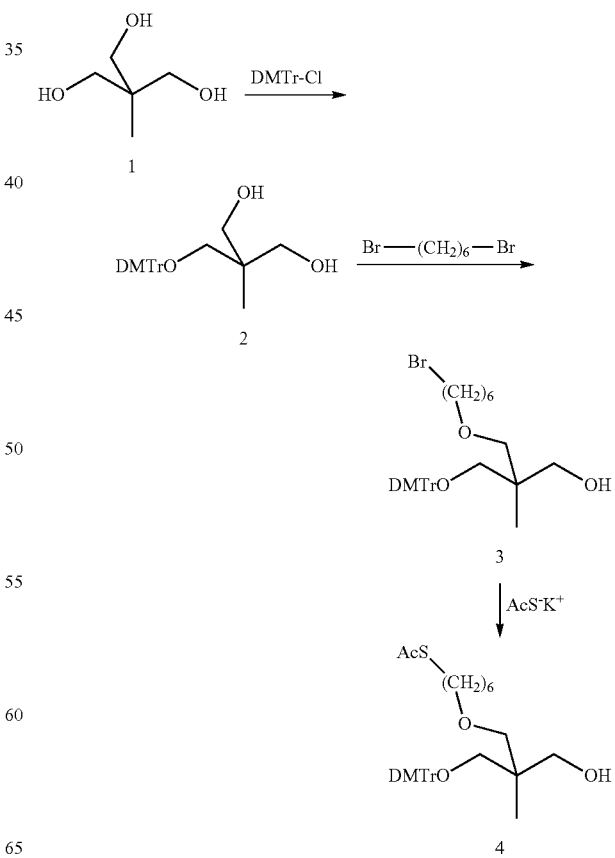

Compound 3 is obtained from compound 1 following the protocol described in Pourceau, G., Meyer, A., Vasseur, J. J., and Morvan, F., *Journal of Organic Chemistry* 74, 2009, 1218-1222.

Crown ether 18-6 (70 mg, 0.26 mmol) is added to a solution of 1-O-(4,4'-dimethoxytrityl)-2-(6-bromohexyloxymethyl)-2-methyl-1,3-propanediol 3 (556 mg, 0.95 mmol) and of potassium thioacetate (162 mg, 1.42 mmol) in anhydrous toluene (10 mL). The mixture is subjected to magnetic stirring for 2 hours at 50° C. After dilution with dichloromethane (150 mL), the mixture is filtered and the organic phase is washed with water (2×50 mL) and then dried over $Na_2SO_4$. After evaporation, the crude reaction product is purified by silica chromatography (0 to 30% of ethyl acetate in cyclohexane), giving the desired product in the form of a colourless oil (413 mg, 75%).

Synthesis of 1-O-(4,4'-dimethoxytrityl)-2-(6-S-acetylthiohexyloxymethyl)-2-methyl-3-O-(2-cyanoehtyl-N,N'-diisopropylphosphoramidite)-propane-1,3-diol 5

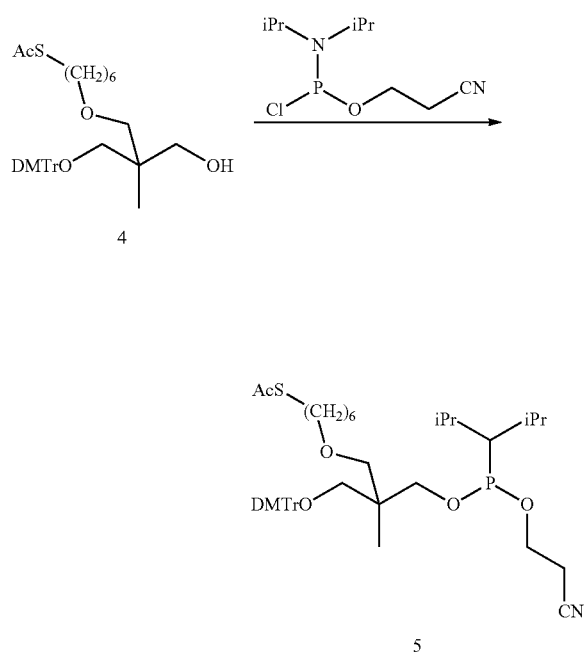

2-Cyanoethyl-N,N'-diisopropylchlorophosphoramidite (190 μL, 0.85 mmol) is added to a solution of 1-O-(4,4'-dimethoxytrityl)-2-(6-S-acetylthiohexyloxymethyl)-2-methylpropane-1,3-diol 4 (413 mg, 0.71 mmol) and diisopropylethylamine (186 μL, 1.06 mmol) in anhydrous dichloromethane (10 mL). The mixture is subjected to magnetic stirring for one hour at ambient temperature. The excess reagent is neutralized by adding 500 μL of water and then the mixture is diluted with dichloromethane (150 mL). The organic phase is washed with a saturated aqueous $NaHCO_3$ solution (100 mL), then dried over $Na_2SO_4$. After evaporation, the crude reaction product is purified by silica chromatography (0 to 30% of ethyl acetate in cyclohexane containing 4% of triethylamine) giving the desired compound 5 in the form of a colourless oil (400 mg, 72%).

Synthesis of the Thiol Solid Support 6

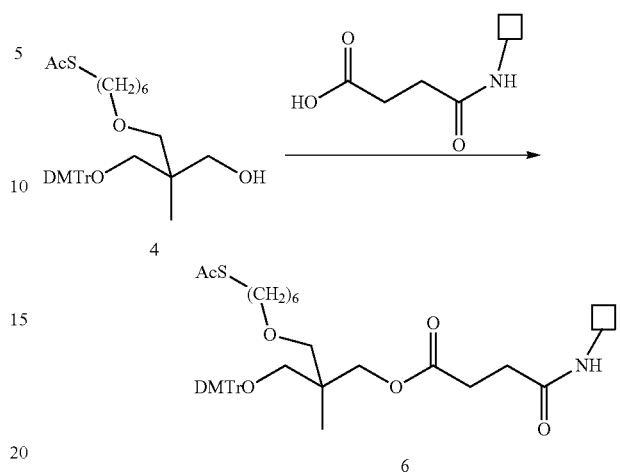

In a ground-glass tube, 1-O-(4,4'-dimethoxytrityl)-2-(6-S-acetylthiohexyloxymethyl)-2-methyl-1,3-propanediol 4 (178 mg, 0.3 mmol) and dimethylaminopyridine (DMAP 36 mg, 0.3 mmol) are coevaporated with 3 mL of anhydrous pyridine. Then succinyl-long chain alkylamine-CPG (Controlled Pore Glass) (1 g), anhydrous pyridine (5 mL), anhydrous triethylamine (160 mL, 1.2 mmol) and ethyldimethylaminopropyl carbodiimide (EDC, 280 mg, 2.0 mmol) are added. Then it is rinsed with 1 mL of anhydrous pyridine. The mixture is stirred overnight.

The mixture is filtered and washed with $CH_2Cl_2$ (10 mL) and then dried in a desiccator. The thiol compound on solid support is treated with a solution of acetic anhydride, N-methylimidazole, 2,6-lutidine in THF for 3 h with stirring. The mixture is filtered and washed with $CH_2Cl_2$ (10 mL) and then dried in a desiccator to give the thiol solid support 6 (940 mg) with a functionalization of 29 μmol/g.

Example 2: Preparation of Modified Oligonucleotides

Three oligonucleotides comprising a ferrocene group in position 5' and an increasing number of thiol compounds of type (Ia) according to the invention (1, 2 and 4 thiol compounds) were synthesized in a DNA synthesizer. The ferrocene group was used in order to visualize the immobilization of the oligonucleotide on the gold surface by cyclic voltammetry. One, two or four thiol groups were introduced onto a solid support of the propanediol type and the DNA sequence SEQ ID NO: 7 was grafted. Finally, an alpha-thymidine phosphoramidite bearing a ferrocene group was introduced in position 5' of the modified oligonucleotide. The deprotection that follows is carried out in two steps. Firstly, the medium is treated with 10% of piperidine in acetonitrile for 10 minutes in order to remove the cyanoethyl group by beta-removal and the resultant acrylonitrile is removed from the medium by washing with acetonitrile. Then treatment with concentrated ammonium hydroxide makes it possible to remove the acyl protective groups on the nucleobases and on the thiol functions and makes it possible to hydrolyse the succinyl linkage (solid support). This protocol makes it possible to avoid Michael addition between the deprotected thiol functions and the acrylonitrile. After evaporation, the unsupported modified oligonucleotide is purified by reversed-phase HPLC chromatography on a C18 column.

Tetrathiol (Oligonucleotide Modified with 4 Thiol Compounds)

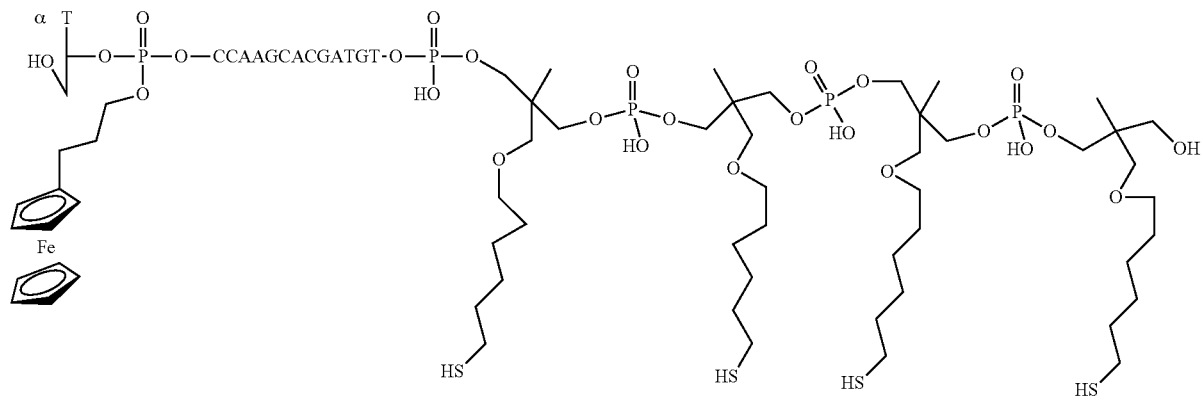

Dithiol (Oligonucleotide Modified with 2 Thiol Compounds)

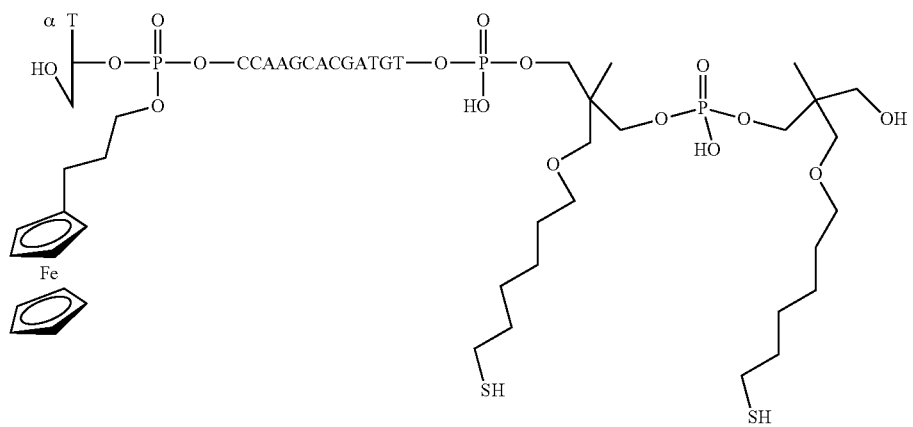

Monothiol (Oligonucleotide Modified with 1 Thiol Compound)

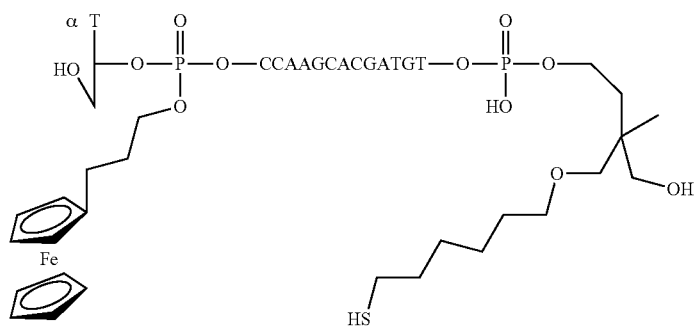

Grafting and Investigation of Stability of the Modified Oligonucleotides (Tetrathiol, Dithiol and Monothiol)

For this study, a VMP3 Biologic multichannel potentiostat (Biologic Science Instruments, Pont de Claix) was used. The results were recorded using the EC-Lab software from Biologic Science Instruments.

The electrochemical cell consists of a gold electrode with surface area of 0.28 cm², a platinum counter-electrode and an Ag/AgCl reference electrode.

Step 1: Reduction of the Thiol Groups 4 nmol of ODN-thiol (oligonucleotides modified with one or more thiol compounds) is reduced in a solution of Tris(2-carboxyethyl)phosphine hydrochloride (TCEP,HCL, Sigma-Aldrich) (160 mM) i.e. a concentration of 20 mM of TCEP,HCl in the solution, at 20° C., for 2 h under argon.

The ODN is purified by two successive dilutions/centrifugations with a solution of TCEP,HCl 20 mM degassed on amicon YM3000 filters (Millipore) for 15 min at 14000 rcf (rcf=Relative Centrifugal Force). After dilution in 450 μL of degassed 100 mM phosphate buffer, the medium is centrifuged again on amicon YM3000 filters, 30 min, 14000 rcf.

A grafting solution containing 4 nmol of ODN, 90 mM of sodium phosphate, 2 mM of TCEP,HCl is obtained.

Step 2: Activation of the Gold Electrode

The gold working electrode is cleaned by a first washing in acetone for 10 minutes with ultrasound. Once dried, the surface is immersed in a "piranha" solution (0.7 mL $H_2SO_4$, 0.3 mL $H_2O_2$) for 1 minute in order to remove any organic residue from the surface.

Finally basic activation of the electrode consists of surface cleaning of the gold by generation of hydrogen at the electrode by hydrolysis of water in 0.5M soda at negative potentials (−1.4V vs Ag/AgCl) for several cycles.

Step 3: Grafting of the Probe

After rinsing, the grafting solution containing the thiol oligonucleotide is brought into contact with the activated gold electrode, for three days under inert atmosphere.

After rinsing, the electrochemical cell is filled with the analysis electrolyte (10 mM dibasic sodium phosphate, 10 mM monobasic potassium phosphate, 250 mM sodium perchlorate, pH 6.5).

The surface is passivated with a 1 mM mercaptopropanol solution for 30 minutes, and after rinsing, the cell is put in the analysis electrolyte for 2 h in order to stabilize the grafted layer.

Step 4: Analysis of the Stability of the Surface Grafted Compounds

The analyses are carried out by cyclic voltammetry (CV) at 50 mV/s, between −0.1V and 0.45V. Studies of the stability of the grafted layer are carried out after stabilization of the electrochemical signal for 2 h by cycling every 30 minutes.

The cell is filled with distilled water degassed at 60° C. or 80° C. for 1 or 5 minutes, and after rinsing, the cell is filled with 1.5 mL of analysis electrolyte phosphate (20 mM) perchlorate (250 mM). After stabilization for 30 minutes, CV is carried out.

The operation is repeated as often as necessary.
Results

Comparison of the degree of grafting of the 3 oligonucleotides modified with thiol compounds (tetrathiol, dithiol and monothiol) was carried out. The degree of grafting was determined by integration of the oxidation peak of the ferrocene. In fact, the electron charge transferred is directly related to the number of ferrocenes present at the surface of the electrode, and therefore to the number of probes grafted on the gold.

The results given below correspond to the mean value of the degrees of grafting of 3 different graftings for each probe.

|  | molecules/cm$^2$ |
| --- | --- |
| monothiol | 5.21E+12 |
| dithiol | 5.81E+12 |
| tetrathiol | 1.40E+12 |

Figure 5:
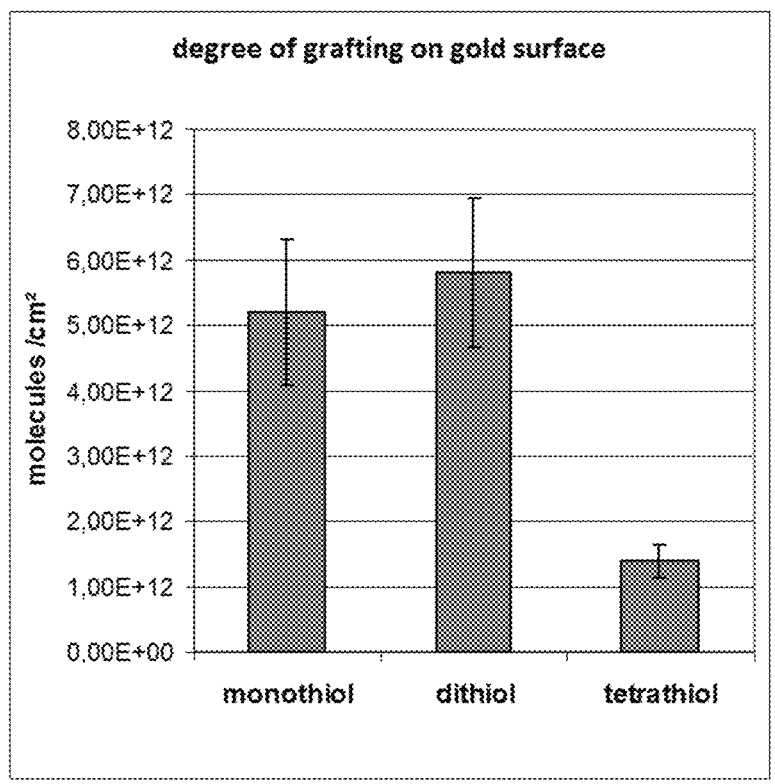
FIG. 5 shows a histogram of the degree of grafting of modified oligonucleotides on a gold surface.

A histogram of the results is shown in FIG. 5.

The degrees of grafting for monothiol and dithiol are fairly comparable, and a lower level of grafting of tetrathiol is observed, probably due to greater hindrance, in keeping with the number of thiol linkages. Despite this difference, the degree of grafting of the tetrathiol is still considerable and it is very reproducible.

A stability test on the 3 oligonucleotides modified with thiol compounds with respect to temperature was carried out in degassed distilled water. The evolution of the electrochemical response was monitored by cyclic voltammetry. The percentage decrease in intensity of oxidation of the ferrocene is calculated relative to the signal obtained after stabilization.

Figure 6:
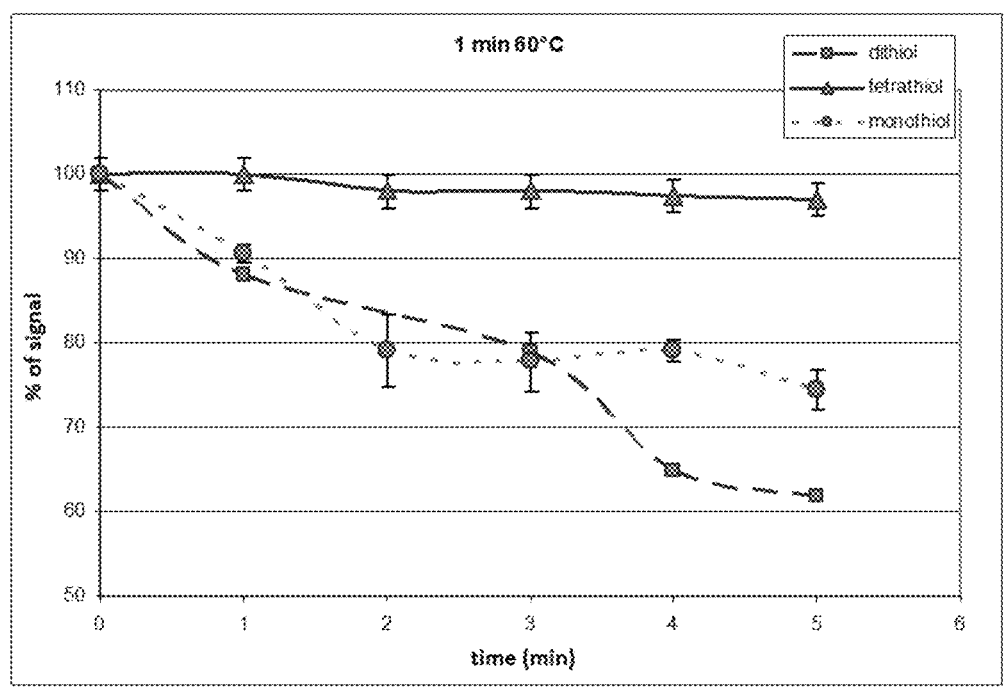
FIG. 6 shows a diagram presenting the stability of grafting of modified oligonucleotides on a gold surface as a function of time at 60° C.
Figure 7:
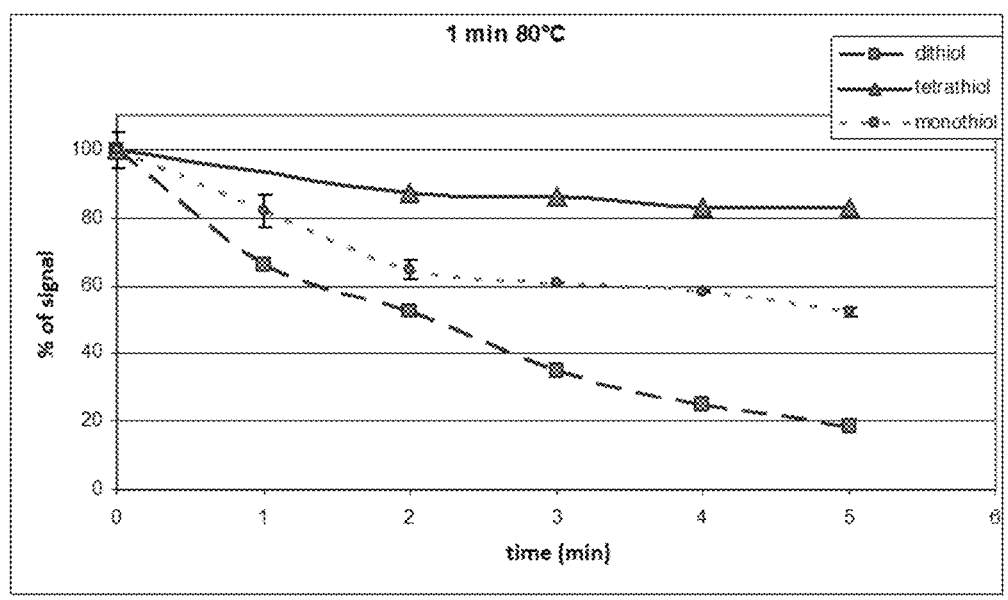
FIG. 7 shows a diagram presenting the stability of grafting of modified oligonucleotides on a gold surface as a function of time at 80° C.

These decreases as a function of time are presented in FIGS. 6 and 7.

The tetrathiol molecule is very stable with respect to successive treatments in water at 60° C. (FIG. 6). In fact, after 5 times one minute of this treatment, 97% of the starting signal remains, in contrast to monothiol (70% of starting signal) and dithiol (62% of starting signal).

At 80° C., the loss of signal is greater (FIG. 7). After five successive treatments of one minute, 83% of the starting signal is again quantifiable for the tetrathiol. Thus, the stability of the tetrathiol is well above that of the monothiol (45% of residual signal) and that of the dithiol (18% of residual signal).

This study shows the notable gain in stability of thiol grafting on gold by using an oligonucleotide modified with 4 thiol compounds (tetrathiol), in comparison with grafting of a monothiol or of a dithiol. The lack of stability of this last-mentioned dithiol may be due to possible competition between grafting on gold and ring closure for reforming the intramolecular disulphide bridge. It therefore appears preferable to maintain a number of four thiols on the grafting linkage to ensure good stability with respect to temperature.

Example 3: Application to the Detection of Hepatitis C Virus

Target Samples to be Tested
1) Natural targets: "HCV (+)" amplicons
Plasma samples from blood donors, tested positive for the presence of HCV at the national scale, are analysed by sequencing. The viral genotype and subtype of the HCV infecting each donor are determined.

"HCV (+)" amplicons of 401 bp are produced from the NS5b viral region of HCV, by RT-PCR from each of the plasma samples described above. The RNA is extracted from 200 μL of human plasma using the High Pure Viral Nucleic Acid kit (Roche) according to the manufacturer's recommendations. The RNA is eluted in 50 μL of sterile water (DNase/RNase free). For the reverse-transcription (AT) step, 11 μL of RNA is denatured at 72° C. for 10 minutes and reverse-transcribed in the presence of 44, of 5× First Strand Buffer (Invitrogen), 2 μL of 10× Hexanucleotide Mix (Roche), 2 µL of 10 mM dNTP mix (Invitrogen) and 200 U of SuperScript® II Reverse Transcriptase (Invitrogen). The reverse-transcription conditions are as follows: 10 min at 23° C., 45 min at 37° C., and 10 min at 95° C.

Five microlitres of cDNA are then amplified by PCR (polymerase chain reaction) using the primers:
"Biotinylated HCVsense" (of sequence: [Btn]-TGG GGA TCC CGT ATG ATA CCC GCT GCT TTG A (or [Btn]-SEQ ID NO: 8)) and
"HCVantisense" (of sequence GGC GGA ATT CCT GGT CAT AGC CTC CGT GAA (SEQ ID NO: 9)) (see Tamalet C. et al. 2003, *Journal of Medical Virology* 71: 391-398).

The amplification reaction is carried out in 50 µL of reaction mixture comprising: 1× PCR Buffer without MgCl$_2$ (Invitrogen), 0.2 µM of each primer, 1.5 mM MgCl$_2$ (Invitrogen), 0.2 mM dNTP mix (Invitrogen) and 1.3 U Taq Polymerase (Invitrogen). The PCR conditions are as follows: 5 min at 95° C., 40 cycles (denaturation: 40 s, 95° C.; hybridization: 40 s, 56° C.; elongation: 50 s, 72° C.), and a final extension of 10 min at 72° C.

The HCV amplicons obtained are analysed by agarose gel electrophoresis, aliquots are taken and stored at –20° C. before use.

These amplicons, whose original viral genotypes are known, are stored in the form of a library.

An example of an amplicon with a length of 401 bp obtained from a viral strain 1a/1b, with reference #PTR6719 has the sequence:

(SEQ ID NO: 12)
5'-TGGGGATCCCGTATGATACCCGCTGCTTTGACTCAACGGTCACTG

AGAATGACATCCGTGTTGAGGAGTCAATTTACCAATGTTGTGACCTAG

CCCCCGAAGCCAGACAGGCCATAAGGTCGCTCACAGAGCGGCTTTACA

TCGGGGGTCCCCTGACTAATTCAAAAGGGCAGAACTGCGGCTATCGCC

GGTGCCGCGCGAGCGGTGTGCTGACGACCAGCTGCGGTAATACCCTCA

CATGTTACTTGAAGGCCTCTGCGGCCTGTCGAGCTGCAAAGCTCCAGG

ACTGCACAATGCTCGTGTGCGGAGACGACCTTGTCGTTATCTGTGAAA

GCGCGGGAACCCARGAGGATGCGGCGAGCCTACGAGTCTTCACGGAGG

CTATGACCAGGAATTCCGCC-3'.

An example of an amplicon with a length of 401 bp obtained from a viral strain 2, with reference #PTR7761 has the sequence:

(SEQ ID NO: 31)
5'-TGGGGATCCCGTATGATACCCGCTGCTTTGACTCAACTGTCACTG

AGAGAGACATCAGAACCGAGGAGTCCATATACCAGGCCTGCTCCCTAA

CCGAGGAGGCTCGCACCGCCATACACTCGCTGACTGAGAGGCTATACG

TGGGAGGGCCCATGCTCAATAGCAAAGGCCAGACCTGCGGGTACAGGC

GTTGCCGCGCCAGCGGGGTGCTCACCACTAGCATGGGAAACACCATTA

CGTGCTATGTGAAAGCTCTAGCGGCATGCAAGGCCGCAGGGATAGTAG

CGCCCACGATGCTGGTATGCGGCGACGACCTGGTCGTCATCTCAGAAA

GCCAGGGGACTGAGGAGGACGAGCGGAACCTGAGAGTCTTCACGGAGG

CTATGACCAGGAATTCCGCC-3'.

An example of an amplicon with a length of 401 bp obtained from a viral strain 3a, with reference #PTR9058 has the sequence:

(SEQ ID NO: 14)
5'-TGGGGATCCCGTATGATACCCGCTGCTTTGACTCGACTGTCACTG

AACAGGATATCAGGGTGGAAGAGGAGATATACCAATGCTGTAATCTTG

AACCGGAGGCCAGGAAGGTGATCTCCTCCCTCACGGAGCGGCTTTACT

GCGGGGGTCCTATGTTCAACAGCAAAGGGGCCCAGTGTGGTTATCGCC

GTTGCCGTGCTAGTGGAGTTCTACCTACCAGCTTCGGCAATACAATCA

CTTGCTACATCAAGGCCACAGCGGCTGCAAGGGCCGCAGGCCTCCGGA

ACCCGGACTTTCTTGTCTGCGGAGACGATCTAGTCGTGGTGGCTGAGA

GTGACGGCGTCGACGAGGATGGGGCGGCCCTGAGAGCCTTCACGGAGG

CTATGACCAGGAATTCCGCC-3'.

An example of an amplicon with a length of 401 bp obtained from a viral strain 4a/4d, with reference #PTR4162 has the sequence:

(SEQ ID NO: 32)
5'-TGGGGATCCCGTATGATACCCGCTGCTTTGACTCCACTGTAACCG

AAAGAGACATCAGGGTCGAGGAGGAGGTCTATCAGTGTTGTGACCTAG

AGCCCGAAGCCCGCAAGGTAATATCCGCCCTCACAGAGAGACTCTACG

TGGGCGGTCCCATGTACAACAGCAGGGGAGACCTTTGCGGAACTCGAC

GGTGCCGTGCAAGCGGCGTATTCACCACCAGCTTTGGGAACACACTGA

CGTGCTATCTTAAGGCCAGCGCGGCCATCAGGGCTGCAGGCCTAAAGG

ACTGCACCATGCTGGTCTGTGGCGACGACTTAGTCGTTATCGCTGAAA

GCGATGGCGTGGAGGAGGACAACCGTGCGCTCAGAGCCTTCACGGAGG

CTATGACCAGGAATTCCGCC-3'.

To complement these long amplicons, other primers were designed in order to generate shorter amplicons starting from each of the plasma samples described above. The same overall protocol is followed to generate the "short" amplicons, and only the primers used have changed. The primers used are selected according to the genotype and/or subtype of HCV that has infected the patients.

Specific amplicons of the HCVs of subtype 1a/1b, with a size of 191 nucleotides are amplified with the following primers:
Biotinylated sense primer "1a/1b sense", of sequence 5'-[Btn]-TGA-CRA-CYA-GCT-GYG-GTA-AYA-CCC-T-3' (or [Btn]-SEQ ID NO: 10), and
Antisense primer "HCVantisense" of SEQ ID NO: 9 (see above).

An example of a short amplicon of 191 nucleotides obtained from a viral strain 1a/1b, with reference #PTR6719 has the sequence:

(SEQ ID NO: 13)
5'-TGACGACCAGCTGCGGTAATACCCTCACATGTTACTTGAAGGCCT

CTGCGGCCTGTCGAGCTGCAAAGCTCCAGGACTGCACAATGCTCGTGT

-continued
GCGGAGACGACCTTGTCGTTATCTGTGAAAGCGCGGGAACCCARGAGG

ATGCGGCGAGCCTACGAGTCTTCACGGAGGCTATGACCAGGAATTCCG

CC -3'.

Specific amplicons of the HCVs of subtype 2, with a size of 108 nucleotides are amplified with the following primers:
Biotinylated sense primer "biotinylated HCV 2 sense", of sequence 5'-[Btn]-ATG-YTG-GTR-TGC-GGC-GAC-GAC-3' (or [Btn]-SEQ ID NO: 29), and
Antisense primer "HCVantisense" of SEQ ID NO: 9 (see above).

An example of a short amplicon of 108 nucleotides obtained from a viral strain 2, with reference #PTR7761 has the sequence:

(SEQ ID NO: 33)
5'-ATGCTGGTATGCGGCGACGACCTGGTCGTCATCTCAGAAAGCCAG

GGGACTGAGGAGGACGAGCGGAACCTGAGAGTCTTCACGGAGGCTATG

ACCAGGAATTCCGCC -3'.

Specific amplicons of the HCVs of subtype 3a, with a size of 143 nucleotides are amplified with the following primers:
Biotinylated sense primer "HCV sense", SEQ ID NO: 8 (see above), and
Antisense primer "3a rev" of sequence: 5'-GCA-GTA-AAG-CCG-YTC-CGT-GAG-3' (SEQ ID NO: 11).

An example of a short amplicon of 143 nucleotides obtained from a viral strain 3a, with reference #PTR9058 has the sequence:

(SEQ ID NO: 15)
5'-TGGGGATCCCGTATGATACCCGCTGCTTTGACTCGACTGTCACTG

AACAGGATATCAGGGTGGAAGAGGAGATATACCAATGCTGTAATCTTG

AACCGGAGGCCAGGAAGGTGATCTCCTCCCTCACGGAGCGGCTTTACT

GC-3'.

Specific amplicons of the HCVs of subtype 4a/4d, with a size of 175 nucleotides are amplified with the following primers:
Biotinylated sense primer "HCV sense", SEQ ID NO: 8 (see above), and
Antisense primer "HCV antisense 4 rev" of sequence: 5'-AGG-TCT-CCC-YTG-CTG-TTG-TRC-AT-3' (SEQ ID NO: 30).

An example of a short amplicon of 175 nucleotides obtained from a viral strain 4a/4d, with reference #PTR4162 has the sequence:

(SEQ ID NO: 34)
5'-TGGGGATCCCGTATGATACCCGCTGCTTTGACTCCACTGTAACCG

AAAGAGACATCAGGGTCGAGGAGGAGGTCTATCAGTGTTGTGACCTAG

AGCCCGAAGCCCGCAAGGTAATATCCGCCCTCACAGAGAGACTCTACG

TGGGCGGTCCCATGTACAACAGCAGGGGAGACCT -3'.

As before, the "short" HCV amplicons obtained, with 191, 108, 175 and 143 nucleotides, are analysed by agarose gel electrophoresis, aliquots are taken and stored at −20° C. before use.

These amplicons, whose original viral genotypes are known, are stored in the form of a library.

2) Synthetic Targets: 15-Mer or 105-Mer Biotinylated Oligonucleotides 15-mer or 105-mer synthetic oligonucleotides biotinylated at the 5' end were synthesized.

The 15-mer synthetic oligonucleotides are strictly complementary to the HCV probes selected (see below), and have the following sequences:
the 15-mer synthetic oligonucleotides specific to subtype 1a/1b have the sequence: 5' [Btn]-GCT CCR GGA ACT GCA C-3' (or [Btn]-SEQ ID NO: 2);
the 15-mer synthetic oligonucleotides specific to subtype 3a have the sequence: [Btn]-CTT GAA CCG GAG GCC-3' (or [Btn]-SEQ ID NO: 5) and
the 15-mer synthetic oligonucleotides specific to subtype 4a/4d have the sequence: 5' [Btn]-CTA YGT GGG CGG YCC-3' (or [Btn]-SEQ ID NO: 39).

Longer oligonucleotides comprising the complementary sequence of the HCV probes presented below, framed on either side by sequences of 45 nucleotides, or 105 nucleotides in total, and biotinylated at the 5' end, were also synthesized for developing the probe/target hybridization tests.

The 105-mer synthetic oligonucleotides used have the following sequences:
the 105-mer synthetic oligonucleotides specific to subtype 1a/1b have the sequence: 5' [Btn]-CCT CAC TTG CTA CAT CAA GGC CCA GGC AGC CTG TCG AGC CGC AGG-GCT CCR GGA ACT GCA C-CAT GCT CGT GTG TGG CGA CGA CTT AGT CGT TAT CTG TGA AAG TGC-3' (or [Btn]-SEQ ID NO: 3); and
the 105-mer synthetic oligonucleotides specific to subtype 3a have the sequence: 5' [Btn]-GAA CAG GAC ATC AGG GTG GAA GAG GAG ATA TAC CAA TGC TGT AAC -CTT GAA CCG GAG GCC-AGG AAA GTG ATC TCC TCC CTC ACG GAG CGG CTT TAC TGC GGG GGC-3' (or [Btn]-SEQ ID NO: 6).

Design of the Oligonucleotide Probes for Recognition of HCV Sequences

The NS5b region encoding the RNA polymerase of HCV was targeted for designing the oligonucleotide probes of the invention.

The HCV genome sequences amplified in the NS5b region (representative bank of 800 samples) were determined and analysed using the clustalW2 alignment software and Mega5 phylogeny software in order to identify the most conserved zones for each genotype and/or subtype of HCV. Separate regions permitting generic recognition of the viral sequences of a genotype and optionally of a given subtype were selected. A highly conserved region permitting specific detection of all the HCVs of viral genotype 1a/1b was thus identified and selected. In the same way, a region permitting specific detection of the HCVs of viral genotype 2, 2a/2c, 2b, 3a and 4a/4d was identified and selected. Complementary 15-mer oligonucleotides of each of the regions selected were designed and multi-thiol oligonucleotides were then synthesized based on the sequences selected for specific recognition of the subtypes 1a/1b, 2, 2a/2c, 2b, 3a and 4a/4d.

The oligonucleotide sequence retained for generating probe 1a/1b is: 5'-GTG-CAG-TCC-YGG-AGC (SEQ ID NO: 1). This probe is specific to the strains of subtype 1a and 1b.

The oligonucleotide sequence retained for generating probe 2 is: 5'-TGG-CTY-TCT-GAG-ATG (SEQ ID NO: 27). This probe is specific to the strains of subtype 2.

The oligonucleotide sequence retained for generating probe 2a/2c is: 5'-GGA-CTC-CTC-RGT-TCT (SEQ ID NO: 35). This probe is specific to the strains of subtype 2a and 2c.

The oligonucleotide sequence retained for generating probe 2b is: 5'-TAT-GGA-TTC-TTC-TGT (SEQ ID NO: 36). This probe is specific to the strains of subtype 2b.

The oligonucleotide sequence retained for generating probe 3a is: 5'-GGC-CTC-CGG-TTC-AAG (SEQ ID NO: 4). This probe is specific to the strains of subtype 3a.

The oligonucleotide sequence retained for generating probe 4a/4d is: 5'-GGR-CCG-CCC-ACR-TAG (SEQ ID NO: 28). This probe is specific to the strains of subtypes 4a and 4d.

Evaluation of the Probe/Target Hybridizations by ELOSA (Enzyme-Linked Oligosorbent Assay)

Grafting of any type of thiol probes (alpha-anomer or beta-anomer oligonucleotides, linear or stem-loop probes ("snails"), etc.) may be carried out according to the following optimized protocol. The maleimide-activated microplate wells (Pierce) are washed with WB1 buffer (0.1M $Na_2HPO_4$, 0.15M NaCl, 0.05% Tween 20 (w/v), pH 7.2). Functionalization of the wells is carried out with 100 nM of multi-thiol probes (as described above) in BB buffer (0.1M $Na_2HPO_4$, 0.15M NaCl, 10 mM EDTA, pH 7.2) for 2 hours at ambient temperature (AT). The wells are then washed three times with WB1 saturated with 10 $\mu g \cdot mL^{-1}$ cysteine-HCl solution in BB (Pierce) for 1 hour at AT, and washed again three times with WB1.

The hybridization tests are carried out with short 15-mer or 105-mer synthetic targets or with real HCV amplicons: long (401 nt) or shorter (191 nt or 143 nt). The synthetic targets and the amplicons are diluted in 150 µL of hybridization buffer (HB: 0.9M NaCl, 60 mM $NaH_2PO_4$, 6 mM EDTA, pH 7.4, Denhardt 5×) before being deposited in the wells. An additional denaturation step of 10 min at 95° C. is carried out on the amplicons before transfer to the microwells. Hybridization is carried out overnight at 37° C. The wells are washed with WB2 buffer (0.75M NaCl, 50 mM $NaH_2PO_4$, 5 mM EDTA, pH 7.4, SDS 0.1%) three times for 2 min at AT and once for 30 min at 50° C.

The detection step is carried out after incubation for 30 min at AT of the wells in the presence of 100 µL/well of Streptavidin-Europium (Perkin Elmer) diluted in 100 of assay buffer ("Assay Buffer", Perkin Elmer). The wells are finally washed six times with WB3 buffer (WB1X, Perkin Elmer), and 200 µL of signal development buffer ("Enhancement Buffer", Perkin Elmer) is added to each well for 5 min at AT. The time-resolved fluorescence is measured on a Victor3™ 1420 multi-labelling detector ("multilabel counter", Perkin Elmer) according to the manufacturer's protocol (excitation at 340 nm and emission at 615 nm).

Results 1: Hybridization Tests on Beta-Anomeric Linear Probes Having 4 Thiol Functions Beta-anomeric linear 3a probes having 4 thiol functions are grafted, at a density of 100 nM, on a support covered with maleimide groups according to the protocol described above. The results obtained with the 3a probes are presented in FIGS. 8, and 9.

ELOSA tests are carried out, varying the nature and concentration of the target used (short 15-mer and 105-mer synthetic targets, short amplicons of 143 nt or 191 nt, long amplicons of 401 nt), in order to verify the specificity of the probes retained.

Figure 8:
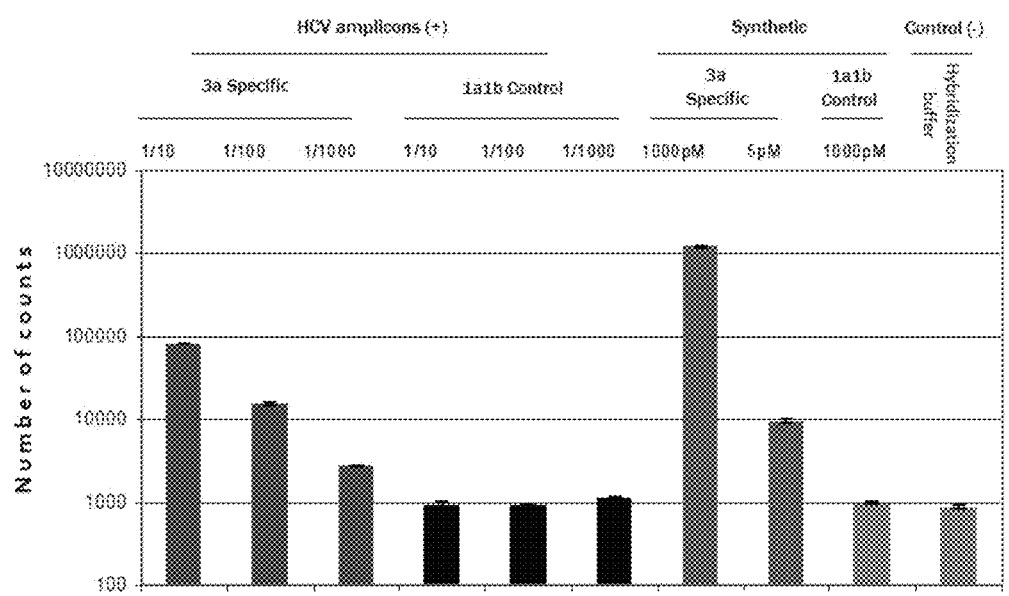

The results presented in FIG. 8 correspond to an ELOSA test carried out with long amplicons specific to the HCV 3a genotype, at dilutions of 1/10, 1/100 and 1/1000 and with non-specific long amplicons (corresponding to the HCV 1a/1b genotype) at dilutions of 1/10, 1/100 and 1/1000. The positive control of hybridization is carried out with a synthetic target (15-mer) specific to the 3a genotype at concentrations of 1000 pM and 5 pM. The negative controls of hybridization are carried out with a synthetic target (15-mer) that is non-specific (corresponding to the 1a/1b target sequence) at a concentration of 1000 pM, or with HB (hybridization buffer) alone, not comprising a target.

For the 3a probe to be regarded as "specific" to the 3a subtype, it is therefore necessary for the results obtained with "3a" targets to exceed the background noise obtained with the negative controls, so that the probe/target hybridization can be quantified.

Figure 9:
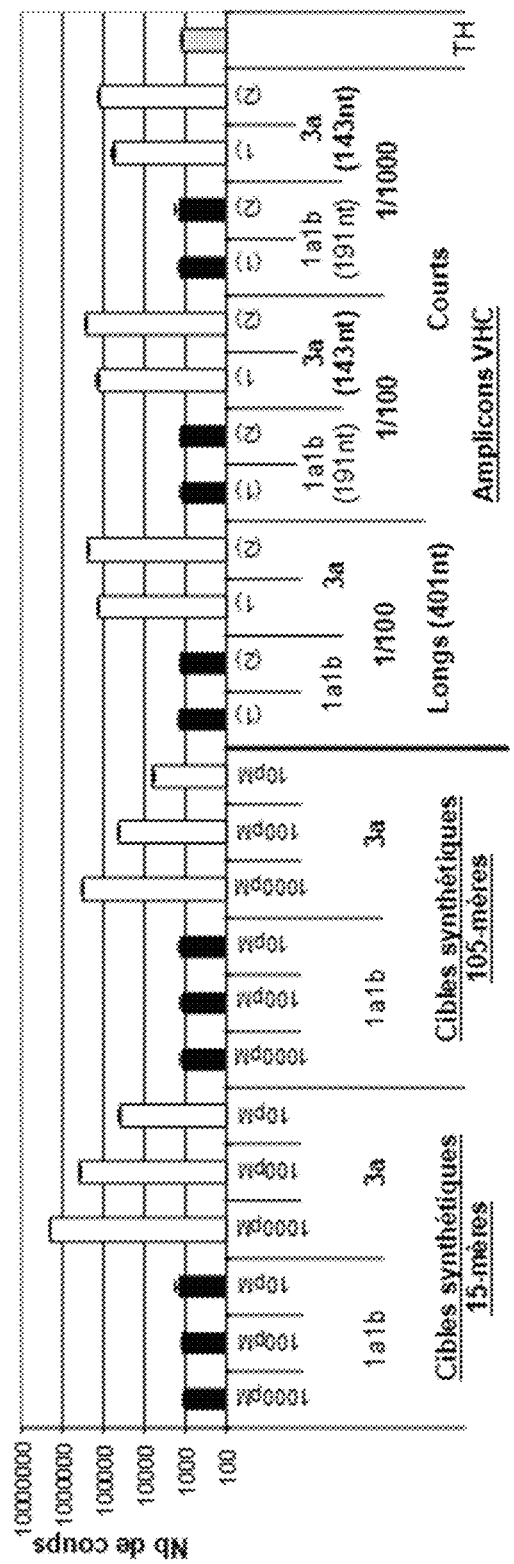

The results presented in FIG. 9 correspond to an ELOSA test carried out with the following targets:
- 15-mer or 105-mer specific 3a synthetic target, at a concentration of 10 pM, 100 pM or of 1000 pM,
- 15-mer or 105-mer non-specific 1a/1b synthetic target (negative control), at a concentration of 10 pM, 100 pM or of 1000 pM,
- 3a specific long amplicon, at dilution 1/100,
- 1a/1b non-specific long amplicon, at dilution 1/100,
- 3a specific short amplicon (143 nt), at dilutions 1/100 and 1/1000,
- 1a/1b non-specific short amplicon (191 nt), at dilutions 1/100 and 1/1000,
- HB alone, not comprising a target.

The results obtained in FIGS. 8, and 9 show that the "3a" probe according to the present invention is not only capable of hybridizing to 3a-specific synthetic targets, 15-mer (target having a concentration of 5 pM) or 105-mer (target having a concentration of 10 pM), but also to long amplicons of 401 nt or short amplicons of 143 nt obtained from plasmas genotyped 3a, and therefore specific to the 3a genotype (at 1/1000th dilution). These results also show that the 1a/1b targets, not specific to the 3a probe, do not hybridize detectably with the latter, regardless of their form (15-mer or 105-mer synthetic target, short amplicon 191 nt or long amplicon 401 nt), or their concentration (1000 pM for the synthetic targets or 1/10th dilution for the amplicons).

Figure 10:
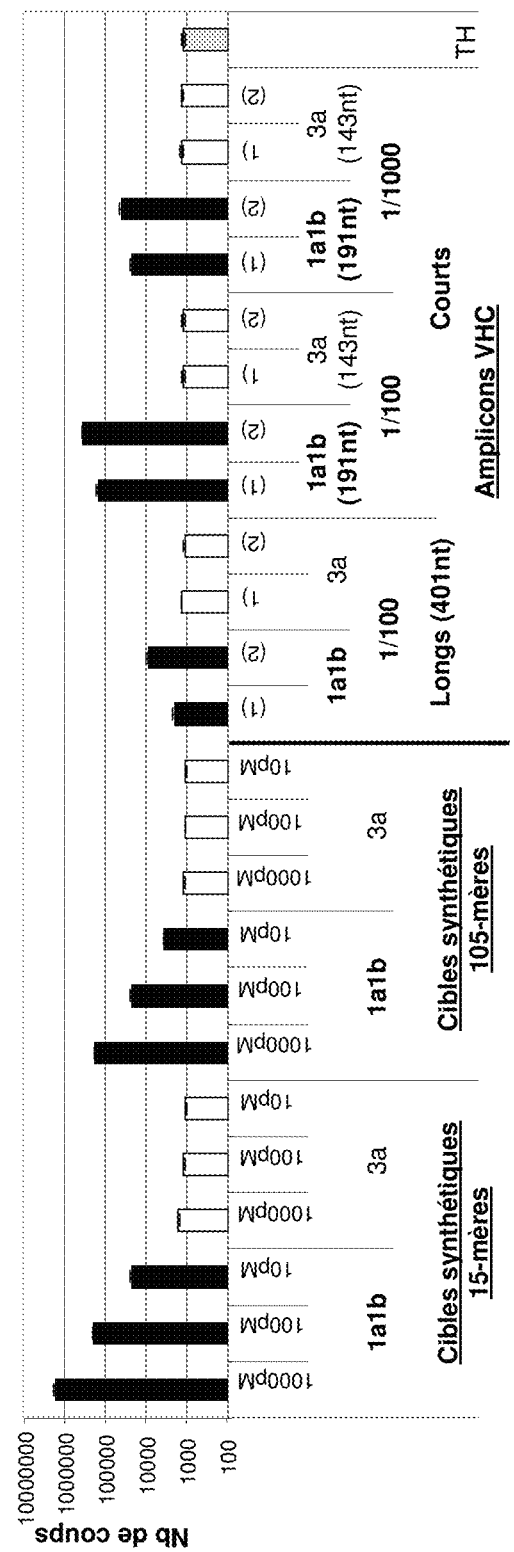
FIG. 10 shows a schematic diagram of the results of ELOSA tests with fluorescence detection, carried out with a tetrathiol probe of type 1a/1b.

The results presented in FIG. 10 correspond to an ELOSA test carried out with 1a/1b linear probes (see above), beta-anomeric, having 4 thiol functions, which are grafted at a density of 100 nM on a support covered with maleimide groups according to the protocol described above.

The results in FIG. 10 are obtained from the following targets:
- 15-mer or 105-mer 1a/1b specific synthetic target, at a concentration of 10 pM, 100 pM or 1000 pM,
- 15-mer or 105-mer 3a non-specific synthetic target (negative control), at a concentration of 10 pM, 100 pM or 1000 pM,
- long amplicon specific to the 1a/1b HCV genotype, at dilution 1/100,
- 3a non-specific long amplicon, at dilution 1/100,
- 1a/1b specific short amplicon (191 nt), at dilutions 1/100 and 1/1000,
- 3a non-specific short amplicon (143 nt), at dilutions 1/100 and 1/1000,
- HB alone, not comprising a target.

The results obtained in FIG. 10 show that the 1a/1b probe according to the present invention is not only capable of hybridizing with 15-mer or 105-mer synthetic targets specific to 1a/1b (the target having a concentration of 10 pM), but also to short amplicons of 191 nt obtained from plasmas genotyped 1a/1b, and therefore specific to genotype 1a/1b (at 1/1000th dilution), and to long amplicons of 401 nt specific to genotype 1a/1b (at 1/100th dilution).

These results also show that the 3a targets, non-specific to the 1a/1b probe, do not hybridize detectably to the latter, regardless of their form (15-mer or 105-mer synthetic target, short amplicon 143 nt or long amplicon 401 nt), or their concentration (1000 pM for the synthetic targets or 1/10th dilution for the amplicons).

Figure 17:
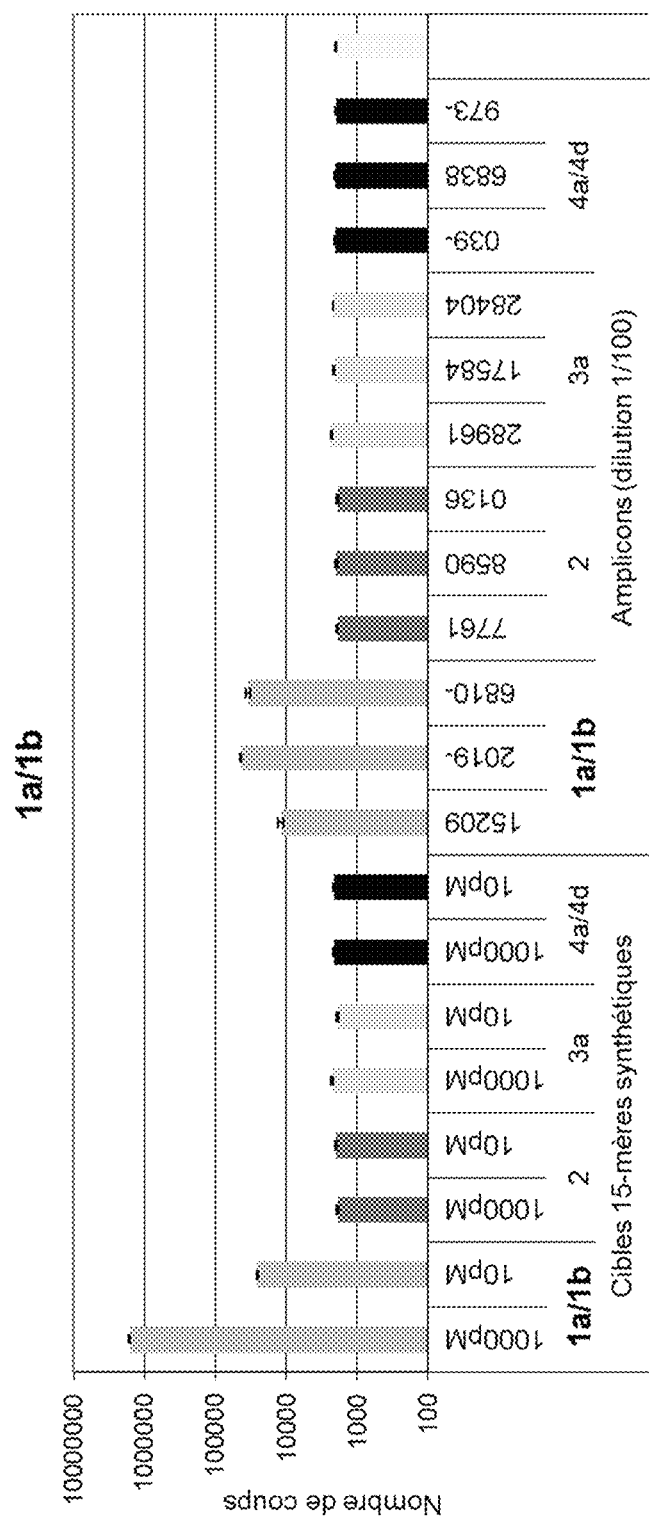
FIG. 17 shows a schematic diagram of the results of ELOSA tests with fluorescence detection, carried out with a tetrathiol HCV probe of type 1a/1b.

The results presented in FIG. 17 correspond to an ELOSA test carried out with a beta-anomeric linear 1a/1b probe having 4 thiol functions, which is grafted at a density of 100 nM on a support covered with maleimide groups according to the protocol described above.

The results in FIG. 17 are obtained from the following targets:
- 15-mer 1a/1b specific synthetic target at a concentration of 10 pM or 1000 pM,
- 15-mer 2a/2c, 2b, 3a or 4a/4d non-specific synthetic target (negative control), at a concentration of 10 pM or 1000 pM,
- long amplicon specific to the 1a/1b HCV genotype, at dilution 1/100,
- 2a/2c, 2b, 3a or 4a/4d non-specific long amplicon at dilution 1/100,
- HB alone, not comprising a target.

Figure 18:
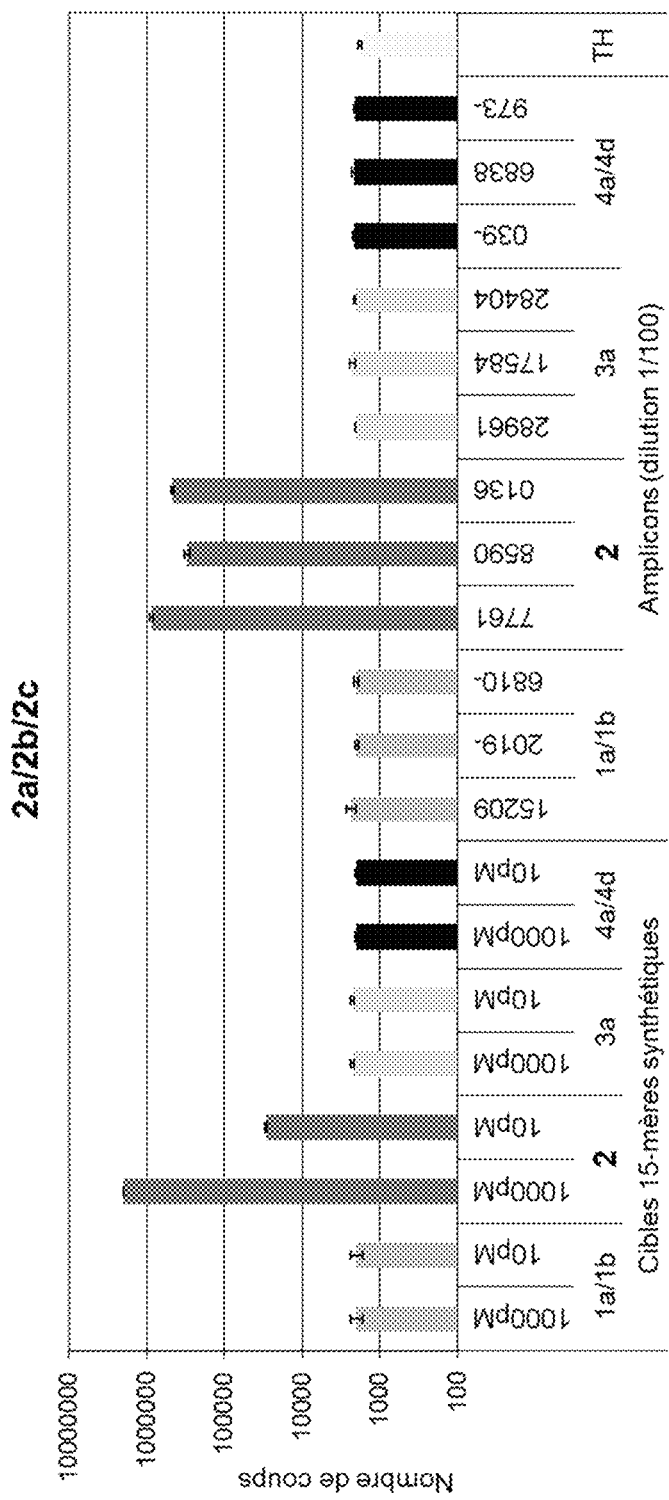
FIG. 18 shows a schematic diagram of the results of ELOSA tests with fluorescence detection, carried out with a mixture of two tetrathiol HCV probes of types 2a/2c and/2b.

The results presented in FIG. 18 correspond to an ELOSA test carried out with a mixture of two beta-anomeric linear probes (2a/2c of SEQ ID NO: 35 and 2b of SEQ ID NO: 36) having 4 thiol functions, which are grafted at a density of 50 nM each on a support covered with maleimide groups according to the protocol described above.

The results in FIG. 18 are obtained from the following targets:
- 15-mer 2a/2c and 2b specific synthetic targets at a concentration of 10 pM or 1000 pM,
- 15-mer 1a/1b, 3a or 4a/4d non-specific synthetic target (negative control), at a concentration of 10 pM or 1000 pM,
- long amplicon specific to the 2a/2b/2c HCV genotype, at dilution 1/100,
- 1a/1b, 3a or 4a/4d non-specific long amplicon at dilution 1/100,
- HB alone, not comprising a target.

Figure 19:
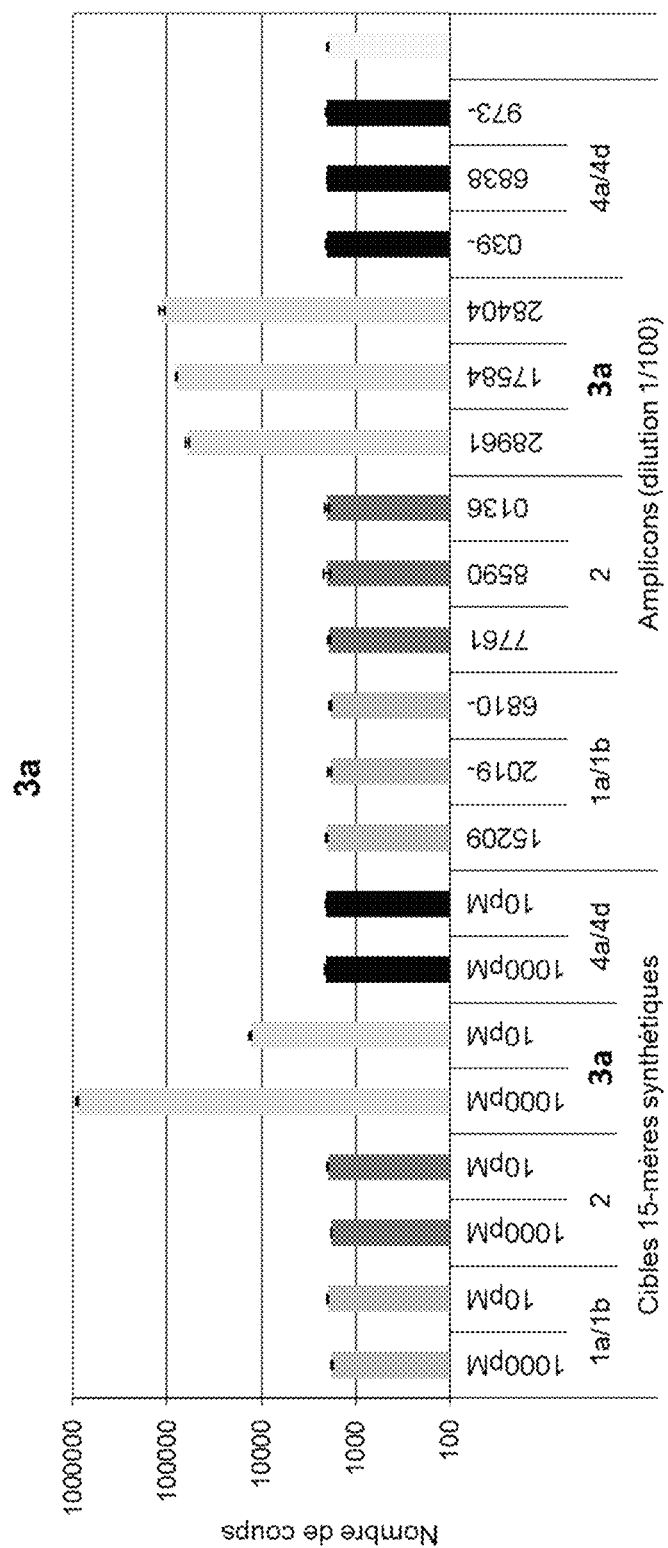

The results presented in FIG. 19 correspond to an ELOSA test carried out with a beta-anomeric linear 3a probe having 4 thiol functions, which is grafted at a density of 100 nM on a support covered with maleimide groups according to the protocol described above.

The results in FIG. 19 are obtained from the following targets:
- 15-mer 3a specific synthetic target, at a concentration of 10 pM or 1000 pM,
- 15-mer 1a/1b, 2a/2b/2c or 4a/4d non-specific synthetic target (negative control), at a concentration of 10 pM or 1000 pM,
- long amplicon specific to the 3a HCV genotype, at dilution 1/100,
- 1a/1b, 2a/2b/2c or 4a/4d non-specific long amplicon at dilution 1/100,
- HB alone, not comprising a target.

Figure 20:
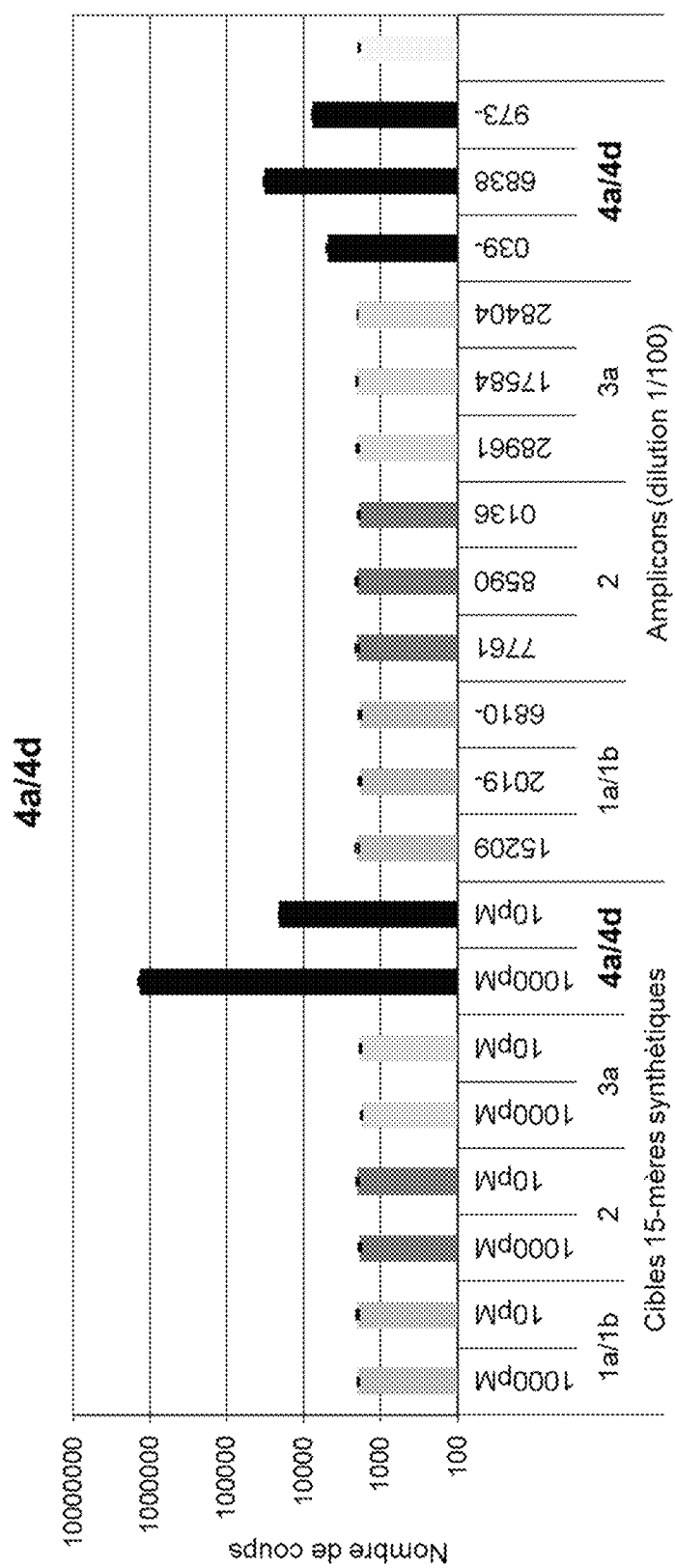
FIG. 20 shows a schematic diagram of the results of ELOSA tests with fluorescence detection, carried out with a tetrathiol HCV probe of type 4a/4d.

The results presented in FIG. 20 correspond to an ELOSA test carried out with a beta-anomeric linear 4a/4d probe having 4 thiol functions, which is grafted at a density of 100 nM on a support covered with maleimide groups according to the protocol described above.

The results in FIG. 20 are obtained from the following targets:
- 15-mer 4a/4d specific synthetic target at a concentration of 10 pM or 1000 pM,
- 15-mer 1a/1b, 2a/2b/2c or 3a non-specific synthetic target (negative control), at a concentration of 10 pM or 1000 pM,
- long amplicon specific to the 4a/4d HCV genotype, at dilution 1/100,
- 1a/1b, 2a/2b/2c or 3a non-specific long amplicon at dilution 1/100,
- HB (hybridization buffer) alone, not comprising a target.

For the tests carried out using amplicons, the results of 3 independent trials carried out starting from viral strains of different origins, but of the same subtype, are presented in FIGS. 17 to 20.

The results presented in FIGS. 17 to 20 show that each of the probes 1a/1b, 2a/2c, 2b, 3a or 4a/4d according to the present invention is not only capable of hybridizing with 15-mer synthetic targets that are specific to it (the target having a concentration of 10 pM), but also with specific amplicons of the same genotype (at 1/100th dilution). These results also show that the non-specific targets do not hybridize detectably.

Results 2: Investigation of the Effect of the Number of Thiol Functions

ELOSA tests are also carried out varying the number of thiol functions in the probe used and testing different types and concentrations of targets (15-mer or 105-mer short synthetic target, short amplicons of 143 nt or 191 nt, long amplicons of 401 nt). The results presented in FIG. 11 correspond to an ELOSA test carried out with linear 1a/1b probes (see above), beta-anomeric, having 1, 2, 4, 6 or 8 thiol functions, which are grafted at a density of 100 nM on a support covered with maleimide groups according to the protocol described above. The results in FIG. 11 are obtained from the following targets:
- 15-mer or 105-mer 1a/1b specific synthetic target, at a concentration of 10 pM, 100 pM or 1000 pM,
- 15-mer or 105-mer 3a non-specific synthetic target (negative control), at a concentration of 10 pM, 100 pM or 1000 pM,
- HB alone, not comprising a target.

Each probe/target hybridization condition is tested in triplicate in a microplate. The tests are reproduced three times, completely from the step of grafting the probes to the detection of hybridization (on 3 different microplates). The results presented in the application therefore correspond to a mean value from 9 measurements.

Figure 11:
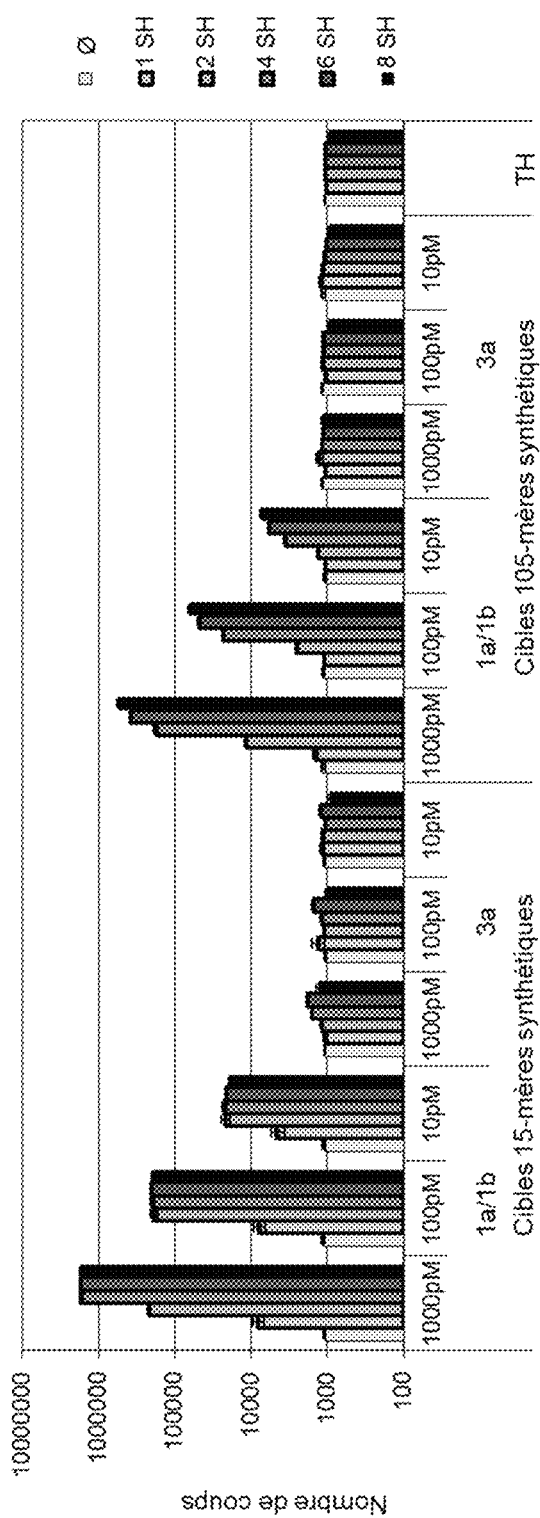
FIG. 11 shows a schematic diagram of the results of ELOSA tests with fluorescence detection, carried out with probes of type 1a/1b bearing 1, 2, 4, 6 or 8 thiol groups.

The results obtained in FIG. 11 show that the hybridization of a 15-mer 1a/1b specific synthetic target with the 1a/1b probe is detectable starting from 10 pM of target, once a thiol is present. Detection of the 105-mer 1a/1b specific synthetic target requires in its turn a concentration of target of 100 pM when the probe comprises 2 thiol functions or of 10 pM when the probe comprises 4, 6 or 8 thiol functions. No detectable hybridization is observed in the presence of the 3a targets, non-specific to the 1a/1b probe, regardless of their size (15-mer or 105-mer) or their concentration (maximum concentration tested: 1000 pM). The results thus show that adding thiol functions to the grafted oligonucleotide probe improves the performance of detection of the targets in question. The presence of 4 thiol functions in the probe used makes it possible to detect all the synthetic targets (15-mer or 105-mer) at a concentration of 10 pM.

Results 3: Investigation of the Effect of Grafting Density

Figure 12:
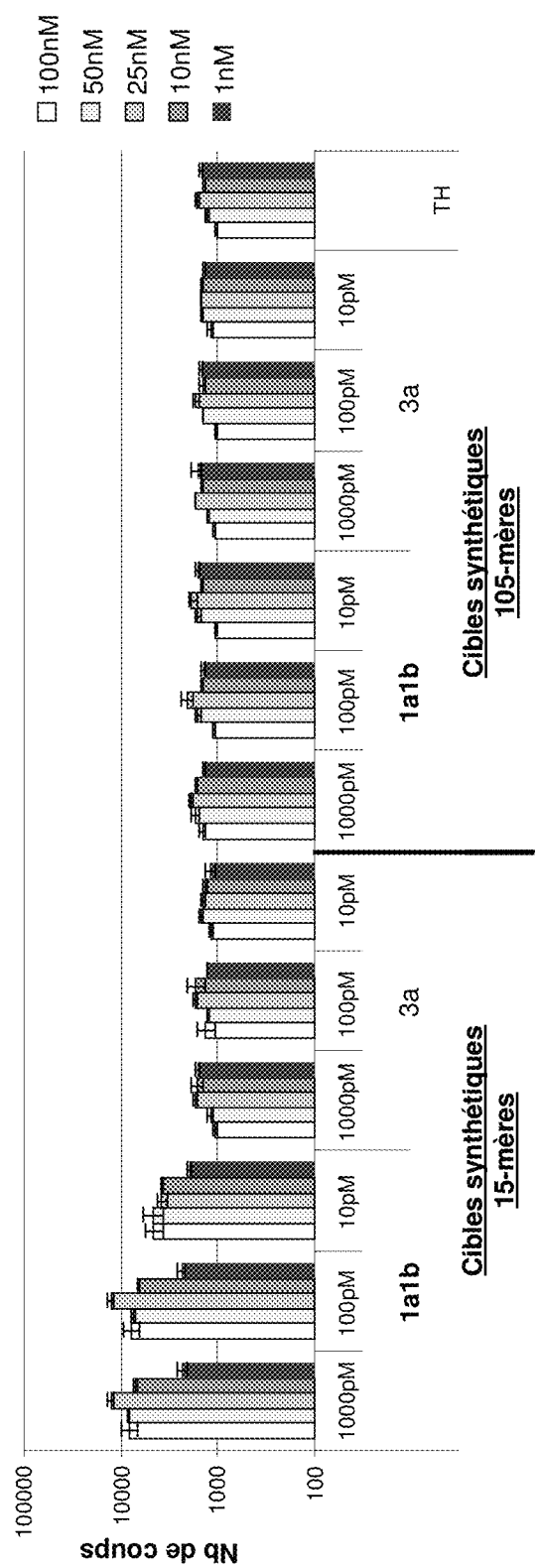
FIG. 12 shows a schematic diagram of the results of ELOSA tests with fluorescence detection, carried out with a monothiol probe of type 1a/1b at different grafting densities.
Figure 13:
FIG. 13 shows a schematic diagram of the results of ELOSA tests with fluorescence detection, carried out with a dithiol probe of type 1a/1b at different grafting densities.
Figure 14:
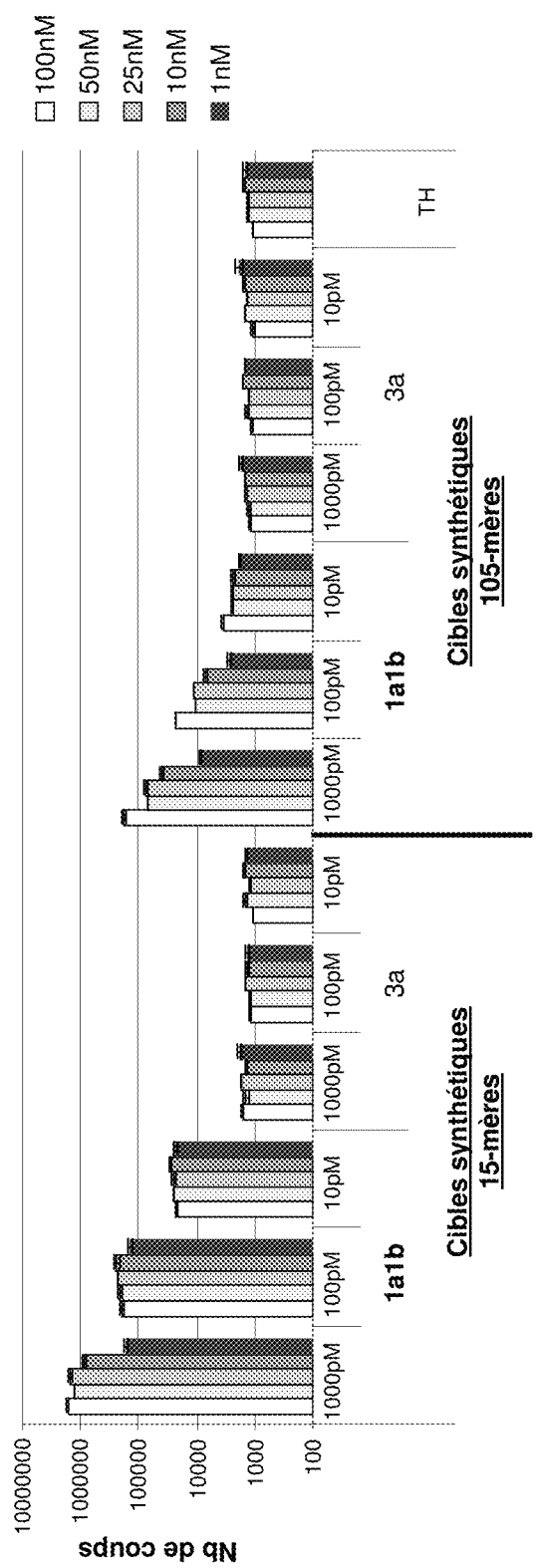
FIG. 14 shows a schematic diagram of the results of ELOSA tests with fluorescence detection, carried out with a tetrathiol probe of type 1a/1b at different grafting densities.

The results presented in FIGS. 12, 13 and 14 correspond to ELOSA tests carried out with beta-anomeric linear 1a/1b probes (see above), having 1, 2 or 4 thiol functions, which are grafted at densities of 1, 10, 25, 50 or 100 nM on a support covered with maleimide groups according to the protocol described above. FIG. 12 illustrates the results obtained for the monothiol probe, i.e. comprising a single thiol compound according to the invention. FIG. 13 illustrates the results obtained for the dithiol probe, i.e. comprising two thiol compounds according to the invention, and FIG. 14 illustrates the results obtained for the tetrathiol probe, i.e. comprising four thiol compounds according to the invention.

In each case, the hybridization tests are carried out with the following targets:
- 15-mer or 105-mer 1a/1b specific synthetic target, at a concentration of 1000 pM, of 100 pM or 10 pM,
- 15-mer or 105-mer 3a non-specific synthetic target (negative control), at a concentration of 1000 pM, of 100 pM or 10 pM,
- HB alone, not comprising a target.

The results presented in FIGS. 12, 13 and 14 confirm the specificity of hybridization of the 1a/1b probes with the 1a/1b targets, in that detectable hybridization is not observed in the presence of the 3a targets, independently of the concentration of the latter.

These results confirm (1) that the presence of a single thiol in the probe used does not allow targets to be detected having a size of 105 nt, (2) that starting from 2 thiol functions, it becomes possible to detect hybridization between the probe and the target of 105 nt (in particular starting from 100 pM of target), (3) that the best results are obtained with the tetrathiol probe.

On the other hand, it appears that the density of grafting of the monothiol probe does not have much influence on the hybridization signals whatever the targets (15-mer and 105-mer), whereas hybridization is dose-dependent of the grafting density in the case of the dithiol and tetrathiol probes. The best probe/target hybridization signals (15-mer and 105-mer) are obtained with the tetrathiol probe grafted at 100 nM.

Evaluation of the Probe/Target Hybridizations on an Electrode with a Gold Surface A hybridization test was carried out by grafting a 1a/1b specific probe sequence on an electrode with a gold surface.

A tetrathiol probe bearing an oligonucleotide of sequence SEQ ID NO: 1 was grafted on the working electrode with a gold surface of a cell. The hybridization of 105-mer 1a/1b specific targets (of SEQ ID NO: 3) was evaluated, for 3 different concentrations of targets: 1 pM, 10 pM and 100 pM. A negative control is carried out with a 105-mer 3a specific target of SEQ ID NO: 6 (negative control).

Figure 15:
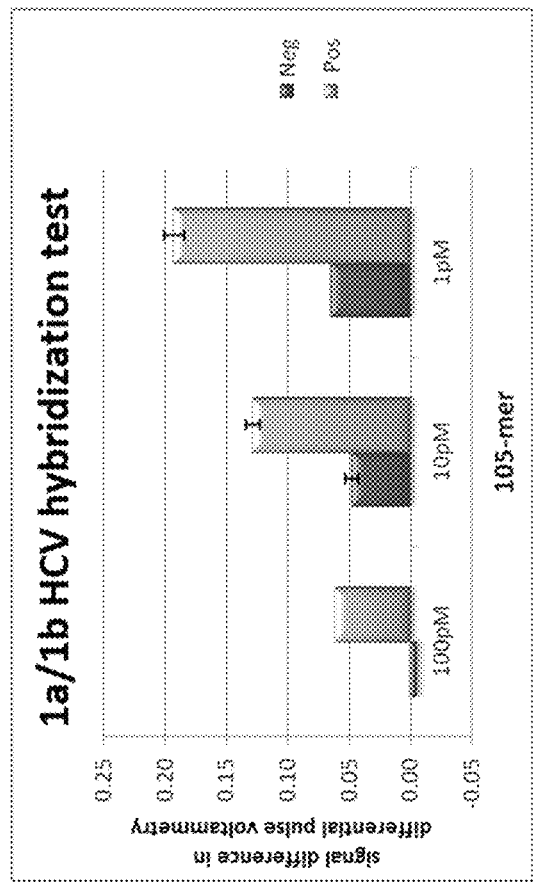
FIG. 15 shows the results of a probe/target hybridization test with a tetrathiol probe grafted on the gold surface.

The hybridization reaction is monitored by differential pulse voltammetry. The results obtained are presented in FIG. 15.

The values on the y-axis correspond to the normalized values of the change in current. The results obtained show that the hybridization test by electrochemistry is sensitive and specific at a concentration of targets of 1 pM. The variation in signal also appears to be greater at 1 pM than when the test is conducted at 100 pM. At a higher concentration of target, an effect of non-specific adsorption of the targets on the surface of the electrode reduces the efficacy of the recognition reaction. The electrochemical method does not allow quantitative monitoring of the hybridization reaction. Nevertheless, it supplies a specific yes/no response with very high sensitivity.

Example 4: Application to the Detection of Flaviviruses, Such as the Dengue and West Nile Viruses Known sequences of the dengue virus (serotypes 1, 2, 3 and 4) and of the West Nile virus were extracted from the GenBank database and analysed. Table 1 lists the GenBank accession numbers of the sequences of dengue and West Nile virus used for performing the alignments:

TABLE 1

| Virus | GenBank accession number of the sequences |
|---|---|
| Dengue 1 (8 strains) | FJ882517, FJ882552, EU482480, FJ639683, HM181967, AY726549, GU131762, GU131982 |
| Dengue 2 (17 strains) | GQ398257, HM582109, HM582110, HM582116, HM582117, AY744150, AY744149, AY744148, AY744147, EU056812, AF169686, AF169683, AF169687, AF169682, GU131896, DQ181803, EU073981 |
| Dengue 3 (34 strains) | GQ252678, GU131951, EU482566, GQ868574, GQ868617, FJ882577, GU131868, FJ024465, HM181974, HM181973, GQ199870, AY770511, GU370053, GQ199888, GU131939, GU131937, GU131934, HM631854, GU131905, GU189648, EU660409, DQ109373, DQ109368, DQ109310, AY676351, AY676350, FJ744740, FJ744730, DQ109400, DQ109348, GQ868593, AB214880, AY744677, EF629370 |
| Dengue 4 (20 strains) | AY618992, AY618990, AY858049, AY618993, GQ398256, AF289029, EU854301, EU073983, 289913, AF326573, FJ882597, GQ199885, GQ199884, GQ199882, GQ868582, GQ868584, AY762085, AY618989, AY618988, EF457906 |
| West Nile (15 strains) | GQ851607, GQ851606, AY369441, AY490240, AY274504, GQ851602, GQ851603, DQ256376, DQ318019, EF429199, EF429200, JN858070, AY277251, FJ159131, FJ159129 |

Design of the Oligonucleotide Probes for the Recognition of Dengue or West Nile Sequences Alignments and sequence comparisons carried out using the clustalW2 and Mega5 software allowed 4 regions to be defined, of which:
- 2 are conserved among all the strains of the dengue and West Nile viruses, as well as among other flaviviruses such as the Japanese encephalitis virus, tick-borne encephalitis virus, yellow fever virus and usutu virus (non limitative list),
- 1 is conserved among the dengue viruses,
- 1 is conserved among the West Nile viruses.

These regions were used for designing probes according to the present invention, with the aim of permitting generic detection of the flaviviruses, or specific detection of the dengue viruses, of dengue subtype 4 or of the West Nile virus, in a biological sample.

Probes 1 to 3 presented in Table 2 below thus allow detection of the flaviviruses generally (including the dengue and West Nile flaviviruses). Probe 4 is specific to the dengue viruses, regardless of the serotype. Probe 5 is specific to serotype 4 of the dengue viruses. Probe 6 is specific to the West Nile viruses.

TABLE 2

| Probe | Sequence | Specificity | Size | SEQ ID |
|---|---|---|---|---|
| Probe 1 | 5'-GCT CCC ARC CAC AT-3' | Generic | 14-mer | SEQ ID NO: 16 |

TABLE 2-continued

| Probe | Sequence | Specificity | Size | SEQ ID |
|---|---|---|---|---|
| Probe 2 | 5'-AAC CAT CTR TCT TC-3' | Generic | 14-mer | SEQ ID NO: 17 |
| Probe 3 | 5'-AGC CAC ATG WAC CA-3' | Generic | 14-mer | SEQ ID NO: 40 |
| Probe 4 | 5'-CTT CYC CTT CYA CTC-3' | Dengue | 15-mer | SEQ ID NO: 18 |
| Probe 5 | 5'-CAC TCC ACT CCA TGA-3' | Dengue 4 | 15-mer | SEQ ID NO: 41 |
| Probe 6 | 5'-CKC CTC CTG ART TCT-3' | West Nile Virus | 15-mer | SEQ ID NO: 19 |

Design of Targets for Testing the Recognition Specificity of Probes 1 to 6

Amplicons, each including the 6 regions identified, are prepared by carrying out a simple PCR, starting from the sequences mentioned in Table 1, using the primers and the protocol previously described by Scaramozzino et al. (Scaramozzino N. et al. Comparison of Flavivirus universal primer pairs and development of a rapid, highly sensitive heminested reverse transcription-PCR assay for detection of flaviviruses targeted to a conserved region of the NS5 gene sequences. 2001. Journal of Clinical Microbiology 39: 1922-1927).

Primary amplification by PCR is thus carried out with:
 the MAMD sense primer: [Btn]-5'-AAC-ATG-ATG-GGR-AAR-AGR-GAR-AA-3' (or [Btn]-SEQ ID NO: 20), and
 the cFD2 antisense primer (SEQ ID NO: 21): 5'-GTG-TCC-CAG-CCG-GCG-GTG-TCA-TCA-GC-3'.

This amplification leads to a primary amplicon of 263 bp being obtained.

When the viral load is very low, a secondary PCR is carried out using the amplification products resulting from the first PCR as matrix. This "heminested" PCR advantageously gives a significant gain in sensitivity.

An example of an amplicon of 263 bp obtained after amplification starting from the strain of dengue virus with the reference number FJ882517 has the sequence: 5'-AA-CATGATGGGGAAGAGAGAGAAAAAACTAG-GAGAGTTCGGAAAGGCAA AAGGAAGTCGTGCAATATGGTACATGTGGCTGG-GAGCACGCTTTCTAGAG TTCGAAGCTCTTGGTTT-CATGAACGAAGATCACTGGTTCAGCAGAGAGAA TTCACTCAGCGGAGTGGAAGGAGAAGGACTC-CACAAACTTGGATATATAC TCAGAGACATATCAAA-GATTCCAGGGGGAAACATGTATGCAGATGACACA GCCGGATGGGACAC-3' (SEQ ID NO: 23).

An example of an amplicon of 263 bp obtained after amplification starting from the strain of West Nile virus with the reference number EF429200/H442 has the sequence:

(SEQ ID NO: 25)
5'-AACATGATGGGAAAGAGAGAGAAGAAGCCTGGAGAGTTCGGCAAG

GCTAAAGGCAGCAGAGCCATCTGGTTCATGTGGCTGGGGGCTCGTTTC

CTGGAGTTTGAAGCTCTCGGATTCCTCAATGAAGACCACTGGCTGGGT

AGGAAGAACTCAGGAGGAGGAGTTGAAGGCTTAGGACTGCAGAAGCTT

GGGTACATCTTGAAGGAAGTTGGGACAAAGCCTGGAGGAAAGATTTAC

GCCGATGATACCGCAGGCTGGGACAC-3'.

A secondary amplification by PCR may then optionally be carried out according to the protocol published by Scaramozzino et al., using the above primary amplicons as matrix with:
 the FS778 sense primer: [Btn] 5'-AAR-GGH-AGY-MCD-GCH-ATH-TGG-T-3' (or [Btn]-SEQ ID NO: 22), and
 the cFD2 antisense primer (SEQ ID NO: 21): 5'-GTG-TCC-CAG-CCG-GCG-GTG-TCA-TCA-GC-3'.

This amplification leads to a secondary amplicon of 215 bp being obtained.

An example of an amplicon of 215 bp obtained after amplification starting from the strain of dengue virus with the reference number FJ882517 has the sequence: 5'-AAAGGAAGTCGTGCAATATGGTA-CATGTGGCTGGGAGCACGCTTTCTAGA GTTCGAAGCTCTTGGTTTCATGAACGAAGAT-CACTGGTTCAGCAGAGAGA ATTCACTCAGCG-GAGTGGAAGGAGAAGGACTCCACAAACTTGGA-TATATA CTCAGAGACATATCAAAGATTCCAGGGGGAAA-CATGTATGCAGATGACAC AGCCGGATGGGACAC-3' (SEQ ID NO: 24).

An example of an amplicon of 215 bp obtained after amplification starting from the strain of West Nile virus with the reference number EF429200/H442 has the sequence:

(SEQ ID NO: 26)
5'-AAAGGCAGCAGAGCCATCTGGTTCATGTGGCTGGGGGCTCGTTTC

CTGGAGTTTGAAGCTCTCGGATTCCTCAATGAAGACCACTGGCTGGGT

AGGAAGAACTCAGGAGGAGGAGTTGAAGGCTTAGGACTGCAGAAGCTT

GGGTACATCTTGAAGGAAGTTGGGACAAAGCCTGGAGGAAAGATTTAC

GCCGATGATACCGCAGGCTGGGACAC-3'.

In another embodiment, the amplicons are prepared from viral RNAs of flaviviruses, of dengue or of West Nile virus by asymmetric RT-PCR. Viral RNAs are extracted from dengue virus (1-4) and West Nile virus (of American origin NY or African Af) produced in vitro. Amplicons of 263 bp are produced from the NS5 viral region of the flaviviruses, by RT-PCR starting from each of the samples of RNA described above. In order to carry out the reverse-transcription (AT) step, 5 µl of RNA is denatured at 72° C. for 10 minutes and reverse-transcribed in the presence of 4 µl, of 5× First Strand Buffer (Invitrogen), 2 µL of 10× Hexanucleotide Mix (Roche), 2 µL of 10 mM dNTP mix (Invitrogen) and 200 U of SuperScript® II Reverse Transcriptase (Invitrogen) in a total volume of 20 µL. The reverse-transcription conditions are as follows: 10 min at 25° C., 60 min at 42° C., and 10 min at 95° C. Five microlitres of cDNA are then amplified by PCR (polymerase chain reaction) using the primers:
 biotinylated "MAMD" sense flavivirus (of sequence: [Btn]-AAC ATG ATG GGR AAR AGR GAR AA (or [Btn]-SEQ ID NO: 20)) and
 "cFD2" antisense flavivirus (of sequence GTG TCC CAG CCG GCG GTG TCA TCA GC (SEQ ID NO: 21)) (see Scaramozzino N. et al. 2001, Journal of Clinical Microbiology 39: 1922-1927).

The asymmetric amplification reaction is carried out in 50 µl, of reaction mixture comprising: 1×PCR Buffer without MgCl$_2$ (Invitrogen), 0.2 µM of MAMD, 0.02 µM of cFD2, 1.5 mM MgCl$_2$ (Invitrogen), 0.2 mM dNTP mix (Invitrogen) and 1.5 U Taq Polymerase (Invitrogen). The PCR conditions are as follows: 5 min at 95° C., 40 cycles (denaturation: 40 sec, 94° C.; hybridization: 40 sec, 53° C.; elongation: 50 sec, 72° C.), and a final extension of 10 min at 72° C. The amplicons obtained are analysed by agarose gel electrophoresis; aliquots are taken and stored at −20° C. before use. These amplicons, whose original viral genotypes are known, are stored in the form of a library.

15-mer synthetic oligonucleotides biotinylated at the 5' end were synthesized. These oligonucleotides are strictly complementary to the probes selected above, i.e. to the generic probe 3 for detecting the flaviviruses, to the generic probe for detecting the West Nile virus and to the probe specific to serotype 4 of the dengue virus. These synthetic oligonucleotides have the following sequences:

The 14-mer synthetic oligonucleotides specific to the flaviviruses have the sequence: 5' [Btn]-TGG TWC ATG TGG CT-3' (or [Btn]-SEQ ID NO: 43);

The 15-mer synthetic oligonucleotides specific to the West Nile virus have the sequence: 5' [Btn]-AGA AYT CAG GAG GMG-3' (or [Btn]-SEQ ID NO: 42) and The 15-mer synthetic oligonucleotides specific to serotype 4 of the dengue virus have the sequence: 5' [Btn]-TCA TGG AGT GGA GTG-3' (or [Btn]-SEQ ID NO: 44).

Figure 22:
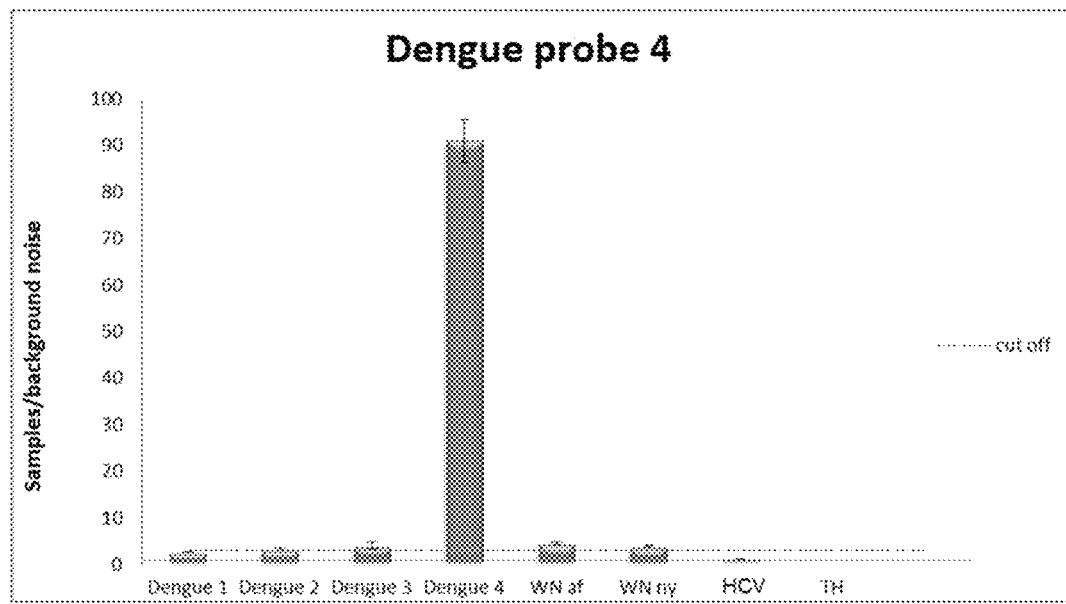
FIG. 22 shows a schematic diagram of the results of ELOSA tests with fluorescence detection, carried out with a tetrathiol probe specific to serotype 4 of dengue.
Figure 23:
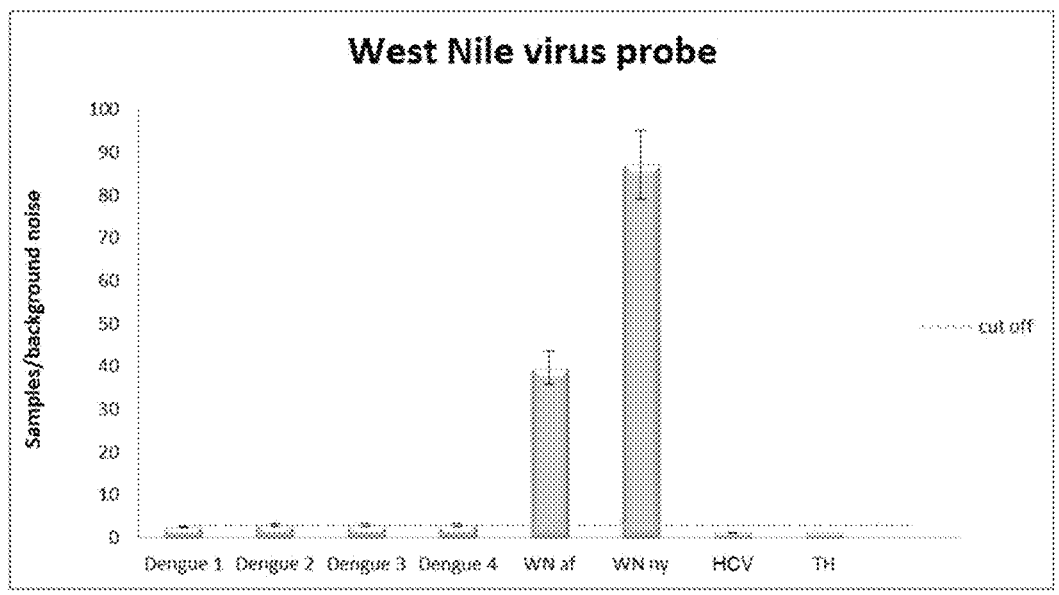
FIG. 23 shows a schematic diagram of the results of ELOSA tests with fluorescence detection, carried out with a tetrathiol probe that is generic for the West Nile virus.

Hybridization tests are carried out with probe 3 generically recognizing the flaviviruses (see FIG. 21), probe 5 specifically recognizing serotype 4 of dengue (see FIG. 22) and probe 6 recognizing the West Nile virus (see FIG. 23). The probes, having 4 thiol functions, are grafted at a density of 200 nM on a support covered with maleimide groups according to the protocol described above. ELOSA tests are then carried out using amplicons prepared from serotypes 1, 2, 3 or 4 of dengue, of West Nile virus of American origin (NY) or African (Af), or of hepatitis C virus (long 3a amplicon), at a dilution of 1/10 for probe 3 and of 1/50 for probes 5 and 6 in order to verify the specificity of the probes retained. In the diagrams in FIGS. 21, 22 and 23, the value "samples/background noise" is obtained by calculating the ratio of the number of counts measured for each sample to the number of counts measured for the control (HB), corresponding to the hybridization buffer alone, not comprising a target. The amplicons of dengue virus and of West Nile virus used in these tests were obtained by the method of asymmetric RT-PCR described above.

Figure 21:
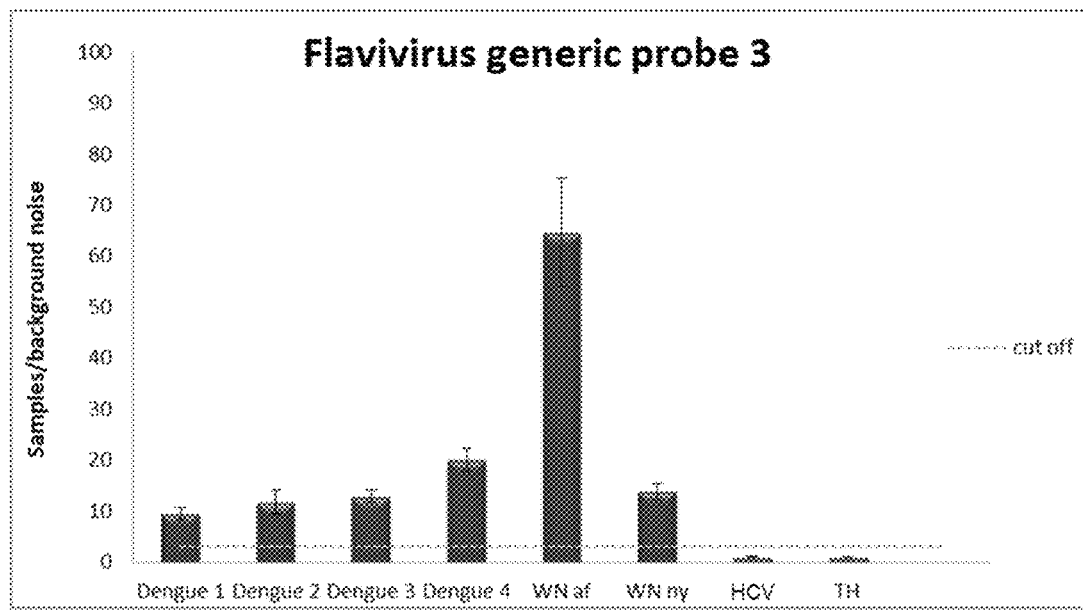
FIG. 21 shows a schematic diagram of the results of ELOSA tests with fluorescence detection, carried out with a tetrathiol probe that is generic for the flaviviruses.

The results presented in FIGS. 21, 22 and 23 show that the flavivirus generic probe, the dengue specific probe 4 and the West Nile virus generic probe only hybridize significantly to the amplicons that correspond to the virus in question.

What is claimed is:

1. A modified oligonucleotide corresponding to the formula:

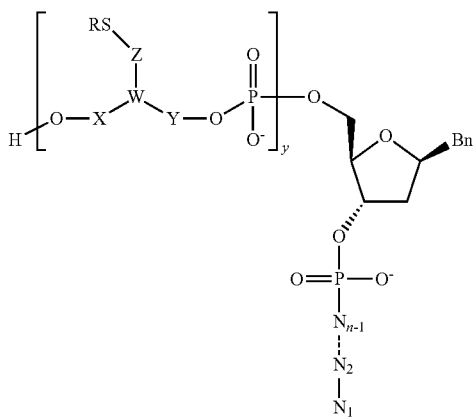

in which, n is an integer ranging from 4 to 100, y is an integer ranging from 2 to 12, $N_1, \ldots, N_n$ represent, independently of one another, a nucleotide, X is selected from the group consisting of linear or branched C1-C12 alkyl groups, C1-C12 aminoalkyl groups, C1-C12 alkoxy groups, C3-C12 cycloalkyl groups, and oxygen-containing or nitrogen-containing C3-C12 cycloheteroalkyl groups, Y is selected from the group consisting of linear or branched C1-C12 alkyl groups, C1-C12 aminoalkyl groups, C1-C12 alkoxy groups, C3-C12 cycloalkyl groups, and oxygen-containing or nitrogen-containing C3-C12 cycloheteroalkyl groups, Z is selected from the group consisting of C1-C12 alkoxy groups, oxygen-containing or nitrogen-containing C3-C12 cycloheteroalkyl groups, C1-C12 NCO-alkyl groups, and C1-C12 CON-alkyl groups, W is selected from the group consisting of C1-C12 alkane triyl groups, C6-C18 aryl triyl groups, and C6-C18 aralkane triyl groups, R is H or is selected from the group consisting of C1-C12 acyl, C1-C12 S-alkyl, C6-C12 S-aryl, S-2-pyridine, oxygen-containing or nitrogen-containing C1-C12 S-heteroalkyl, C3-C12 S-cycloalkyl, and oxygen-containing or nitrogen-containing C3-C12 S-cycloheteroalkyl groups, and $B_n$ represents the base of the n-th nucleotide.

2. The modified oligonucleotide according to claim 1, in which the nucleotide sequence ($N_1$-$N_2$- . . . -$N_{n-1}$-$N_n$) is specific to a virus, a bacterium or a gene responsible for or involved in a disease.

3. The modified oligonucleotide according to claim 2, in which the nucleotide sequence ($N_1$-$N_2$- . . . -$N_{n-1}$-$N_n$) is selected from the group consisting of:
the sequences SEQ ID NO: 1, SEQ ID NO: 4, SEQ ID NO: 27, SEQ ID NO: 28, SEQ ID NO: 35 and SEQ ID NO: 36 specific to the hepatitis C virus (HCV),
the sequences SEQ ID NO: 16, SEQ ID NO: 17 and SEQ ID NO: 40, specific to the flaviviruses,
the sequence SEQ ID NO: 18 and SEQ ID NO: 41, specific to the dengue viruses, and
the sequence SEQ ID NO: 19, specific to the West Nile viruses (WNV).

4. The modified oligonucleotide according to claim 1, in which the nucleotide sequence ($N_1$-$N_2$- . . . -$N_{n-1}$-$N_n$) has a structure of the alpha anomer, beta anomer, linear, or "snail" type.

5. A grafted substrate comprising at least one modified oligonucleotide according to claim 1, said substrate comprising at least one receiving zone coated with a substance that tolerates the grafting of said modified oligonucleotide.

6. The grafted substrate according to claim 5, in which:
said receiving zone is coated with a gold or platinum film, and said substrate is of metal, or
said receiving zone comprises on its surface at least one carbon-carbon double bond or carbon-carbon triple bond or haloacetamide functions, and said substrate is of plastic.

7. The grafted substrate according to claim 5, in which said substrate is non-planar.

8. A method for detecting at least one target nucleic acid, comprising a step of:
detecting said at least one nucleic acid with the grafted substrate according to claim 5.

9. A method for detecting at least one target nucleic acid in a biological sample, comprising a step of:
detecting said target nucleic acid with at least one detection probe formed by a modified oligonucleotide according to claim 1.

10. The method according to claim 9, comprising the steps of:
obtaining at least one source nucleic acid from said biological sample,
producing an amplicon by the amplification of said target nucleic acid from the source nucleic acid, and
detecting the hybridization of said amplicon with at least one detection probe formed by a modified oligonucleotide according to claim 1.

11. The method according to claim 10, for determining a genotype and/or subtype of a virus present in a biological sample, in which
the amplicon is generated by the amplification of a target nucleotide sequence, corresponding to a genomic region of virus bearing information relating to the genotype and/or subtype, and
detection of the hybridization of said amplicon with said at least one detection probe is carried out with a probe specific to a viral genotype and/or subtype.

12. The method according to claim 11, in which the step of production of the amplicon is carried out by amplifying a target nucleotide sequence corresponding to a genomic region of the virus bearing information relating to the viral genotype and/or subtype, with a mixture of nucleotide primer pairs selected from the group consisting of:
SEQ ID NO: 8 and SEQ ID NO: 9, when the amplicon is generated starting from any genotype of HCV;
SEQ ID NO: 10 and SEQ ID NO: 9, when the amplicon is generated starting from an HCV of genotype 1a/1b;
SEQ ID NO: 29 and SEQ ID NO: 9, when the amplicon is generated starting from an HCV of genotype 2;
SEQ ID NO: 8 and SEQ ID NO: 11, when the amplicon is generated starting from an HCV of genotype 3a;
SEQ ID NO: 8 and SEQ ID NO: 30, when the amplicon is generated starting from an HCV of genotype 4a/4b; and
SEQ ID NO: 20 and SEQ ID NO: 21, or SEQ ID NO: 22 and SEQ ID NO: 21 when the amplicon is generated from a flavivirus.

13. The method according to claim 9, wherein the method is applied for diagnostics, genotyping or sequencing of viral strains.

14. The method according to claim 13, wherein the method is applied for diagnostics, genotyping or sequencing of HCV, HBV, dengue viruses or West Nile virus.

15. A kit for detecting at least one target nucleic acid in a biological sample comprising:
at least one modified oligonucleotide according to claim 1 and at least one substrate comprising at least one receiving zone coated with a substance that tolerates the grafting of said modified oligonucleotide, said receiving zone being coated with gold, with platinum or comprising on its surface at least one carbon-carbon double bond or carbon-carbon triple bond or haloacetamide functions, or
at least one grafted substrate according to claim 5.

* * * * *